US010344033B2

(12) United States Patent
Boyle et al.

(10) Patent No.: US 10,344,033 B2
(45) Date of Patent: Jul. 9, 2019

(54) 2-AMINOQUINAZOLINE DERIVATIVES AS P70S6 KINASE INHIBITORS

(71) Applicant: SENTINEL ONCOLOGY LIMITED, Cambridge (GB)

(72) Inventors: Robert George Boyle, Cambridge (GB); David Winter Walker, Cambridge (GB)

(73) Assignee: SENTINEL ONCOLOGY LIMITED, Cambridge (GB)

(*) Notice: Subject to any disclaimer, the term of this patent is extended or adjusted under 35 U.S.C. 154(b) by 0 days.

(21) Appl. No.: 15/764,960

(22) PCT Filed: Sep. 30, 2016

(86) PCT No.: PCT/EP2016/073489
§ 371 (c)(1),
(2) Date: Mar. 30, 2018

(87) PCT Pub. No.: WO2017/055592
PCT Pub. Date: Apr. 6, 2017

(65) Prior Publication Data
US 2018/0370975 A1 Dec. 27, 2018

(30) Foreign Application Priority Data
Oct. 2, 2015 (GB) .................................. 1517451.9
Aug. 16, 2016 (GB) .................................. 1614037.8

(51) Int. Cl.
*C07D 487/04* (2006.01)
*A61P 25/28* (2006.01)
*C07D 403/04* (2006.01)
*A61P 35/04* (2006.01)

(52) U.S. Cl.
CPC ............ *C07D 487/04* (2013.01); *A61P 25/28* (2018.01); *A61P 35/04* (2018.01); *C07D 403/04* (2013.01)

(58) Field of Classification Search
CPC ............................... C07D 487/04; A61P 25/28
See application file for complete search history.

(56) References Cited

FOREIGN PATENT DOCUMENTS

| | | | |
|---|---|---|---|
| WO | 2007/117607 | A2 | 10/2007 |
| WO | 2008/079988 | A2 | 7/2008 |
| WO | 2009/046448 | A1 | 4/2009 |
| WO | 2009/153313 | A1 | 12/2009 |
| WO | 2010/056320 | A2 | 5/2010 |
| WO | 2010/056758 | A1 | 5/2010 |
| WO | 2010/136755 | A1 | 12/2010 |
| WO | 2014/085528 | A1 | 6/2014 |
| WO | 2015/054572 | A1 | 4/2015 |
| WO | 2016/131776 | A1 | 8/2016 |

OTHER PUBLICATIONS

International Search Report and Written Opinion for PCT/EP2016/073489, dated Jan. 19, 2017.
UKIPO Search Report for GB1517451.9 dated Jun. 28, 2016.

*Primary Examiner* — Golam M Shameem
(74) *Attorney, Agent, or Firm* — Heslin Rothenberg Farley & Mesiti P.C.

(57) ABSTRACT

The invention provides compound that inhibit or modulate the activity of p70S6 kinase, the compounds being of the formula (1):

(1)

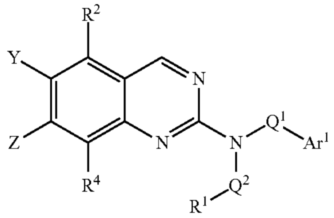

or a salt, tautomer or N-oxide thereof;
wherein:

one of Y and Z is $R^3$ and the other is $Ar^2$;

$Q^1$ is an optionally substituted $C_{1-8}$ alkylene group; and wherein a carbon atom of the $C_{1-8}$ alkylene group may optionally be replaced by a cyclopropane-1,1-diyl or cyclobutane-1,1-diyl group provided that the total number of carbon atoms in an alkylene group containing such a replacement does not exceed 8;

$Q^2$ is a bond or an optionally substituted $C_{1-8}$ alkylene group $R^1$ is selected from hydrogen, $NR^xR^y$ and a group $Cy^1$;

$R^x$ and $R^y$ are each is selected from hydrogen, $C_{1-4}$ hydrocarbyl or hydroxy-$C_{1-4}$ hydrocarbyl; or $NR^xR^y$ forms an optionally substituted 4 to 7-membered heterocyclic ring;

$Cy^1$ is an optionally substituted C-linked 3 to 7 membered monocyclic non-aromatic carbocyclic or heterocyclic;

$R^2$ and $R^4$ are each is selected from hydrogen, fluorine, chlorine, optionally substituted $C_{1-2}$ alkyl and optionally substituted $C_{1-2}$ alkoxy;

$R^3$ is selected from hydrogen, fluorine, chlorine, optionally substituted $C_{1-2}$ alkyl and optionally substituted $C_{1-2}$ alkoxy;

$Ar^1$ is an optionally substituted monocyclic 5 or 6-membered aryl or heteroaryl ring; and $Ar^2$ is an optionally substituted bicyclic 8 to 11-membered heteroaryl group.

The compounds are useful in medicine, for example in the treatment of a disease or condition selected from cancers, neurodevelopmental diseases and neurodegenerative diseases.

20 Claims, 3 Drawing Sheets

2-AMINOQUINAZOLINE DERIVATIVES AS P70S6 KINASE INHIBITORS

CROSS REFERENCE TO RELATED APPLICATIONS

This application is a national stage filing under section 371 of International Application No. PCT/EP2016/073489, filed on Sep. 30, 2016, and published on Apr. 6, 2017 as WO 2017/055592, which claims priority to Great Britain Application No. 1614037.8, filed on Aug. 16, 2016 and to Great Britain Application No. 1517451.9, filed on Oct. 2, 2015. The entire contents of WO 2017/055592 are hereby incorporated herein by reference.

This invention relates to compounds that inhibit or modulate the activity of p70S6 kinase, pharmaceutical compositions containing the compounds and the therapeutic uses of the compounds.

BACKGROUND OF THE INVENTION

The enzyme, p70S6 kinase (also known as p70S6K, p70S6K1, pS6K, S6K, S6K1) is a serine-threonine kinase and a member of the AGC family. It is a downstream effector of the phosphatidylinositol 3 kinase (PI3K)/AKT/mammalian target of rapamycin (mTOR) signalling pathway and p70S6K undergoes phosphorylation and activation in response to growth factors such as IGF-I, EGF, TGF-[alpha] and HGF.

Activation of p70S6K in turn phosphorylates a number of proteins involved in protein translation including Ribosomal protein S6 (RPS6), eIF4B and eEF2K. The net effect of this is to promote translation leading to an increase in protein synthesis in a cell. High levels of protein synthesis are required for cellular proliferation. It has also been shown that p70S6K has a necessary role in the mitotic cycle of a cell (Lane et al, Nature, 1993, 363(6425):170-2).

The kinase p70S6K has been shown to be constitutively activated in human tumour cells, leading to tumour cell proliferation. Inhibition of the mTOR/p70S6K pathway has been shown to lead to a decrease in tumour cell proliferation and an increase in tumour cell apoptosis (Pene et al (2002) Oncogene 21, 6587 and Le et al (2003) Oncogene 22, 484). Inhibition of p70S6K activity would therefore present an attractive approach for the treatment of cancer.

The mTOR/p70S6K pathway has been shown to be activated in renal cell carcinoma and is inhibited by CCI-779 (Robb, V. A.; Karbowniczek, M.; Klein-Szanto, A. J.; Henske, E. P. *J Urol* 2007, 177, 346-52). Furthermore, patients with glioblastoma multiforme whose tumours express high levels of phosphorylated p70S6K have been found to benefit from treatment with CCI-779 (Galanis et al. *J. Clin. Oncol.* 2005, 23, 5294-304).

In addition, a significant linear association between time to disease progression and inhibition of p70S6K activity in peripheral blood mononuclear cells (PBMCs) following administration of the mTOR inhibitor CCI-779 has been reported for Renal Cell Carcinoma patients by Peralba et al [(2003) Clinical Cancer Research 9, 2887]. This indicates that activity of p70S6K is a driver of disease in this setting and that p70S6K activity can be potentially be used as a clinical biomarker.

The gene RPS6KB1 that codes for p70S6K, is localized to chromosomal region 17q23 and this region is amplified in Breast Cancer (Cancer Res. (1999) 59: 1408-11 Localization of pS6K to Chromosomal Region 17q23 and Determination of Its Amplification in Breast Cancer). This leads to overexpression of p70S6K protein and a statistically significant association between amplification and poor prognosis has been observed in breast cancer patients (Detecting activation of ribosomal protein S6 kinase by complementary DNA and tissue microarray analysis. J. Natl. Cancer Inst. 2000; 92:1252-9).

Furthermore, Belletti et al published that S6K1 mediates survival and recurrence of Breast Cancer following surgery (Mol Oncol. 2014 May; 8(3):766-80).

P70S6K has a role in migration and invasion of ovarian cancer (p70 S6 kinase in the control of actin cytoskeleton dynamics and directed migration of ovarian cancer cells, Oncogene (2011), 1-13). In addition, it has been revealed that p70S6K has a role in promoting invasion, migration and metastasis of highly aggressive Triple-Negative Breast Cancer cells (Targeting p70S6K Prevented Lung Metastasis in a Breast Cancer Xenograft Model, Akar et al, Molecular Cancer Therapeutics (2010), 9 (5), 1180 and Hung et al, S6K1 promotes invasiveness of breast cancer cells in a model of metastasis of triple-negative breast cancer, Am. J. Transl, Res. 2014 Jul. 18; 6(4):361-76).

In addition, Lymphangioleiomyomatosis (LAM) is a disease typified by hyper-activation of the PI3K/Akt/mTOR/p70S6K axis due to mutation inactivation of the repressor complex, Tuberous Sclerosis Complex (TSC). LAM cells are also metastatic, giving rise to metastasis in the lung.

LAM is a rare destructive lung disease, almost exclusively of women, and is associated with the metastasis of tuberin-null cells (Taveira-DaSilva et al. (2006). Cancer Control. 2006; 13:276-285). Metastatic lesions develop in distant organs including lungs, kidney and lymph nodes, representing a severe and debilitating disease burden.

LAM occurs either sporadically or as a manifestation of Tuberous Sclerosis Complex (TSC), a dominant autosomal inherited disorder (Expert review on http://www.orpha.net). LAM and TSC disorders are characterized by nullifying mutations in tumour suppressors TSC1 or TSC2 leading to hyper activation of mTOR and of S6K1. This in turn drives cell growth & proliferation of LAM cells (Holz et al. (2014), Cell Cycle 2014; 13:371-382). S6K1 is also known to promote metastasis in other cancers: breast (Akar et al. (2010), Mol Cancer Ther; 9(5)) and ovarian (Wong et al. (2011), Oncogene (2011) 30, 2420-2432). Due to the reliance of LAM cells on S6K1, and of the likely role of S6K1 in the metastatic process, it is anticipated that an S6K1 inhibitor will have disease-modifying properties for LAM.

Sporadic LAM has a prevalence of approximately 1 in 125,000 births whereas Pulmonary LAM, arising from TSC, has a prevalence of approximately 1 in 15,000 births (figures from internet rare disease database, http://www.orpha.net). No approved therapies exist for LAM and hence LAM is currently classified as an orphan disease.

Given that p70S6K promotes translation, it is known that p70S6K has a crucial role in the pathology of diseases that rely on excessive protein synthesis (for example, Fragile X Syndrome, Genetic Removal of p70 S6 Kinase 1 Corrects Molecular, Synaptic, and Behavioral Phenotypes in Fragile X Syndrome Mice. Klann et al, Neuron, Volume 76, Issue 2, p325-337, 18 Oct. 2012). Furthermore, p70S6K has a role in the pathology of cancers involving synthesis of oncogenic proteins such as c-Myc e.g. pancreatic cancer (The mTORC1/S6K1 Pathway Regulates Glutamine Metabolism through the eIF4B Dependent Control of c-Myc Translation, Blenis et al, Current Biology, Volume 24, Issue 19, p2274-2280, 6 Oct. 2014). For treatment of these conditions it would be advantageous to use an orally bioavailable p70S6K inhibitor to correct the excessive protein synthesis.

P70S6K has been implicated in the pathology of a number of cancers of the brain. Such conditions include, but are not limited to:

- Brain metastases arising from cancers elsewhere in the body, for example brain metastases arising from a breast cancer such as Triple-Negative Breast Cancer (Distant metastasis in triple-negative breast cancer. Neoplasma 2013; 60: 290-294)
- Brain metastases from metastatic breast cancer (Central nervous system or brain metastases traditionally occur in 10-16% of metastatic breast cancer patients and are associated with a dismal prognosis—see *Breast Dis.* 2006-2007; 26:139-47.)
- Gliomas and Glioblastomas (S6K1 Plays a Key Role in Glial Transformation, Cancer Research (2008), 68(16), 6516-6523)

Furthermore, a p70S6K inhibitor may be particularly useful for treating the following cancers which are reliant on p70S6K signalling:

- Bladder cancer
- Breast cancer
- Colo-rectal cancer (CRC)
- Diffuse large B-cell lymphomas (DLBCL)
- Gallbladder cancer
- Gliomas and Glioblastomas
- Head and Neck cancers
- Hepatocellular carcinoma
- Human Olfactory Neuroblastoma
- Leukaemias
- Lymphomas
- Nasopharyngeal carcinoma
- Neuroendocrine cancer
- Non-Small Cell Lung Cancer (NSCLC)
- Small cell lung cancer
- Ovarian cancer
- Pancreatic cancer
- Pheochromocytoma
- Renal Cell Carcinoma (RCC)
- Squamous cell carcinoma
- Metastases, for example bone metastases and lung metastases P70S6K also has a crucial role in the pathology of a number of neurodevelopmental diseases (many referenced in The Autistic Neuron: Troubled Translation?. Bear et al, Cell 135, Oct. 31, 2008). In particular, these diseases are caused by the excessive protein synthesis that is driven by P70S6K. Such conditions include, but are not limited to:

- Fragile X Syndrome, a rare neuro-developmental disease caused by excessive levels of p70S6K activity
- Autism and Autism Spectrum Disorders
- Fragile X-associated tremor/ataxia syndrome (FXTAS)
- Angleman's syndrome
- Tuberous sclerosis
- PTEN hamartoma syndrome
- MECP2 duplication syndrome
- Neurofibromatosis
- Alzheimer's Disease (refer to (1) Oddo et al, Reducing Ribosomal Protein S6 Kinase 1 Expression Improves Spatial Memory and Synaptic Plasticity in a Mouse Model of Alzheimer's Disease, The Journal of Neuroscience, Oct. 14, 2015, 35(41):14042-14056 and (2) Genetic reduction of mammalian target of rapamycin ameliorates Alzheimer's disease-like cognitive and pathological deficits by restoring hippocampal gene expression signature, Journal of Neuroscience (2014), 34(23), 7988-7998)
- Down Syndrome (mTOR Hyperactivation in Down Syndrome Hippocampus Appears Early During Development, Journal of Neuropathology & Experimental Neurology (2014), 73(7), 671-683)

PTEN Hamartoma Syndrome

PTEN hamartoma tumour syndrome (PHTS) encompasses four major clinically distinct syndromes associated with germline mutations in the tumour suppressor PTEN. These allelic disorders, Cowden syndrome, Bannayan-Riley-Ruvalcaba syndrome, Proteus syndrome, and Proteus-like syndrome are associated with unregulated cellular proliferation leading to the formation of hamartomas (benign and malignant tumours of the thyroid, breast, and endometrium) (Genetics in Medicine (2009) 11, 687-694). The absence of PTEN leads to loss of down-regulation of phosphorylated Akt which in turn allows for unchecked survival, growth and proliferation of the cells in question. As S6K1 is a key effector of Akt, an S6K1 inhibitor may have utility in controlling the growth of the cancer. Prevalence of PHTS is currently unknown.

Neurofibromatosis Type 1

Neurofibromatosis type 1 is a condition characterized by changes in skin colouring (pigmentation) and the growth of tumours along nerves in the skin, brain, and other parts of the body. The signs and symptoms of this condition vary widely among affected people. Most adults with neurofibromatosis type 1 develop neurofibromas, which are noncancerous (benign) tumours that are usually located on or just under the skin. These tumours may also occur in nerves near the spinal cord or along nerves elsewhere in the body. Some people with neurofibromatosis type 1 develop cancerous tumours that grow along nerves. These tumours, which usually develop in adolescence or adulthood, are called malignant peripheral nerve sheath tumours. People with neurofibromatosis type 1 also have an increased risk of developing other cancers, including brain tumours and cancer of blood-forming tissue (leukaemia).

Neurofibromatosis type 1 occurs in 1 in 3,000 to 4,000 people worldwide and currently surgery is the main treatment option; it is classed as an orphan disease as no targeted therapies exist (http://ghr.nlm.nih.gov/condition/neurofibromatosis-type-1)

Mutations in the NF1 gene cause neurofibromatosis type 1. The NF1 gene provides instructions for making neurofibromin protein. This protein is produced in many cells, including nerve cells and specialized cells surrounding nerves (oligodendrocytes and Schwann cells). Neurofibromin acts as a tumour suppressor. Mutations in the NF1 gene lead to the production of a non-functional version of neurofibromin that cannot regulate cell growth and division. As a result, tumours such as neurofibromas can form along nerves throughout the body. An S6K1 inhibitor may control growth of cells expressing mutated NF1 gene by dampening production of neurofibromin protein and other proteins essential to growth of the tumour.

Role of P70S6 in Neurological Diseases

P70S6K also has a crucial role in the pathology of a number of neurodevelopmental diseases (many referenced in The Autistic Neuron: Troubled Translation?. Bear et al, Cell 135, Oct. 31, 2008). In particular, these diseases are caused by the excessive protein synthesis that is driven by P70S6K.

It is well known that precise translation control (protein synthesis) is absolutely required for neurological processes of the brain such as long-lasting synaptic plasticity and the formation of long-term memory. Moreover, alterations in translational control are a common pathophysiological feature of human neurological disorders, including developmental disorders, neuropsychiatric disorders, and neurodegenerative diseases.

Furthermore, it is known that translational control mechanisms are susceptible to modification by small molecules that penetrate the brain (Klann and Santini, Dysregulated mTORC1-dependent translational control: from brain disorders to psychoactive drugs, Front. Behav. Neurosci., 8 Nov. 2011, doi: 10.3389/fnbeh.2011.00076).

S6K1 is well known as a master regulator of protein biosynthesis via its role in translation initiation as well as phosphorylation and activation of various substrates that drive protein production (eIF4B, PDCD4, SKAR, eEF2K, RPS6—for review refer to Ma and Blenis, Nature Reviews Molecular Cell Biology 10, 307-318 (May 2009), doi: 10.1038/nrm2672).

The following disorders are typified by underlying aberrations in regulation of protein translation which is linked to the pathologies observed. An S6K1 inhibitor, which acts by reducing excessive protein translation may therefore have utility as a therapy in such disorders.

It is possible to classify certain disorders into sub-groups: (1) Neurodevelopmental Disorders (2) Neurodegenerative Diseases. Within each sub-class the disorders are linked by common themes:

1. Neurodevelopmental Disorders

Neurodevelopmental disorders are defined as diseases caused by abnormal development of the brain during the first two decades of life. It is possible to define a subgroup of these disorders that are characterized by single-gene mutations. A common molecular abnormality in several of these disorders is loss-of-function mutations and/or deletion of genes that encode proteins that normally repress the mTORC1 signalling pathway. These disorders are listed below.

Fragile X Syndrome

Fragile X syndrome (FXS) is a genetic condition that gives rise to a range of developmental problems including learning disabilities and cognitive impairment. Usually, males are more severely affected by this disorder than females, owing to the fact that the condition is inherited via the X-chromosome. Affected individuals usually have delayed development of speech and language by age 2. Most males with FXS have mild to moderate intellectual disability, while about one-third of affected females are intellectually disabled. Children with FXS may also have anxiety and hyperactive behaviour such as fidgeting or impulsive actions. They may have attention deficit disorder (ADD), which includes an impaired ability to maintain attention and difficulty focusing on specific tasks.

About one-third of individuals with FXS have features of autism spectrum disorders that affect communication and social interaction. Seizures occur in about 15 percent of males and about 5 percent of females with FXS. Most males and about half of females with FXS have characteristic physical features that become more apparent with age. These features include a long and narrow face, large ears, a prominent jaw and forehead, unusually flexible fingers, flat feet, and in males, enlarged testicles (macro-orchidism) after puberty. FXS occurs in approximately 1 in 4,000 males and 1 in 8,000 females.

Mutations in the Fmr1 gene cause FXS. The Fmr1 gene provides instructions for making a protein called fragile X mental retardation 1 protein, or FMRP. This protein helps regulate the production of other proteins and plays a role in the development of synapses, which are specialized connections between nerve cells. Synapses are critical for relaying nerve impulses.

Nearly all cases of FXS are caused by a mutation in a DNA segment, known as the CGG triplet repeat, in the Fmr1 gene. Normally, this DNA segment is repeated in the range between 5 and 44 times (more commonly either 29 or 30 times). In people with FXS, however, the CGG segment is repeated more than 200 times. The abnormally expanded CGG segment turns off (silences) the Fmr1 gene, which prevents the gene from producing FMRP.

FMRP is a repressor of protein translation. In the case of FXS patients, who either experience a loss or shortage of FMRP, there is no repression of translation, leading to excessive production of an array of proteins normally controlled by FMRP. A number of these proteins are expressed in the neurons and control synaptic plasticity (memory formation, learning, ability to store information). Lack of control of production of these proteins leads to the neuropathological state observed in FXS patients. Klann et al published that S6K1 has a central role in the excessive translation of these proteins and that genetic knock-out of S6K1 resulted in correction of phenotypes in the mouse model of FXS (Genetic Removal of p70 S6 Kinase 1 Corrects Molecular, Synaptic, and Behavioral Phenotypes in Fragile X Syndrome Mice. Neuron 76, 325-337, 2012). It has been determined that S6K1 inhibitors described herein also have the ability to dampen protein synthesis in the neurons, leading to correction of aberrant phenotypes in a mouse model of FXS.

Furthermore, Tassone et al (Genes, Brain and Behavior (2012), doi: 10.1111/j.1601-183X.2012.00768.x) published that lymphocytes isolated from the blood of human FXS patients exhibited higher levels of phosphorylated (activated) p70S6K and also higher levels of phosphorylated RPS6, the direct substrate of S6K1. This confirms that p70S6K is more highly activated in human FXS patients and supports the notion of inhibiting p70S6K activity in order to correct the disease. In addition, this represents a possible clinical biomarker so as to assess the pharmacodynamics effect of the p70S6K inhibitor in the clinic.

Fragile X-Associated Tremor/Ataxia Syndrome (FXTAS)

Fragile X-associated tremor/ataxia syndrome (FXTAS) is a rare neurodegenerative disorder characterized by adult-onset progressive intention tremor and gait ataxia. It is an X-linked genetic disorder and as such, the disease primarily affects males (Orphanet rare disease database, http://www.orpha.net/consor/cgi-bin/index.php?lng=EN)

Prevalence is estimated at 1-9 in 100,000 individuals. The age of onset of tremor and/or ataxia in males is about 60 years. The clinical presentation is variable with dominant manifestations including: intention tremor, progressive cerebellar gait ataxia, frontal executive dysfunction, cognitive decline, peripheral neuropathy, and dysautonomia. Other signs include mild Parkinsonism and psychiatric manifestations (depression, anxiety and agitation) with possible progression to dementia. Carrier females generally have less severe manifestations than males but also have an increased risk of primary ovarian insufficiency, chronic muscle pain, and hypothyroidism. FXTAS is caused by a CGG trinucleotide repeat expansion (55-200 repeats) in the permutation range of the Fmr1 gene. There is no specific treatment for FXTAS that targets the underlying pathological mechanism; FXTAS is therefore classed as an orphan disease. The CGG trinucleotide repeat expansion often leads to reduced levels of FMRP protein, a repressor of protein translation. This leads to excessive protein translation which may be counteracted by use of an S6K1 inhibitor.

Autism and Autism Spectrum Disorders

Autism spectrum disorder (ASD) and autism are terms for a group of complex disorders of brain development. The disorders are characterized by difficulties in social interaction, verbal and nonverbal communication and repetitive behaviours. A publication in 2013 titled the Diagnostic and Statistical Manual of Mental Disorders (DSM-5) brought together all autism disorders into one umbrella diagnosis of ASD. Previously, they were recognized as distinct subtypes, including autistic disorder, childhood disintegrative disorder, pervasive developmental disorder—not otherwise specified (PDD-NOS) and Asperger syndrome. The U.S. Centers for Disease Control and Prevention (CDC) identify around 1 in 68 American children as on the autism spectrum. Studies also show that autism is four to five times more common among boys than girls. An estimated 1 out of 42 boys and 1 in 189 girls are diagnosed with autism in the United States. Overall, ASD affects over 3 million individuals in the U.S. and tens of millions worldwide (Autism Speaks website, http://www.autismspeaks.org/). Moreover, government autism statistics suggest that prevalence rates are on the increase. Fragile X syndrome (FXS) is the most common inherited cause of intellectual disabilities and the most common known cause of autism worldwide (Penagarikano et al (2007). The pathophysiology of Fragile X Syndrome. Annu. Rev. Genomics Hum. Genet. 8, 109-129). This causative link between FXS and autism indicates that an S6K1 inhibitor that exhibits efficacy in treating FXS may also be useful in treatment of autism and ASDs.

Angelman Syndrome

Angelman syndrome (AS) is a neurogenetic disorder that is usually diagnosed in infants and is characterized by developmental delay, severe intellectual disability, absent speech, exuberant behaviour with happy demeanor, motor impairment, and epilepsy. AS is caused by deficient UBE3A gene expression that may be caused by various abnormalities of chromosome 15 (Dan, B., Angelman syndrome: Current understanding and research prospects. Epilepsia, 2009. 50(11): p. 2331-2339). Although not precisely known, prevalence of AS among children and young adults is between 1/10,000 and 1/20,000 defining AS as a rare disease. Mutations in the E3 ubiquitin ligase UBE3A have been identified in AS, suggesting that ubiquitin-dependent protein turnover may be impaired in this disorder, possibly leading to elevated synaptic protein levels (Jiang and Beaudet, 2004). Furthermore, it has been disclosed that S6K1 inhibition can improve hippocampal synaptic plasticity and learning in a mouse model of Angelman syndrome (Cellular and Molecular Life Sciences pp 1-12). An S6K1 kinase inhibitor would exert its effect by reducing translation of synaptic protein levels.

Tuberous Sclerosis Complex

Tuberous sclerosis complex is a genetic disorder characterized by the growth of numerous noncancerous (benign) tumours in many parts of the body. These tumours can occur in the skin, brain, kidneys, and other organs, in some cases leading to significant health problems. Tuberous sclerosis complex also causes developmental problems, and the signs and symptoms of the condition vary from person to person.

Tuberous sclerosis complex often affects the brain, causing seizures, behavioural problems such as hyperactivity and aggression, and intellectual disability or learning problems. Some affected children have the characteristic features of autism, a developmental disorder that affects communication and social interaction, as described above. Benign brain tumours can also develop in people with tuberous sclerosis complex; these tumours can cause serious or life-threatening complications. Tuberous sclerosis complex affects about 1 in 6,000 people (http://ghr.nlm.nih.gov/condition/tuberous-sclerosis-complex)

Mutations in the TSC1 or TSC2 gene can cause tuberous sclerosis complex. The TSC1 and TSC2 genes provide instructions for making the proteins hamartin and tuberin, respectively. These proteins are involved in the signalling network of the PI3K pathway and act as tumour suppressors, inhibiting the activation of mTOR via Rheb-GTP. When TSC1 or TSC2 are mutated this leads to loss of tumour suppressor function, leading to mTOR hyper-activation.

Importantly, the mTORC1 inhibitor rapamycin has been shown to be effective in ameliorating learning and memory deficits in TSC2 heterozygous knockout mice (Ehninger et al., 2008b), suggesting that uncontrolled mTORC1 signalling is a core molecular mechanism involved in the behavioural abnormalities.

One of the functional effectors of mTOR is S6K1; therefore, inhibiting S6K1 function may have ameliorative effects in the disease MECP2 Duplication Syndrome MECP2 duplication syndrome is a genetic condition that is inherited in an X-linked pattern and occurs almost exclusively in males. It is characterized by moderate to severe intellectual disability. Most people with this condition also have weak muscle tone in infancy, feeding difficulties, poor or absent speech, and seizures that may not improve with treatment or muscle stiffness (spasticity). Individuals with MECP2 duplication syndrome have delayed development of motor skills such as sitting and walking. Many individuals with MECP2 duplication syndrome have recurrent respiratory tract infections. These respiratory infections are a major cause of death in affected individuals, with almost half succumbing by age 25. The prevalence of MECP2 duplication syndrome is unknown; approximately 120 affected individuals have been reported in the scientific literature. MECP2 duplication syndrome arises due to a duplication of the MECP2 gene which leads to excessive production of MeCP2 protein in the brain. MeCP2 is a regulator of expression of other genes. Whilst MeCP2 is critical for normal brain function, an excess can lead to abnormal regulation of the target genes (http://ghr.nlm.nih.gov/condition/mecp2-duplication-syndrome). An S6K1 inhibitor may reduce production of MeCP2 protein via global dampening of translation and may have utility as therapeutic intervention in this disease.

Down Syndrome

Down syndrome (DS) or Down's syndrome, also known as trisomy 21, is a genetic disorder caused by the presence of all or part of a third copy of chromosome 21 (Patterson, D (July 2009). "Molecular genetic analysis of Down syndrome." Human Genetics 126 (1): 195-214). It is typically associated with physical growth delays, characteristic facial features, and mild to moderate intellectual disability. DS is the most common chromosome abnormality in humans, occurring in about one per 1000 babies born each year (Weijerman, M E; de Winter, J P (December 2010). "Clinical practice. The care of children with Down syndrome". European journal of pediatrics 169 (12): 1445-52).

Recent publications have identified that mTOR hyperactivation plays a role in DS in the early stages of development. In control (non-DS) hippocampi phosphorylated S6 was only detected prenatally; it became undetectable 2 months postnatally. Conversely, for DS patients, phosphorylated S6 and phosphorylated S6 kinase were detected prenatally and persisted throughout postnatal development. This was linked to increased expression of phosphorylated S6 protein (RPS6), phosphorylated p70S6K, phosphorylated eukaryotic initiation factor 4E binding protein 1, and phosphorylated mTOR in DS hippocampus compared with controls (J Neuropathol Exp Neurol. 2014 July; 73(7):671-83). Furthermore, it has been suggested that mTOR inhibitors such as Rapamycin or other Rapalogs may be of utility in treating Cognitive Deficits associated with DS (CNS Neurol Disord Drug Targets. 2014 February; 13(1):34-40). As S6K1 controls phosphorylation and activation of S6 protein, an S6K1 inhibitor may be of therapeutic utility in counteracting the hyper-activated mTOR signalling in DS patients.

2. Neurodegenerative Diseases

Alzheimer's Disease

The clinical symptoms of Alzheimer's disease (AD) include a gradual memory loss and subsequent dementia, and neuropathological deposition of senile plaques and neurofibrillary tangles. AD accounts for 60% to 70% of cases of dementia (Burns, A; Lliffe, S (5 Feb. 2009). "Alzheimer's disease." BMJ (Clinical research ed.) 338: b158). It is a devastating and relatively widespread disease—as of 2010, there were between 21 and 35 million people worldwide with AD ("Survival in dementia and predictors of mortality: a review". International journal of geriatric psychiatry 28 (11): 1109-24).

At the molecular level, AD is associated with (1) the progressive accumulation of amyloid β-peptides (Aβ) in the form of extracellular amyloid plaques in the human brain and (2) tau hyperphosphorylation. Recent publications have implicated the PI3K/mTOR signalling pathway in the pathogenesis of the disease. For example, genetic knock-out of mTOR protein in Tg2576 mice, a widely used animal model of AD, was found to suppress amyloid-β deposits and rescue memory deficits in the animals (J. Neurosci. 2014 Jun. 4; 34(23):7988-98). Furthermore, testing of post-mortem brain tissue from human AD patients highlighted that alteration of mTOR signalling and autophagy occurs at early stages of AD, leading to a significant increase of Aβ (1-42) levels and hyper-activation of the PI3K/Akt/mTOR pathway (J. Neurochem. 2015 Jan. 27). The expression level of S6K1, the mTOR downstream target, was increased in these samples suggesting that a therapeutic intervention by an S6K1 inhibitor may be of utility to control synthesis of amyloid β protein and to dampen signalling from mTOR. Furthermore, increased levels of phosphorylated mTOR and S6K1 were also found in some of the brain areas affected in AD, such as cortex, of double APP/PS1 transgenic mice, a model of AD (Lafay-Chebassier et al., 2005).

In addition, Oddo et al (Reducing Ribosomal Protein S6 Kinase 1 Expression Improves Spatial Memory and Synaptic Plasticity in a Mouse Model of Alzheimer's Disease, The Journal of Neuroscience, Oct. 14, 2015, 35(41):14042-14056) published data that supports the following conclusions: (1) S6K1 activity is upregulated in the brains of AD patients (2) in a mouse model of AD, S6K1 activity in brain is also higher than control (3) Genetic reduction of S6K1 in the AD model mouse (via haplodeficiency) (1) improved synaptic plasticity and spatial memory deficits, and (2) reduced accumulation of Amyloid-B (AB) and phospho-tau/total tau levels, the key neuropathological hallmarks of AD. This validation gives credence to the hypothesis that manipulation of S6K1 activity via a small molecule S6K1 inhibitor could be a valid therapeutic approach in AD.

Huntington's Disease

Huntington's disease is an inherited, progressive brain disorder that causes uncontrolled movements, emotional problems, and loss of thinking ability (cognition); there are two forms of the disease: (1) adult-onset Huntington's disease, the most common form of this disorder, which usually appears in a person's thirties or forties and (2) Juvenile-onset Huntington's disease, which is less common and begins in childhood or adolescence. In both forms the disease is progressive with affected individuals usually living for only 10 to 15 years after signs and symptoms appear. Huntington's disease affects an estimated 3 to 7 people per 100,000 of European ancestry.

Huntington's disease is caused by mutations in the HTT gene which leads to production of an abnormally long version of the huntingtin (Htt) protein. The elongated protein is cut into smaller, toxic fragments that bind together and accumulate in neurons, disrupting the normal functions of these cells. The dysfunction and eventual death of neurons in certain areas of the brain underlie the signs and symptoms of Huntington's disease. Recent publications have shown that mutant Htt contributes to the pathogenesis of HD by enhancing mTORC1 activity (Sci. Signal., 28 Oct. 2014, Vol. 7, Issue 349, p. ra103).

One of the functional effectors of mTOR signalling is S6K1; therefore, inhibiting S6K1 function may have ameliorative effects in the disease. In addition, inhibiting S6K1 may limit the production of huntingtin protein via dampening of global protein translation.

Parkinson's Disease

Parkinson's disease (PD) is a progressive neurodegenerative condition resulting from the death of the dopamine-containing cells of the substantia nigra. People with PD classically present with the symptoms and signs associated with parkinsonism, namely bradykinesia, rigidity and rest tremor. PD is a common, chronic, progressive neurological condition, estimated to affect 100-180 people per 100,000 of the population (between 6 and 11 people per 6000 of the general population in the UK) and has an annual incidence of 4-20 per 100,000. There is a rising prevalence with age and a higher prevalence and incidence of PD in males (https://www.nice.org.uk/guidance/cg035/chapter/introduction).

Whilst PD traditionally has been considered a non-genetic disorder, at least 5% of people are now known to have forms of the disease that occur because of a mutation of one of several specific genes. Mutations in specific genes have been conclusively shown to cause PD. These genes code for alpha-synuclein (SNCA), parkin (PRKN), leucine-rich repeat kinase 2 (LRRK2 or dardarin), PTEN-induced putative kinase 1 (PINK1), DJ-1 and ATP13A2 (Lesage S, Brice A; Brice (April 2009). "Parkinson's disease: from monogenic forms to genetic susceptibility factors". Hum. Mol. Genet. 18 (R1): R48-59).

Recent studies addressing the mechanism of neurodegeneration in PD demonstrate the involvement of the mTORC1 signalling pathway in the survival mechanism of dopaminergic neurons. In vivo and in vitro studies show that degeneration induced by treatment with PD toxins, such as 6-OHDA and MPTP, leads to upregulation of RTP801, a protein encoded by a RTP801 stress-responsive gene, which in turn reduces mTOR kinase activity. It has been proposed that the molecular mechanism, linking high levels of RTP801 to mTORC1 inhibition and neurodegeneration involves TSC2 and Akt (Deyoung et al., 2008; Malagelada et al., 2008). Genetic manipulations that interfere with TSC2 or increase the expression of a constitutively active form of Akt protected against the PD toxins and prevented the increase in RTP801 (Malagelada et al., 2008). However, rapamycin was reported as a neuroprotective agent both in cell culture and in a MPTP mouse model (mouse model of PD). It was proposed that rapamycin may enhance Akt activity through inhibition of mTORC1-dependent activation of S6K1 and the subsequent reduction of phospho-IRS-1, which is a scaffold protein involved in the activation of PI3K and Akt (Shah et al., 2004). It therefore may also be the case that an inhibitor of S6K1 (a main effector of mTOR) will uncouple the same negative feedback loop to IRS-1, leading to activation of Akt and increased survival in the neurons of PD patients. An S6K1 inhibitor may therefore exhibit therapeutic effects when dosed to a PD patient.

For treatment of all the above described diseases it would be advantageous to use an orally bioavailable P70S6K inhibitor with properties allowing penetration of the brain in sufficient concentration to achieve efficacy.

It would therefore be beneficial to develop compounds that have the ability to inhibit p70S6 kinase.

The Invention

The present invention provides a class of novel arylalkylamino-substituted quinazolines as inhibitors of p70S6 kinase.

In a first embodiment (Embodiment 1.0) of the invention, there is provided a compound of the formula (1):

(1)

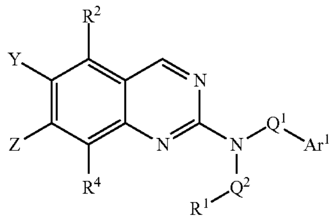

or a salt, tautomer or N-oxide thereof;

wherein:

one of Y and Z is $R^3$ and the other is $Ar^2$;

$Q^1$ is a $C_{1-8}$ alkylene group optionally substituted by one or two substituents selected from hydroxy and $C_{1-4}$ hydrocarbyloxy, provided that when a hydroxy substituent is present, there are at least two carbon atoms between the hydroxy substituent and the nitrogen atom to which $Q^2$ is attached; and wherein a carbon atom of the $C_{1-8}$ alkylene group may optionally be replaced by a cyclopropane-1,1-diyl or cyclobutane-1,1-diyl group provided that the total number of carbon atoms in an alkylene group containing such a replacement does not exceed 8;

$Q^2$ is a bond or a $C_{1-8}$ alkylene group optionally substituted by one or two substituents selected from hydroxy and $C_{1-4}$ hydrocarbyloxy, provided that when a hydroxy substituent is present, there are at least two carbon atoms between the hydroxy substituent and the nitrogen atom to which $Q^2$ is attached;

$R^1$ is selected from hydrogen, $NR^xR^y$ and a group $Cy^1$;

$R^x$ and $R^y$ are the same or different and each is selected from hydrogen, $C_{1-4}$ hydrocarbyl or hydroxy-$C_{1-4}$ hydrocarbyl; or $NR^xR^y$ forms a 4 to 7-membered heterocyclic ring containing a total of 1 or 2 heteroatom ring members of which one is N and the other is selected from N, O and S and oxidised forms thereof, the heterocyclic ring being optionally substituted with one or two substituents selected from $C_{1-4}$ hydrocarbyl, oxo, amino, mono-$C_{1-4}$ hydrocarbylamino, di-$C_{1-4}$hydrocarbylamino, fluorine and hydroxy, provided that there are at least two carbon atoms in line between the amino, mono-$C_{1-4}$ hydrocarbylamino, di-$C_{1-4}$hydrocarbylamino and hydroxy substituents when present and the nitrogen atom of the $NR^xR^y$ group;

$Cy^1$ is a C-linked 3 to 7 membered monocyclic non-aromatic carbocyclic or heterocyclic group containing 0, 1 or 2 heteroatom ring members selected from N, O and S and oxidised forms of S, wherein the carbocyclic and heterocyclic groups are optionally substituted with one or two substituents selected from $C_{1-3}$ hydrocarbyl, fluorine, oxo and hydroxy;

$R^2$ and $R^4$ are the same or different and each is selected from hydrogen, fluorine, chlorine, $C_{1-2}$ alkyl and $C_{1-2}$ alkoxy, wherein each $C_{1-2}$ alkyl and $C_{1-2}$ alkoxy is optionally substituted with two or more fluorine atoms;

$R^3$ is selected from hydrogen, fluorine, chlorine, $C_{1-2}$ alkyl and $C_{1-2}$ alkoxy, wherein each $C_{1-2}$ alkyl and $C_{1-2}$ alkoxy is optionally substituted with two or more fluorine atoms;

$Ar^1$ is a monocyclic 5 or 6-membered aryl or heteroaryl ring containing 0, 1 or 2 heteroatom ring members selected from O, N and S, the aryl or heteroaryl being optionally substituted with 1, 2 or 3 substituents $R^5$ which are the same or different and are selected from halogen, cyano and a group $R^a—R^b$;

$R^a$ is a bond, O, CO, $X^3C(X^4)$, $C(X^4)X^3$, $X^3C(X^4)X^3$, S, SO, $SO_2$, $NR^c$, $SO_2NR^c$ or $NR^cSO_2$;

$R^b$ is:

hydrogen;

a carbocyclic or heterocyclic group having from 3 to 7 ring members, of which 0, 1, 2 or 3 are heteroatom ring members selected from O, N and S and oxidised forms of S, the carbocyclic or heterocyclic group being optionally substituted with one or more substituents $R^6$; and an acyclic $C_{1-8}$ hydrocarbon group optionally substituted with one or more substituents selected from hydroxy; oxo; halogen; cyano; carboxy; amino; mono- or di-$C_{1-4}$ alkylamino; and carbocyclic and heterocyclic groups having from 3 to 7 ring members, of which 0, 1, 2 or 3 are heteroatom ring members selected from O, N and S and oxidised forms of S, the carbocyclic or heterocyclic group being optionally substituted with one or more substituents $R^6$; wherein one or two but not all of the carbon atoms of the acyclic $C_{1-8}$ hydrocarbon group may optionally be replaced by O, S, SO, $SO_2$, $NR^c$, $X^3C(X^4)$, $C(X^4)X^3$ or $X^3C(X^4)X^3$;

$R^6$ is selected from the substituents $R^5$ except that $R^6$ does not consist of or contain a carbocyclic or heterocyclic group;

$X^3$ is O, S or $NR^c$; and $X^4$ is =O, =S or =$NR^c$; and $R^c$ is hydrogen or $C_{1-4}$ hydrocarbyl;

$Ar^2$ is a bicyclic 8 to 11-membered heteroaryl group containing 1, 2, 3 or 4 heteroatom ring members selected from O, N and S and being optionally substituted with 1, 2 or 3 substituents $R^7$ selected from oxo, fluorine; chlorine; bromine; $C_{1-4}$ hydrocarbyl optionally substituted with one or more fluorine atoms; $C_{1-4}$ hydrocarbyloxy optionally substituted with one or more fluorine atoms; hydroxy; cyano; $N(R^c)_2$; $R^c—C(O)—$; $R^c—C(O)N(R^c)—$; $(R^c)_2NC(O)—$; $R—SO_2NR^c—$; $R^c—NHC(O)NH—$; $(R^c)_2NSO_2—$; and five and six-membered monocyclic groups containing from 0 to 3 heteroatom ring members selected from O, N and S, the five and six-membered monocyclic groups being unsubstituted or substituted with one or more substituents $R^8$ selected from $C_{1-4}$ hydrocarbyl, $C_{1-4}$ hydrocarbyloxy, cyano, hydroxy, oxo, halogen, amino, mono-$C_{1-4}$ hydrocarbylamino and di-$C_{1-4}$hydrocarbylamino and wherein the hydrocarbyl moieties when present are optionally substituted with fluorine, $C_{1-2}$ alkoxy, hydroxy, amino, mono-di-$C_{1-2}$alkylamino or di-$C_{1-4}$alkylamino;

and wherein, in each substituent consisting of or containing a hydrocarbyl group, the hydrocarbyl group is selected from alkyl, alkenyl, alkynyl and cycloalkyl groups and combinations thereof.

In another embodiment (Embodiment 1.1) of the invention, there is provided a compound of the formula (1):

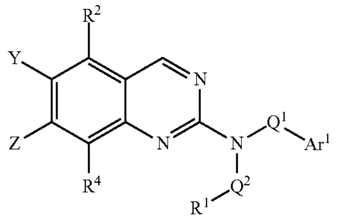

(1)

or a salt, tautomer or N-oxide thereof;

wherein:

one of Y and Z is $R^3$ and the other is $Ar^2$;

$Q^1$ is a $C_{1-8}$ alkylene group optionally substituted by one or two substituents selected from hydroxy and $C_{1-4}$ hydrocarbyloxy, provided that when a hydroxy substituent is present, there are at least two carbon atoms between the hydroxy substituent and the nitrogen atom to which $Q^2$ is attached;

$Q^2$ is a bond or a $C_{1-8}$ alkylene group optionally substituted by one or two substituents selected from hydroxy and $C_{1-4}$ hydrocarbyloxy, provided that when a hydroxy substituent is present, there are at least two carbon atoms between the hydroxy substituent and the nitrogen atom to which $Q^2$ is attached;

$R^1$ is selected from hydrogen, $NR^xR^y$ and a group $Cy^1$;

$R^x$ and $R^y$ are the same or different and each is selected from hydrogen, $C_{1-4}$ hydrocarbyl or hydroxy-$C_{1-4}$ hydrocarbyl; or $NR^xR^y$ forms a 4 to 7-membered heterocyclic ring containing a total of 1 or 2 heteroatom ring members of which one is N and the other is selected from N, O and S and oxidised forms thereof, the heterocyclic ring being optionally substituted with one or two substituents selected from $C_{1-4}$ hydrocarbyl, oxo, amino, mono-$C_{1-4}$ hydrocarbylamino, di-$C_{1-4}$hydrocarbylamino, fluorine and hydroxy, provided that there are at least two carbon atoms in line between the amino, mono-$C_{1-4}$ hydrocarbylamino, di-$C_{1-4}$hydrocarbylamino and hydroxy substituents when present and the nitrogen atom of the $NR^xR^y$ group;

$Cy^1$ is a C-linked 3 to 7 membered monocyclic non-aromatic carbocyclic or heterocyclic group containing 0, 1 or 2 heteroatom ring members selected from N, O and S and oxidised forms of S, wherein the carbocyclic and heterocyclic groups are optionally substituted with one or two substituents selected from $C_{1-3}$ hydrocarbyl, fluorine, oxo and hydroxy;

$R^2$ and $R^4$ are the same or different and each is selected from hydrogen, fluorine, chlorine, $C_{1-2}$ alkyl and $C_{1-2}$ alkoxy, wherein each $C_{1-2}$ alkyl and $C_{1-2}$ alkoxy is optionally substituted with two or more fluorine atoms;

$R^3$ is selected from hydrogen, fluorine, chlorine, $C_{1-2}$ alkyl and $C_{1-2}$ alkoxy, wherein each $C_{1-2}$ alkyl and $C_{1-2}$ alkoxy is optionally substituted with two or more fluorine atoms;

$Ar^1$ is a monocyclic 5 or 6-membered aryl or heteroaryl ring containing 0, 1 or 2 heteroatom ring members selected from O, N and S, the aryl or heteroaryl being optionally substituted with 1, 2 or 3 substituents $R^5$ which are the same or different and are selected from halogen, cyano and a group $R^a$-$R^b$;

$R^a$ is a bond, O, CO, $X^3C(X^4)$, $C(X^4)X^3$, $X^3C(X^4)X^3$, S, SO, $SO_2$, $NR^c$, $SO_2NR^c$ or $NR^cSO_2$;

$R^b$ is:

hydrogen;

a carbocyclic or heterocyclic group having from 3 to 7 ring members, of which 0, 1, 2 or 3 are heteroatom ring members selected from O, N and S and oxidised forms of S, the carbocyclic or heterocyclic group being optionally substituted with one or more substituents $R^6$; and an acyclic $C_{1-8}$ hydrocarbon group optionally substituted with one or more substituents selected from hydroxy; oxo; halogen; cyano; carboxy; amino; mono- or di-$C_{1-4}$ alkylamino; and carbocyclic and heterocyclic groups having from 3 to 7 ring members, of which 0, 1, 2 or 3 are heteroatom ring members selected from O, N and S and oxidised forms of S, the carbocyclic or heterocyclic group being optionally substituted with one or more substituents $R^6$; wherein one or two but not all of the carbon atoms of the acyclic $C_{1-8}$ hydrocarbon group may optionally be replaced by O, S, SO, $SO_2$, $NR^c$, $X^3C(X^4)$, $C(X^4)X^3$ or $X^3C(X^4)X^3$;

$R^6$ is selected from the substituents $R^5$ except that $R^6$ does not consist of or contain a carbocyclic or heterocyclic group;

$X^3$ is O, S or $NR^c$; and $X^4$ is =O, =S or =$NR^c$; and $R^c$ is hydrogen or $C_{1-4}$ hydrocarbyl;

$Ar^2$ is a bicyclic 8 to 11-membered heteroaryl group containing 1, 2, 3 or 4 heteroatom ring members selected from O, N and S and being optionally substituted with 1, 2 or 3 substituents $R^7$ selected from oxo, fluorine; chlorine; bromine; $C_{1-4}$ hydrocarbyl optionally substituted with one or more fluorine atoms; $C_{1-4}$ hydrocarbyloxy optionally substituted with one or more fluorine atoms; hydroxy; cyano; $N(R^c)_2$; $R^c$—C(O)—; $R^c$—C(O)N($R^c$)—; $(R^c)_2NC(O)$—; R—$SO_2NR^c$—; $R^c$—NHC(O)NH—; $(R^c)_2NSO_2$—; and five and six-membered monocyclic groups containing from 0 to 3 heteroatom ring members selected from O, N and S, the five and six-membered monocyclic groups being unsubstituted or substituted with one or more substituents $R^8$ selected from $C_{1-4}$ hydrocarbyl, $C_{1-4}$ hydrocarbyloxy, cyano, hydroxy, oxo, halogen, amino, mono-$C_{1-4}$ hydrocarbylamino and di-$C_{1-4}$hydrocarbylamino and wherein the hydrocarbyl moieties when present are optionally substituted with fluorine, $C_{1-2}$ alkoxy, hydroxy, amino, mono-di-$C_{1-2}$alkylamino or di-$C_{1-4}$alkylamino;

and wherein, in each substituent consisting of or containing a hydrocarbyl group, the hydrocarbyl group is selected from alkyl, alkenyl, alkynyl and cycloalkyl groups and combinations thereof.

Particular and preferred compounds of the formula (1) are as defined in the Embodiments 1.2 to 1.92 below.

1.2 A compound according to Embodiment 1.0 or 1.1 wherein Y is $Ar^2$ and Z is $R^3$.

1.3 A compound according to Embodiment 1.0 or 1.1 wherein Y is $R^3$ and Z is $Ar^2$.

1.4 A compound according to Embodiment 1.0 or 1.1 having the formula (2):

(2)

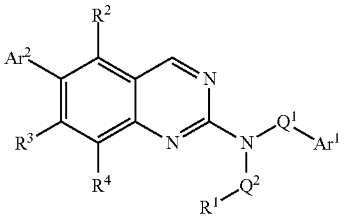

or a salt, tautomer or N-oxide thereof;

wherein $R^1$, $R^2$, $R^3$, $R^4$, $Ar^1$, $Ar^2$, $Q^1$ and $Q^2$ are all as defined in Embodiment 1.0 or 1.1.

1.4A A compound according to Embodiment 1.0 wherein $Q^1$ is a $C_{1-6}$ alkylene group optionally substituted by one or two substituents selected from hydroxy and $C_{1-4}$ hydrocarbyloxy, provided that when a hydroxy substituent is present, there are at least two carbon atoms between the hydroxy substituent and the nitrogen atom to which $Q^2$ is attached; and wherein a carbon atom of the $C_{1-6}$ alkylene group may optionally be replaced by a cyclopropane-1,1-diyl or cyclobutane-1,1-diyl group provided that the total number of carbon atoms in an alkylene group containing such a replacement does not exceed 6.

1.4B A compound according to Embodiment 1.4A wherein $Q^1$ is a $C_{1-5}$ alkylene group optionally substituted by one or two substituents selected from hydroxy and $C_{1-4}$ hydrocarbyloxy, provided that when a hydroxy substituent is present, there are at least two carbon atoms between the hydroxy substituent and the nitrogen atom to which $Q^2$ is attached; and wherein a carbon atom of the $C_{1-5}$ alkylene group may optionally be replaced by a cyclopropane-1,1-diyl or cyclobutane-1,1-diyl group provided that the total number of carbon atoms in an alkylene group containing such a replacement does not exceed 5.

1.4C A compound according to Embodiment 1.4B wherein $Q^1$ is a $C_{1-4}$ alkylene group optionally substituted by one or two substituents selected from hydroxy and $C_{1-4}$ hydrocarbyloxy, provided that when a hydroxy substituent is present, there are at least two carbon atoms between the hydroxy substituent and the nitrogen atom to which $Q^2$ is attached; and wherein a carbon atom of the $C_{1-4}$ alkylene group may optionally be replaced by a cyclopropane-1,1-diyl or cyclobutane-1,1-diyl group provided that the total number of carbon atoms in an alkylene group containing such a replacement does not exceed 4.

1.4D A compound according to Embodiment 1.4C wherein $Q^1$ is cyclopropane-1,1-diyl.

1.4E A compound according to Embodiment 1.4C wherein $Q^1$ is cyclobutane-1,1-diyl.

1.5 A compound according to any one of Embodiments 1.0 to 1.4 wherein $Q^1$ is $C_{1-6}$ alkylene optionally substituted by one or two substituents selected from hydroxy and $C_{1-4}$ hydrocarbyloxy, provided that when a hydroxy substituent is present, there are at least two carbon atoms between the hydroxy substituent and the nitrogen atom to which $Q^2$ is attached.

1.6 A compound according to Embodiment 1.5 wherein $Q^1$ is $C_{1-4}$ alkylene optionally substituted by one or two substituents selected from hydroxy and $C_{1-4}$ hydrocarbyloxy, provided that when a hydroxy substituent is present, there are at least two carbon atoms between the hydroxy substituent and the nitrogen atom to which $Q^2$ is attached.

1.7 A compound according to Embodiment 1.6 wherein the $C_{1-4}$ alkylene is optionally substituted by one hydroxy substituent, provided that there are at least two carbon atoms between the hydroxy substituent and the nitrogen atom to which $Q^2$ is attached.

1.8 A compound according to any one of Embodiments 1.0 to 1.4 wherein $Q^1$ is a group of the formula $-(CR^fR^g)_p-$ wherein p is 1 to 8, each $R^f$ is independently selected from hydrogen and methyl, and each $R^g$ is independently selected from hydrogen, $C_{1-4}$ alkyl and hydroxyl-$C_{1-4}$alkyl, provided that no more than one $R^G$ may be larger than methyl and provided that the total number of carbon atoms in $-(CR^fR^g)_p-$ does not exceed 8.

1.9 A compound according to Embodiment 1.8 wherein the total number of carbon atoms in $-(CR^fR^g)_p-$ is in the range 1 to 6.

1.10 A compound according to Embodiment 1.9 wherein the total number of carbon atoms in $-(CR^fR^g)_p-$ is in the range 1 to 4.

1.11 A compound according to any one of Embodiments 1.8 to 1.10 wherein p is 1 or 2.

1.12 A compound according to Embodiment 1.11 wherein p is 1.

1.13 A compound according to any one of Embodiments 1.8 to 1.12 wherein $R^f$ is hydrogen and $R^g$ is selected from hydrogen, methyl, ethyl, isopropyl and hydroxymethyl.

1.13A A compound according to any one of Embodiments 1.8 to 1.12 wherein $R^f$ is hydrogen and $R^g$ is selected from hydrogen, methyl, ethyl, isopropyl, hydroxymethyl and hydroxyethyl.

1.14 A compound according to Embodiment 1.13 wherein $Q^1$ is selected from $CH_2$, $CH(CH_3)$ and $CH(CH_2OH)$.

1.14A A compound according to Embodiment 1.13A wherein $Q^1$ is selected from $CH_2$, $CH(CH_3)$, $CH(CH_2OH)$ and $CH(CH_2CH_2OH)$.

1.15 A compound according to Embodiment 1.13 wherein $Q^1$ is $CH(CH_3)$.

1.16 A compound according to any one of Embodiments 1.0 to 1.4 wherein the moiety $-N(Q^2-R^1)-Q^1-Ar^1$ has the formula:

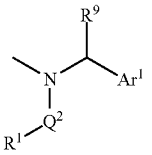

wherein $R^9$ is hydrogen or a $C_{1-4}$ alkyl optionally substituted with hydroxyl.

1.17 A compound according to any one of Embodiments 1.0 to 1.4 wherein the moiety $-(Q^2-R^1)N-Q^1-Ar^1$ has the formula:

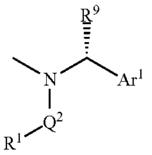

wherein $R^9$ is hydrogen or a $C_{1-4}$ alkyl optionally substituted with hydroxyl.

1.18 A compound according to Embodiment 1.16 or 1.17 wherein $R^9$ is hydrogen, methyl, ethyl, isopropyl or hydroxymethyl.

1.18A A compound according to Embodiment 1.16 or 1.17 wherein $R^9$ is hydrogen, methyl, ethyl, isopropyl, hydroxymethyl or hydroxyethyl.

1.19 A compound according to Embodiment 1.18 wherein $R^9$ is hydrogen, methyl or hydroxymethyl.

1.19A A compound according to Embodiment 1.18A wherein $R^9$ is hydrogen, methyl, hydroxymethyl or hydroxyethyl.

1.20 A compound according to Embodiment 1.18 wherein $R^9$ is hydrogen.

1.21 A compound according to Embodiment 1.18 wherein $R^9$ is methyl.

1.22 A compound according to Embodiment 1.18 wherein $R^9$ is hydroxymethyl.

1.22A A compound according to Embodiment 1.18 wherein $R^9$ is hydroxyethyl.

1.23 A compound according to any one of Embodiments 1.0 to 1.22 wherein $Q^2$ is a bond or $C_{1-6}$ alkylene.

1.24 A compound according to Embodiment 1.23 wherein $Q^2$ is a bond or $C_{1-3}$ alkylene.

1.25 A compound according to Embodiment 1.24 wherein $Q^2$ is selected from a bond, $CH_2$, $CH_2CH_2$ and $CH_2CH_2CH_2$.

1.26 A compound according to Embodiment 1.25 wherein $Q^2$ is a bond, $CH_2$, or $CH_2CH_2$.

1.27 A compound according to Embodiment 1.26 wherein $Q^2$ is a bond.

1.28 A compound according to Embodiment 1.26 wherein $Q^2$ is $CH_2$.

1.29 A compound according to any one of Embodiments 1.0 to 1.28 wherein $R^1$ is selected from hydrogen and a group $Cy^1$.

1.30 A compound according to Embodiment 1.29 wherein $R^1$ is hydrogen.

1.31 A compound according to Embodiment 1.29 wherein $R^1$ is a group $Cy^1$.

1.32 A compound according to any one of Embodiments 1.0 to 1.29 and 1.31 wherein $Cy^1$ is selected from $C_{3-7}$ cycloalkyl and C-linked 4 to 7 membered non-aromatic heterocyclic groups containing 1 or 2 heteroatom ring members selected from N, O and S, wherein the cycloalkyl and heterocyclic groups are optionally substituted with one or two substituents selected from $C_{1-3}$ hydrocarbyl, fluorine, oxo and hydroxy.

1.33 A compound according to Embodiment 1.32 wherein $Cy^1$ is selected from $C_{3-6}$ cycloalkyl and C-linked 4 to 6 membered non-aromatic heterocyclic groups containing 1 or 2 heteroatom ring members selected from O and S, wherein the cycloalkyl and heterocyclic groups are optionally substituted with one or two substituents selected from $C_{1-3}$ hydrocarbyl, fluorine, oxo and hydroxy.

1.34 A compound according to Embodiment 1.33 wherein $Cy^1$ is selected from $C_{3-6}$ cycloalkyl and C-linked 4 to 6 membered saturated non-aromatic heterocyclic groups containing 1 heteroatom ring member selected from O and S, wherein the cycloalkyl and heterocyclic groups are optionally substituted with one or two substituents selected from saturated $C_{1-3}$ hydrocarbyl, fluorine, oxo and hydroxy.

1.35 A compound according to Embodiment 1.33 wherein $Cy^1$ is selected from $C_{3-6}$ cycloalkyl and C-linked 4 to 6 membered saturated non-aromatic heterocyclic groups containing 1 heteroatom ring member selected from O, wherein the cycloalkyl and heterocyclic groups are optionally substituted with one or two substituents selected from $C_{1-3}$ alkyl, fluorine, oxo and hydroxy.

1.36 A compound according to Embodiment 1.33 wherein $Cy^1$ is selected from $C_{3-6}$ cycloalkyl and C-linked 4 to 6 membered saturated non-aromatic heterocyclic groups containing 1 heteroatom ring member selected from O, wherein the cycloalkyl and heterocyclic groups are unsubstituted or substituted with one or two substituents selected from methyl, fluorine, oxo and hydroxy.

1.37 A compound according to Embodiment 1.33 wherein $Cy^1$ is selected from cyclopropyl, cyclobutyl, cyclopentyl, cyclohexyl, tetrahydropyran and tetrahydrofuran.

1.38 A compound according to Embodiment 1.33 wherein $Cy^1$ is tetrahydropyran.

1.39 A compound according to Embodiment 1.32 wherein $Cy^1$ is selected from C-linked 4 to 7 membered non-aromatic heterocyclic groups containing a first ring member which is nitrogen and optionally a second ring member selected from N, O and S, wherein the heterocyclic groups are optionally substituted with one or two substituents selected from $C_{1-3}$ hydrocarbyl, fluorine, oxo and hydroxy.

1.40 A compound according to Embodiment 1.39 wherein $Cy^1$ is selected from C-linked 4 to 7 membered saturated heterocyclic groups containing a first ring member which is nitrogen and optionally a second ring member selected from N, O and S, wherein the heterocyclic groups are optionally substituted with one or two substituents selected from saturated $C_{1-3}$ hydrocarbyl, fluorine, oxo and hydroxy.

1.41 A compound according to Embodiment 1.40 wherein $Cy^1$ is selected from C-linked 4 to 7 membered saturated heterocyclic groups containing a first ring member which is nitrogen and optionally a second ring member selected from N, O and S, wherein the heterocyclic groups are optionally substituted with one or two substituents selected from $C_{1-3}$ alkyl, cyclopropyl, fluorine and hydroxy.

1.42 A compound according to Embodiment 1.41 wherein $Cy^1$ is selected from C-linked azetidine, pyrrolidine, piperidine, piperazine, morpholine, homomorpholine and thiomorpholine, each being optionally substituted with one or two substituents selected from $C_{1-3}$ alkyl, cyclopropyl, fluorine and hydroxy.

1.43 A compound according to Embodiment 1.41 wherein $Cy^1$ is C-linked morpholine.

1.44 A compound according to any one of Embodiments 1.0 to 1.28 wherein $R^1$ is $NR^xR^y$.

1.45 A compound according to any one of Embodiments 1.0 to 1.28 and 1.44 wherein $R^x$ and $R^y$ are the same or different and each is selected from hydrogen, $C_{1-4}$ hydrocarbyl or hydroxy-$C_{1-4}$ hydrocarbyl.

1.46 A compound according to Embodiment 1.45 wherein $R^x$ and $R^y$ are the same or different and each is selected from hydrogen, saturated $C_{1-4}$ hydrocarbyl or saturated hydroxy-$C_{1-4}$ hydrocarbyl.

1.47 A compound according to Embodiment 1.46 wherein $R^x$ and $R^y$ are the same or different and each is selected from hydrogen, $C_{1-4}$ alkyl, cyclopropyl, methylcyclopropyl, cyclopropylmethyl, and hydroxy-$C_{2-4}$ alkyl.

1.48 A compound according to Embodiment 1.47 wherein $R^x$ and $R^y$ are the same or different and each is selected from hydrogen and $C_{1-4}$ alkyl.

1.49 A compound according to Embodiment 1.48 wherein $R^x$ and $R^y$ are the same or different and each is selected from hydrogen and $C_{1-3}$ alkyl.

1.50 A compound according to Embodiment 1.49 wherein $NR^xR^y$ is selected from amino, methylamino and dimethylamino.

1.51 A compound according to Embodiment 1.49 wherein $NR^xR^y$ is dimethylamino.

1.52 A compound according to any one of Embodiments 1.0 to 1.28 and 1.44 wherein $NR^xR^y$ forms a 4 to 7-membered heterocyclic ring containing a total of 1 or 2 heteroatom ring members of which one is N and the other is selected from N, O and S and oxidised forms thereof, the heterocyclic ring being optionally substituted with one or two substituents selected from $C_{1-4}$ hydrocarbyl, oxo, amino, mono-$C_{1-4}$ hydrocarbylamino, di-$C_{1-4}$hydrocarbylamino, fluorine and hydroxy, provided that there are at least two carbon atoms in line between the amino, mono-$C_{1-4}$ hydrocarbylamino, di-$C_{1-4}$hydrocarbylamino and hydroxy substituents when present and the nitrogen atom of the $NR^xR^y$ group.

1.53 A compound according to Embodiment 1.52 wherein $NR^xR^y$ forms a 4 to 7-membered non-aromatic heterocyclic ring containing a total of 1 or 2 heteroatom ring members of which one is N and the other is selected from N, O and S, the heterocyclic ring being optionally substituted with one or two substituents selected from $C_{1-4}$ hydrocarbyl, oxo, amino, saturated mono-$C_{1-4}$ hydrocarbylamino, saturated di-$C_{1-4}$ hydrocarbylamino, fluorine and hydroxy, provided that there are at least two carbon atoms in line between the amino, saturated mono-$C_{1-4}$ hydrocarbylamino, saturated di-$C_{1-4}$ hydrocarbylamino and hydroxy substituents when present and the nitrogen atom of the $NR^xR^y$ group.

1.54 A compound according to Embodiment 1.53 wherein $NR^xR^y$ forms a saturated 4 to 7-membered heterocyclic ring containing a total of 1 or 2 heteroatom ring members of which one is N and the other is selected from N, O and S, the heterocyclic ring being optionally substituted with one or two substituents selected from $C_{1-4}$ alkyl, fluorine, oxo, amino, mono-$C_{1-4}$ alkylamino, di-$C_{1-4}$alkylamino and hydroxy.

1.55 A compound according to Embodiment 1.54 wherein $NR^xR^y$ forms a saturated 4 to 7-membered heterocyclic ring containing a total of 1 or 2 heteroatom ring members of which one is N and the other is selected from N, O and S, the heterocyclic ring being optionally substituted with one or two substituents selected from $C_{1-3}$ alkyl, fluorine oxo, amino, mono-$C_{1-2}$ alkylamino, di-$C_{1-2}$alkylamino and hydroxy.

1.56 A compound according to Embodiment 1.55 wherein $NR^xR^y$ forms a saturated 4 to 7-membered heterocyclic ring containing a total of 1 or 2 heteroatom ring members of which one is N and the other is selected from N, O and S, the heterocyclic ring being optionally substituted with one or two substituents selected from methyl, fluorine, oxo, amino, methylamino, dimethylamino and hydroxy.

1.57 A compound according to Embodiment 1.55 wherein $NR^xR^y$ forms a heterocyclic ring selected from azetidine, pyrrolidine, piperidine, piperazine, morpholine, homomorpholine and thiomorpholine, each being optionally substituted with one or two substituents selected from $C_{1-3}$ alkyl, fluorine and hydroxy.

1.57 A compound according to Embodiment 1.55 wherein $NR^xR^y$ forms a heterocyclic ring selected from azetidine, pyrrolidine, piperidine, piperazine, morpholine, homomorpholine and thiomorpholine, each being optionally substituted with one or two substituents selected from $C_{1-3}$ alkyl, fluorine and hydroxy.

1.57A A compound according to any one of Embodiments 1.0 to 1.28 wherein $R^1$ is selected from:

hydrogen;

a group $Cy^1$ wherein $Cy^1$ is selected from 4 to 7 membered saturated heterocyclic groups containing a first ring member which is nitrogen and optionally a second ring member selected from N, O and S, wherein the heterocyclic groups are optionally substituted with one or two substituents selected from $C_{1-3}$ alkyl, cyclopropyl, fluorine and hydroxyl; and $NR^xR^y$, wherein $R^x$ and $R^y$ are the same or different and each is selected from hydrogen, $C_{1-4}$ alkyl, cyclopropyl, methylcyclopropyl, cyclopropylmethyl, and hydroxy-$C_{2-4}$ alkyl.

1.58 A compound according to any one of Embodiments 1.0 to 1.57A wherein $R^2$ is selected from hydrogen, fluorine, chlorine, methyl, methoxy, trifluoromethyl and trifluoromethoxy.

1.59 A compound according to Embodiment 1.58 wherein $R^2$ is hydrogen.

1.60 A compound according to any one of Embodiments 1.0 to 1.59 wherein $R^3$ is selected from hydrogen, fluorine, chlorine, methyl, methoxy, trifluoromethyl and trifluoromethoxy.

1.61 A compound according to Embodiment 1.60 wherein $R^3$ is hydrogen.

1.62 A compound according to any one of Embodiments 1.0 to 1.61 wherein $R^4$ is selected from hydrogen, fluorine, chlorine, methyl, methoxy, trifluoromethyl and trifluoromethoxy.

1.63 A compound according to Embodiment 1.62 wherein $R^4$ is hydrogen.

1.64 A compound according to any one of Embodiments 1.0 to 1.63 wherein $Ar^1$ is a monocyclic aryl or heteroaryl ring selected from phenyl, furyl, thienyl, pyridyl and pyrimidinyl, each optionally substituted with 1, 2 or 3 substituents $R^5$ which are the same or different and are as defined in Embodiment 1.1.

1.65 A compound according to Embodiment 1.64 wherein $Ar^1$ is a monocyclic aryl or heteroaryl ring selected from phenyl, furyl, thienyl and pyridyl, each optionally substituted with 1, 2 or 3 substituents $R^5$ which are the same or different and are as defined in Embodiment 1.1.

1.66 A compound according to Embodiment 1.65 wherein $Ar^1$ is a phenyl ring optionally substituted with 1, 2 or 3 substituents $R^5$ which are the same or different and are as defined in Embodiment 1.1.

1.67 A compound according to any one of Embodiments 1.0 to 1.66 wherein $Ar^1$ is unsubstituted or substituted with 1, 2 or 3 substituents $R^5$ which are the same or different and are selected from fluorine, chlorine, bromine, cyano and a group $R^a$—$R^b$;

$R^a$ is a bond, O, CO, $NR^cC(=O)$, $C(=O)NR^c$, $NR^cC(=O)NR$, $C(=O)O$, $OC(=O)$, S, SO, $SO_2$, $NR^c$, $SO_2NR^c$ or $NR^cSO_2$;

$R^b$ is:

hydrogen;

a carbocyclic or heterocyclic group having from 3 to 7 ring members, of which 0, 1, 2 or 3 are heteroatom ring members selected from O, N and S and oxidised forms of S, the carbocyclic or heterocyclic group being optionally substituted with one or more substituents $R^6$; and an acyclic $C_{1-8}$ hydrocarbon group optionally substituted with one or more substituents selected from hydroxy; oxo; halogen; cyano; amino; mono- or di-$C_{1-4}$ alkylamino; and carbocyclic and heterocyclic groups having from 3 to 7 ring members, of which 0, 1, 2 or 3 are heteroatom ring members selected from O, N and S and oxidised forms of S, the carbocyclic or heterocyclic group being optionally substituted with one or more substituents $R^6$; wherein one or two but not all of the carbon atoms of the acyclic $C_{1-8}$ hydrocarbon group may optionally be replaced by O, S, SO, $SO_2$ or $NR^c$;

$R^6$ is selected from the substituents $R^5$ except that $R^6$ does not consist of or contain a carbocyclic or heterocyclic group; and $R^c$ is hydrogen or $C_{1-4}$ hydrocarbyl.

1.68 A compound according to Embodiment 1.67 wherein $Ar^1$ is unsubstituted or substituted with 1, 2 or 3 substituents $R^5$ which are the same or different and are selected from fluorine, chlorine, bromine, cyano and a group $R^a$—$R^b$;

$R^a$ is a bond, O, CO, $NR^cC(═O)$, $C(═O)NR^c$, $NR^cC(═O)NR$, C(═O) O, OC(═O), S, SO, $SO_2$, $NR^c$, $SO_2NR^c$ or $NR^cSO_2$;

$R^b$ is:

hydrogen;

a non-aromatic carbocyclic or heterocyclic group having from 3 to 6 ring members, of which 0, 1 or 2 are heteroatom ring members selected from O, N, S and $SO_2$, the non-aromatic carbocyclic or heterocyclic group being optionally substituted with one or more substituents $R^6$; and an acyclic $C_{1-8}$ hydrocarbon group optionally substituted with one or more substituents selected from hydroxy; oxo; halogen; cyano; amino; mono- or di-$C_{1-4}$ alkylamino; and non-aromatic carbocyclic and heterocyclic groups having from 3 to 6 ring members, of which 0, 1 or 2 are heteroatom ring members selected from O, N, S and $SO_2$, the carbocyclic or heterocyclic group being optionally substituted with one or more substituents $R^6$; wherein one or two but not all of the carbon atoms of the acyclic $C_{1-8}$ hydrocarbon group may optionally be replaced by O, S, SO, $SO_2$ or $NR^c$;

$R^6$ is selected from the substituents $R^5$ except that $R^6$ does not consist of or contain a carbocyclic or heterocyclic group; and $R^c$ is hydrogen or $C_{1-4}$ hydrocarbyl.

1.69 A compound according to Embodiment 1.68 wherein $Ar^1$ is unsubstituted or substituted with 1, 2 or 3 substituents $R^5$ which are the same or different and are selected from fluorine, chlorine, bromine, cyano and a group $R^a$—$R^b$;

$R^a$ is a bond, O, CO, $NR^cC(═O)$, $C(═O)NR^c$, $SO_2$, $NR^c$, $SO_2NR^c$ or $NR^cSO_2$;

$R^b$ is:

hydrogen;

a non-aromatic carbocyclic or heterocyclic group having from 3 to 6 ring members, of which 0, 1 or 2 are heteroatom ring members selected from O, N and S, the non-aromatic carbocyclic or heterocyclic group being optionally substituted with one or more substituents $R^6$; and a saturated acyclic $C_{1-8}$ hydrocarbon group optionally substituted with one or more substituents selected from hydroxy; oxo; fluorine; cyano; amino; mono- or di-$C_{1-2}$ alkylamino; and non-aromatic carbocyclic and heterocyclic groups having from 3 to 6 ring members, of which 0, 1 or 2 are heteroatom ring members selected from O, N and S and oxidised forms of S, the carbocyclic or heterocyclic group being optionally substituted with one or more substituents $R^6$; wherein one or two but not all of the carbon atoms of the acyclic $C_{1-8}$ hydrocarbon group may optionally be replaced by O or $NR^c$;

$R^6$ is selected from the substituents $R^5$ except that $R^6$ does not consist of or contain a carbocyclic or heterocyclic group; and $R^c$ is hydrogen, $C_{1-4}$ alkyl, cyclopropyl or cyclopropylmethyl.

1.70 A compound according to any one of Embodiments 1.0 to 1.66 wherein $Ar^1$ is unsubstituted or is substituted with 1, 2 or 3 substituents $R^5$ selected from a group $L^1$-$Cy^2$; fluorine; chlorine; bromine; $C_{1-3}$ alkyl; $C_{1-3}$ alkoxy; trifluoromethyl; difluoromethyl; hydroxy; cyano; trifluoromethoxy; difluoromethoxy; amino; mono-$C_{1-3}$ alkylamino; di-$C_{1-3}$ alkylamino; $C_{1-3}$ alkanoyl; $C_{1-3}$ alkanoylamino; carbamoyl; mono-$C_{1-3}$ alkyl carbamoyl; di-$C_{1-3}$ alkyl carbamoyl; a group O—$(CH_2)_k$—$OR^{10}$; and a group $O_m$—$(CH_2)_n$—$NR^{11}R^{12}$; $R^{10}$ is hydrogen or $C_{1-3}$ alkyl; $R^{11}$ is hydrogen or $C_{1-3}$ alkyl; $R^{12}$ is hydrogen or $C_{1-3}$ alkyl; k is 2, 3 or 4; m is 0 or 1; and n is 1, 2, 3 or 4 provided that when m is 1 then n is 2, 3 or 4; $L^1$ is a bond or a linker group selected from $C_{1-4}$ alkylene, —$(CH_2)_p$—NH—$(CH_2)_q$—, —$(CH_2)_p$—$N(CH_3)$—$(CH_2)_q$—, —$(CH_2)_p$—C(═O)—$(CH_2)_q$—, —$(CH_2)_p$—C(═O)NH—$(CH_2)_q$—, —$(CH_2)_p$—C(═O)$N(CH_3)$—$(CH_2)_q$—, —$(CH_2)_p$—NHC(═O)—$(CH_2)_q$— and —$(CH_2)_p$—$N(CH_3)C(═O)$—$(CH_2)_q$—; p and q are each independently 0, 1, 2 or 3 provided that the total of p and q does not exceed 4; and $Cy^2$ is a non-aromatic carbocyclic or heterocyclic ring of three to seven ring members, containing 0, 1 or 2 heteroatom ring members selected from O, N and S and being optionally substituted by one, two or three substituents selected from hydroxy, $C_{1-4}$ hydrocarbyl, $C_{1-4}$ hydrocarbyl-C(═O), oxo, amino, mono-$C_{1-4}$ hydrocarbylamino, di-$C_{1-4}$ hydrocarbylamino and fluorine.

1.70A A compound according to any one of Embodiments 1.0 to 1.66 wherein $Ar^1$ is unsubstituted or is substituted with 1, 2 or 3 substituents $R^5$ selected from a group $L^1$-$Cy^2$; fluorine; chlorine; bromine; $C_{1-3}$ alkyl; $C_{1-3}$ alkoxy; trifluoromethyl; difluoromethyl; hydroxy; cyano; trifluoromethoxy; difluoromethoxy; amino; mono-$C_{1-3}$ alkylamino; di-$C_{1-3}$ alkylamino; $C_{1-3}$ alkanoyl; $C_{1-3}$ alkylsulphonylamino; $C_{1-3}$ alkanoylamino; carbamoyl; mono-$C_{1-3}$ alkyl carbamoyl; di-$C_{1-3}$ alkyl carbamoyl; a group O—$(CH_2)_k$—$OR^{10}$; and a group $O_m$—$(CH_2)_n$—$NR^{11}R^{12}$; $R^{10}$ is hydrogen or $C_{1-3}$ alkyl; $R^{11}$ is hydrogen or $C_{1-3}$ alkyl; $R^{12}$ is hydrogen or $C_{1-3}$ alkyl; k is 2, 3 or 4; m is 0 or 1; and n is 1, 2, 3 or 4 provided that when m is 1 then n is 2, 3 or 4; $L^1$ is a bond or a linker group selected from $C_{1-4}$ alkylene, —$(CH_2)_p$—NH—$(CH_2)_q$—, —$(CH_2)_p$—$N(CH_3)$—$(CH_2)_q$—, —$(CH_2)_p$—C(═O)—$(CH_2)_q$—, —$(CH_2)_p$—C(═O)NH—$(CH_2)_q$—, —$(CH_2)_p$—C(═O)$N(CH_3)$—$(CH_2)_q$—, —$(CH_2)_p$—NHC(═O)—$(CH_2)_q$— and —$(CH_2)_p$—$N(CH_3)C(═O)$—$(CH_2)_q$—; p and q are each independently 0, 1, 2 or 3 provided that the total of p and q does not exceed 4; and $Cy^2$ is a non-aromatic carbocyclic or heterocyclic ring of three to seven ring members, containing 0, 1 or 2 heteroatom ring members selected from O, N and S and being optionally substituted by one, two or three substituents selected from hydroxy, $C_{1-4}$ hydrocarbyl, $C_{1-4}$ hydrocarbyl-C(═O), oxo, amino, mono-$C_{1-4}$ hydrocarbylamino, di-$C_{1-4}$ hydrocarbylamino and fluorine.

1.71 A compound according to Embodiment 1.70 wherein $Ar^1$ is unsubstituted or is substituted with 1, 2 or 3 substituents $R^5$ selected from a group $L^1$-$Cy^2$; fluorine; chlorine; bromine; $C_{1-3}$ alkyl; $C_{1-3}$ alkoxy; trifluoromethyl; difluoromethyl; hydroxy; cyano; trifluoromethoxy; difluoromethoxy; amino; mono-$C_{1-3}$ alkylamino; di-$C_{1-3}$ alkylamino; $C_{1-3}$ alkanoyl; $C_{1-3}$ alkanoylamino; carbamoyl; mono-$C_{1-3}$ alkyl carbamoyl; di-$C_{1-3}$ alkyl carbamoyl; a group O—$(CH_2)_k$—$OR^{10}$; and a group $O_m$—$(CH_2)_n$—$NR^{11}R^{12}$; $R^{10}$ is hydrogen, methyl or ethyl; $R^{11}$ is hydrogen, methyl or ethyl; $R^{12}$ is hydrogen, methyl; or ethyl; k is 2 or 3; m is 0 or 1; and n is 1, 2 or 3 provided that when m is 1 then n is 2 or 3; $L^1$ is a bond or a linker group selected from $C_{1-4}$ alkylene, —$(CH_2)_p$—NH—$(CH_2)_q$—, —$(CH_2)_p$—N($CH_3$)—$(CH_2)_q$—, —$(CH_2)_p$—C(═O)—$(CH_2)_q$—, —$(CH_2)_p$—C(═O)NH—$(CH_2)_q$—, —$(CH_2)_p$—C(═O)N($CH_3$)—$(CH_2)_q$—, —$(CH_2)_p$—NHC(═O)—$(CH_2)_q$— and —$(CH_2)_p$—N($CH_3$)C(═O)—$(CH_2)_q$—; p and q are each independently 0, 1 or 2; and $Cy^2$ is a non-aromatic carbocyclic ring of three to six ring members or a heterocyclic ring of five or six ring members, containing 1 or 2 heteroatom ring members selected from O, N and S, the carbocyclic and heterocyclic rings each being optionally substituted by one, two or three substituents selected from hydroxy, $C_{1-4}$ alkyl, cyclopropyl, cyclopropylmethyl, $C_{1-4}$ alkanoyl, cyclopropylcarbonyl, oxo and fluorine.

1.71A A compound according to Embodiment 1.70A wherein $Ar^1$ is unsubstituted or is substituted with 1, 2 or 3 substituents $R^5$ selected from a group $L^1$-$Cy^2$; fluorine; chlorine; bromine; $C_{1-3}$ alkyl; $C_{1-3}$ alkoxy; trifluoromethyl; difluoromethyl; hydroxy; cyano; trifluoromethoxy; difluoromethoxy; amino; mono-$C_{1-3}$ alkylamino; di-$C_{1-3}$ alkylamino; $C_{1-3}$ alkanoyl; $C_{1-3}$ alkylsulphonylamino; $C_{1-3}$ alkanoylamino; carbamoyl; mono-$C_{1-3}$ alkyl carbamoyl; di-$C_{1-3}$ alkyl carbamoyl; a group O—$(CH_2)_k$—$OR^{10}$; and a group $O_m$—$(CH_2)_n$—$NR^{11}R^{12}$; $R^{10}$ is hydrogen, methyl or ethyl; $R^{11}$ is hydrogen, methyl or ethyl; $R^{12}$ is hydrogen, methyl; or ethyl; k is 2 or 3; m is 0 or 1; and n is 1, 2 or 3 provided that when m is 1 then n is 2 or 3; $L^1$ is a bond or a linker group selected from $C_{1-4}$ alkylene, —$(CH_2)_p$—NH—$(CH_2)_q$—, —$(CH_2)_p$—N($CH_3$)—$(CH_2)_q$—, —$(CH_2)_p$—C(═O)—$(CH_2)_q$—, —$(CH_2)_p$—C(═O)NH—$(CH_2)_q$—, —$(CH_2)_p$—C(═O)N($CH_3$)—$(CH_2)_q$—, —$(CH_2)_p$—NHC(═O)—$(CH_2)_q$— and —$(CH_2)_p$—N($CH_3$)C(═O)—$(CH_2)_q$—; p and q are each independently 0, 1 or 2; and $Cy^2$ is a non-aromatic carbocyclic ring of three to six ring members or a heterocyclic ring of five or six ring members, containing 1 or 2 heteroatom ring members selected from O, N and S, the carbocyclic and heterocyclic rings each being optionally substituted by one, two or three substituents selected from hydroxy, $C_{1-4}$ alkyl, cyclopropyl, cyclopropylmethyl, $C_{1-4}$ alkanoyl, cyclopropylcarbonyl, oxo and fluorine.

1.72 A compound according to Embodiment 1.71 wherein $Ar^1$ is unsubstituted or is substituted with 1, 2 or 3 substituents $R^5$ selected from a group $L^1$-$Cy^2$; fluorine; chlorine; bromine; $C_{1-3}$ alkyl; $C_{1-3}$ alkoxy; trifluoromethyl; difluoromethyl; hydroxy; cyano; trifluoromethoxy; difluoromethoxy; amino; mono-$C_{1-2}$ alkylamino; di-$C_{1-2}$ alkylamino; $C_{1-3}$ alkanoyl; $C_{2-3}$ alkanoylamino; carbamoyl; mono-$C_{1-3}$ alkyl carbamoyl; di-$C_{1-3}$ alkyl carbamoyl; a group O—$(CH_2)_k$—$OR^{10}$; and a group $O_m$—$(CH_2)_n$—$NR^{11}R^{12}$; $R^{10}$ is hydrogen, methyl or ethyl; $R^{11}$ is hydrogen, methyl or ethyl; $R^{12}$ is hydrogen, methyl; or ethyl; k is 2 or 3; m is 0 or 1; and n is 1, 2 or 3 provided that when m is 1 then n is 2 or 3; $L^1$ is a bond or a linker group selected from $C_{1-4}$ alkylene, —$(CH_2)_p$—NH—$(CH_2)_q$—, —$(CH_2)_p$—N($CH_3$)—$(CH_2)_q$—, —$(CH_2)_p$—C(═O)—$(CH_2)_q$—, —$(CH_2)_p$—C(═O)NH—$(CH_2)_q$—, —$(CH_2)_p$—C(═O)N($CH_3$)—$(CH_2)_q$—, —$(CH_2)_p$—NHC(═O)—$(CH_2)_q$— and —$(CH_2)_p$—N($CH_3$)C(═O)—$(CH_2)_q$—; p and q are each independently 0 or 1; and $Cy^2$ is a non-aromatic heterocyclic ring selected from azetidine, pyrrolidine, piperidine, piperazine, morpholine, thiomorpholine, tetrahydrofuran, and tetrahydropyran, the heterocyclic ring being optionally substituted by one or two substituents selected from hydroxy, $C_{1-4}$ alkyl, cyclopropyl, cyclopropylmethyl, $C_{1-4}$ alkanoyl, cyclopropylcarbonyl, oxo and fluorine.

1.72A A compound according to Embodiment 1.71A wherein $Ar^1$ is unsubstituted or is substituted with 1, 2 or 3 substituents $R^5$ selected from a group $L^1$-$Cy^2$; fluorine; chlorine; bromine; $C_{1-3}$ alkyl; $C_{1-3}$ alkoxy; trifluoromethyl; difluoromethyl; hydroxy; cyano; trifluoromethoxy; difluoromethoxy; amino; mono-$C_{1-2}$ alkylamino; di-$C_{1-2}$ alkylamino; $C_{1-3}$ alkanoyl; $C_{1-2}$ alkylsulphonylamino; $C_{2-3}$ alkanoylamino; carbamoyl; mono-$C_{1-3}$ alkyl carbamoyl; di-$C_{1-3}$ alkyl carbamoyl; a group O—$(CH_2)_k$—$OR^{10}$; and a group $O_m$—$(CH_2)_n$—$NR^{11}R^{12}$; $R^{10}$ is hydrogen, methyl or ethyl; $R^{11}$ is hydrogen, methyl or ethyl; $R^{12}$ is hydrogen, methyl; or ethyl; k is 2 or 3; m is 0 or 1; and n is 1, 2 or 3 provided that when m is 1 then n is 2 or 3; $L^1$ is a bond or a linker group selected from $C_{1-4}$ alkylene, —$(CH_2)_p$—NH—$(CH_2)_q$—, —$(CH_2)_p$—N($CH_3$)—$(CH_2)_q$—, —$(CH_2)_p$—C(═O)—$(CH_2)_q$—, —$(CH_2)_p$—C(═O)NH—$(CH_2)_q$—, —$(CH_2)_p$—C(═O)N($CH_3$)—$(CH_2)_q$—, —$(CH_2)_p$—NHC(═O)—$(CH_2)_q$— and —$(CH_2)_p$—N($CH_3$)C(═O)—$(CH_2)_q$—; p and q are each independently 0 or 1; and $Cy^2$ is a non-aromatic heterocyclic ring selected from azetidine, pyrrolidine, piperidine, piperazine, morpholine, thiomorpholine, tetrahydrofuran, and tetrahydropyran, the heterocyclic ring being optionally substituted by one or two substituents selected from hydroxy, $C_{1-4}$ alkyl, cyclopropyl, cyclopropylmethyl, $C_{1-4}$ alkanoyl, cyclopropylcarbonyl, oxo and fluorine.

1.73 A compound according to Embodiment 1.72 wherein $Ar^1$ is unsubstituted or is substituted with 1, 2 or 3 substituents $R^5$ selected from a group $L^1$-$Cy^2$; fluorine; chlorine; bromine; $C_{1-2}$ alkyl; $C_{1-2}$ alkoxy; trifluoromethyl; difluoromethyl; hydroxy; cyano; trifluoromethoxy; difluoromethoxy; amino; mono-$C_{1-2}$ alkylamino; di-$C_{1-2}$ alkylamino; acetyl; acetylamino; carbamoyl; mono-$C_{1-2}$ alkyl carbamoyl; di-$C_{1-2}$ alkyl carbamoyl; dimethylaminoethoxy; wherein $L_1$ is selected from a bond, O, NH, N($CH_3$), NHC(═O), C(═O)NH, N($CH_3$)C(═O) and C(═O)N($CH_3$); and $Cy^2$ is selected from piperidine, piperazine, morpholine and tetrahydropyran, the heterocyclic ring being optionally substituted by one or two substituents selected from hydroxy, methyl and oxo.

1.73A A compound according to Embodiment 1.72A wherein $Ar^1$ is unsubstituted or is substituted with 1, 2 or 3 substituents $R^5$ selected from a group $L^1$-$Cy^2$; fluorine; chlorine; bromine; $C_{1-2}$ alkyl; $C_{1-2}$ alkoxy; trifluoromethyl; difluoromethyl; hydroxy; cyano; trifluoromethoxy; difluoromethoxy; $C_{1-2}$ alkylsulphonylamino; amino; mono-$C_{1-2}$ alkylamino; di-$C_{1-2}$ alkylamino; acetyl; acetylamino; carbamoyl; mono-$C_{1-2}$ alkyl carbamoyl; di-$C_{1-2}$ alkyl carbamoyl; dimethylaminoethoxy; wherein $L_1$ is selected from a bond, O, NH, N($CH_3$), NHC(═O), C(═O)NH, N($CH_3$)C(═O) and C(═O)N($CH_3$); and $Cy^2$ is selected from piperidine, piperazine, morpholine and tetrahydropyran, the heterocyclic ring being optionally substituted by one or two substituents selected from hydroxy, methyl and oxo.

1.74 A compound according to Embodiment 1.73 wherein $Ar^1$ is unsubstituted or substituted with 1, 2 or 3 substituents $R^5$ selected from fluorine, chlorine, bromine, methyl, hydroxy, methoxy, trifluoromethyl, difluoromethyl, cyano, trifluoromethoxy, difluoromethoxy, morpholinyl, piperazinyl, N-methylpiperazinyl and dimethylaminoethoxy.

1.74A A compound according to Embodiment 1.73A wherein $Ar^1$ is unsubstituted or substituted with 1, 2 or 3 substituents $R^5$ selected from fluorine, chlorine, bromine, methyl, hydroxy, methoxy, trifluoromethyl, difluoromethyl, cyano, trifluoromethoxy, difluoromethoxy, methylsulphonylamino, morpholinyl, piperazinyl, N-methylpiperazinyl and dimethylaminoethoxy.

1.75 A compound according to any one of Embodiments 1.0 to 1.66 wherein $Ar^1$ is unsubstituted or substituted with 1, 2 or 3 substituents $R^5$ selected from $L^1$-$Cy^2$; fluorine, chlorine, methyl, hydroxy, methoxy, trifluoromethyl, difluoromethyl, trifluoromethoxy and dimethylaminoethoxy; wherein $L_1$ is selected from a bond, 0, NH, NHC(═O), C(═O)NH and C(═O)N($CH_3$); and $Cy^2$ is selected from piperidine, piperazine, morpholine and tetrahydropyran, the heterocyclic ring being optionally substituted by one or two substituents selected from methyl and oxo.

1.75A A compound according to any one of Embodiments 1.0 to 1.66 wherein $Ar^1$ is unsubstituted or substituted with 1, 2 or 3 substituents $R^5$ selected from $L^1$-$Cy^2$; fluorine, chlorine, methyl, hydroxy, methoxy, trifluoromethyl, difluoromethyl, trifluoromethoxy, methylsulphonylamino and dimethylaminoethoxy; wherein $L_1$ is selected from a bond, 0, NH, NHC(═O), C(═O)NH and C(═O)N($CH_3$); and $Cy^2$ is selected from piperidine, piperazine, morpholine and tetrahydropyran, the heterocyclic ring being optionally substituted by one or two substituents selected from methyl and oxo.

1.76 A compound according to Embodiment 1.75 wherein $Ar^1$ is unsubstituted or substituted with 1, 2 or 3 substituents $R^5$ selected from fluorine, chlorine, bromine, methyl, methoxy, trifluoromethyl, difluoromethyl, cyano, trifluoromethoxy and difluoromethoxy.

1.76A A compound according to Embodiment 1.75A wherein $Ar^1$ is unsubstituted or substituted with 1, 2 or 3 substituents $R^5$ selected from fluorine, chlorine, bromine, methyl, hydroxyl, methoxy, methylsulphonylamino, trifluoromethyl, difluoromethyl, cyano, trifluoromethoxy and difluoromethoxy.

1.77 A compound according to Embodiment 1.76 wherein $Ar^1$ is unsubstituted or substituted with 1, 2 or 3 substituents $R^5$ selected from fluorine, chlorine, methyl, methoxy, trifluoromethyl and trifluoromethoxy.

1.77A A compound according to Embodiment 1.76A wherein $Ar^1$ is unsubstituted or substituted with 1, 2 or 3 substituents $R^5$ selected from fluorine, chlorine, methyl, hydroxyl, methoxy, methylsulphonylamino, trifluoromethyl and trifluoromethoxy.

1.78 A compound according to Embodiment 1.77 wherein $Ar^1$ is unsubstituted or substituted with 1, 2 or 3 substituents $R^5$ selected from fluorine, chlorine, methyl and methoxy.

1.78A A compound according to Embodiment 1.77A wherein $Ar^1$ is unsubstituted or substituted with 1, 2 or 3 substituents $R^5$ selected from fluorine, chlorine, methylsulphonylamino, methyl and methoxy.

1.79 A compound according to Embodiment 1.78 wherein $Ar^1$ is unsubstituted or substituted with 1, 2 or 3 substituents $R^5$ selected from fluorine, chlorine and methoxy.

1.80 A compound according to any one of Embodiments 1.0 to 1.79 wherein $Ar^1$ is unsubstituted or substituted with one or two substituents $R^5$.

1.81 A compound according to Embodiment 1.80 wherein $Ar^1$ is unsubstituted or substituted with one substituent $R^5$.

1.82 A compound according to Embodiment 1.81 wherein $Ar^1$ is unsubstituted.

1.83 A compound according to Embodiment 1.81 wherein $Ar^1$ is substituted with one substituent $R^5$.

1.84 A compound according to Embodiment 1.80 wherein $Ar^1$ is a phenyl ring which is unsubstituted or is substituted with one or two substituents $R^5$ wherein at least one substituent $R^5$ is present at the meta- or para-position of the phenyl ring.

1.85 A compound according to Embodiment 1.84 wherein $Ar^1$ is a phenyl ring which is substituted with one substituent $R^5$ which is present at the meta-position of the phenyl ring.

1.86 A compound according to Embodiment 1.84 wherein $Ar^1$ is a phenyl ring which is substituted with one substituent $R^5$ which is present at the para-position of the phenyl ring.

1.87 A compound according to Embodiment 1.84 wherein $Ar^1$ is a phenyl ring which is unsubstituted or is substituted with one substituent $R^5$ selected from 3-chloro, 4-chloro, 3-fluoro, 4-fluoro, 3-methoxy, 4-methoxy, 3-methyl and 4-methyl.

1.88 A compound according to Embodiment 1.87 wherein $Ar^1$ is a phenyl ring which is unsubstituted or is substituted with one substituent $R^5$ selected from 3-chloro, 3-fluoro, 4-fluoro and 3-methoxy.

1.89 A compound according to Embodiment 1.84 wherein $Ar^1$ is a phenyl ring which is substituted with two substituents $R^5$.

1.90 A compound according to Embodiment 1.89 wherein $Ar^1$ is a phenyl ring which is substituted with two substituents $R^5$, wherein one substituent is present at the para-position of the phenyl ring and the other is present at the meta-substituent of the phenyl ring.

1.91 A compound according to Embodiment 1.90 wherein $Ar^1$ is 3,4-difluorophenyl.

1.91A A compound according to Embodiment 1.82 wherein $Ar^1$ is unsubstituted phenyl.

1.91B A compound according to Embodiment 1.66 wherein $Ar^1$ is unsubstituted phenyl or phenyl substituted with one or two substituents selected from fluorine, chlorine, methoxy, methylsulphonylamino and hydroxyl.

1.91C A compound according to Embodiment 1.66 wherein $Ar^1$ is unsubstituted phenyl or phenyl substituted with one or two substituents selected from fluorine, chlorine, methoxy and methylsulphonylamino.

1.91D A compound according to Embodiment 1.66 wherein $Ar^1$ is selected from unsubstituted phenyl, 3-chlorophenyl, 2-fluorophenyl, 3-fluorophenyl, 4-fluorophenyl, 2,4-difluorophenyl, 2,6-difluorophenyl, 3,4-difluorophenyl, 3-methoxyphenyl, 3-methylsulphonylaminophenyl, 2-hydroxyphenyl, 3-hydroxyphenyl and 4-hydroxyphenyl.

1.91E A compound according to Embodiment 1.66 wherein $Ar^1$ is selected from unsubstituted phenyl, 3-chlorophenyl, 2-fluorophenyl, 3-fluorophenyl, 4-fluorophenyl, 2,4-difluorophenyl, 2,6-difluorophenyl, 3,4-difluorophenyl, 3-methoxyphenyl, 3-methylsulphonylaminophenyl, 2-hydroxyphenyl, 3-hydroxyphenyl and 4-hydroxyphenyl 1.92 A compound according to any one of Embodiments 1.0 to 1.91 wherein $Ar^2$ is selected from 5.6 fused heteroaromatic rings and 6.6 fused heteroaromatic rings, each containing 1, 2, 3 or 4 heteroatom ring members selected from N, O and S and being optionally substituted by 1, 2, or 3 substituents $R^7$ as defined in Embodiment 1.1.

1.93 A compound according to Embodiment 1.92 wherein the 5.6 fused heteroaromatic rings and 6.6 fused heteroaromatic rings each contain 1, 2, 3 or 4 nitrogen heteroatom ring members.

1.94 A compound according to Embodiment 1.92 or 1.93 wherein $Ar^2$ is selected from 5.6 fused heteroaromatic rings, each being optionally substituted by 1, 2 or 3 substituents $R^7$ as defined in Embodiment 1.1.

1.95 A compound according to Embodiment 1.94 wherein $Ar^2$ is selected from pyrimido-imidazole, pyrido-imidazole, pyrimido-pyrrole, pyrido-pyrrole, benzo-imidazole, benzo-pyrrole, pyrimido-pyrazole, pyrido-pyrazole and benzo-pyrazole groups, each being optionally substituted by 1, 2 or 3 substituents $R^7$ as defined in Embodiment 1.1.

1.95A A compound according to Embodiment 1.95 wherein $Ar^2$ is selected from pyrimido-pyrrole, pyrido-pyrrole, pyrimido-pyrazole, pyrido-pyrazole groups and pyrimido-imidazole groups, each optionally substituted by 1, 2 or 3 substituents $R^7$ as defined in Embodiment 1.1.

1.96 A compound according to Embodiment 1.95 wherein $Ar^2$ is selected from pyrimido-pyrrole, pyrido-pyrrole, pyrimido-pyrazole and pyrido-pyrazole groups, each optionally substituted by 1, 2 or 3 substituents $R^7$ as defined in Embodiment 1.1.

1.97 A compound according to Embodiment 1.96 wherein $Ar^2$ is a pyrimido-pyrazole group, which is optionally substituted by 1, 2 or 3 substituents $R^7$ as defined in Embodiment 1.1.

1.98 A compound as defined in any one of Embodiments 1.0 to 1.97 wherein $Ar^2$ is unsubstituted or is substituted with one or two substituents $R^7$ selected from oxo, fluorine; chlorine; bromine; $C_{1-4}$ hydrocarbyl optionally substituted with one or more fluorine atoms; $C_{1-4}$ hydrocarbyloxy optionally substituted with one or more fluorine atoms; hydroxy; cyano; and five and six-membered monocyclic groups containing from 0 to 3 heteroatom ring members selected from O, N and S, the five and six-membered monocyclic groups being unsubstituted or substituted with one or more substituents $R^8$ selected from $C_{1-4}$ hydrocarbyl, $C_{1-4}$ hydrocarbyloxy, cyano, hydroxy, oxo, halogen, amino, mono-$C_{1-4}$ hydrocarbylamino and di-$C_{1-4}$hydrocarbylamino.

1.99 A compound as defined in Embodiment 1.98 wherein $Ar^2$ is unsubstituted or is substituted with one or two substituents $R^7$ selected from oxo, fluorine; chlorine; bromine; $C_{1-4}$ alkyl optionally substituted with one or more fluorine atoms; $C_{1-4}$ alkoxy optionally substituted with one or more fluorine atoms; hydroxy; cyano; and five and six-membered monocyclic groups selected from phenyl, pyridyl, pyrimidinyl, pyridazinyl, pyrazinyl, pyrrole, pyrazole, imidazole, thiophene, furan, oxazole and isoxazole, the five and six-membered monocyclic groups each being unsubstituted or substituted with one or more substituents $R^8$ selected from $C_{1-4}$ alkyl, $C_{1-4}$ alkoxy, cyano, hydroxy, fluorine, chlorine, amino, methylamino and dimethylamino.

1.100 A compound as defined in Embodiment 1.99 wherein $Ar^2$ is unsubstituted or is substituted with one or two substituents $R^7$ selected from oxo, fluorine; chlorine; bromine; $C_{1-4}$ alkyl optionally substituted with one or more fluorine atoms; $C_{1-4}$ alkoxy optionally substituted with one or more fluorine atoms; hydroxy and cyano.

1.101 A compound as defined in Embodiment 1.100 wherein $Ar^2$ is unsubstituted or is substituted with one or two substituents $R^7$ selected from oxo, methyl, difluoromethyl, trifluoromethyl, amino, hydroxy and cyano.

1.102 A compound as defined in any one of Embodiments 1.0 to 1.101 wherein $Ar^2$ is unsubstituted or is monosubstituted.

1.103 A compound as defined in Embodiment 1.102 wherein $Ar^2$ is unsubstituted or is mono-substituted with one substituent $R^7$ selected from methyl and amino.

1.103AA compound as defined in Embodiment 1.102 wherein $Ar^2$ is unsubstituted or is mono-substituted with one substituent $R^7$ selected from methyl and cyano.

1.104 A compound as defined in Embodiment 1.103 wherein $Ar^2$ is unsubstituted or is substituted with one substituent $R^7$ which is methyl.

1.105 A compound as defined in Embodiment 1.104 wherein $Ar^2$ is unsubstituted.

1.106 A compound as defined in any one of Embodiments 1.0 to 1.105 wherein $Ar^2$ is:

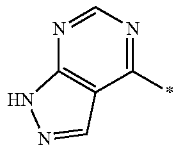 [SMILES: *c1ncnc2[nH]ncc12]

where * denotes the point of attachment to the quinazoline ring.

1.107 A compound of the formula (3):

(3)

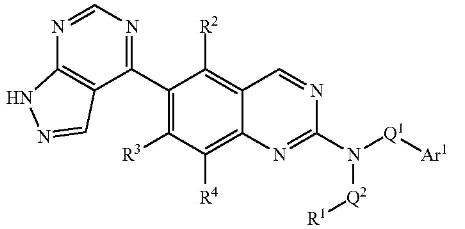

or a salt, tautomer or N-oxide thereof, wherein $R^1$, $R^2$, $R^3$, $R^4$, $Q^1$, $Q^2$ and $Ar^1$ are as defined in any one of Embodiments 1.0 to 1.106.

1.108 A compound of the formula (4):

(4)

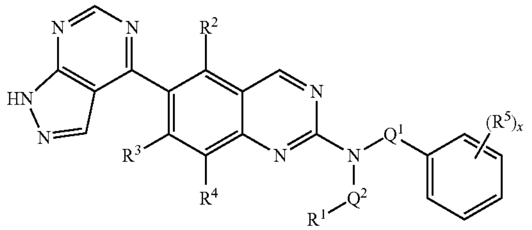

or a salt, tautomer or N-oxide thereof, wherein $R^1$, $R^2$, $R^3$, $R^4$, $R^5$, $Q^1$ and $Q^2$ are as defined in any one of Embodiments 1.0 to 1.106; and x is 0, 1 or 2.

1.109 A compound according to Embodiment 1.108 wherein $Q^1$ is $CH_2$ or $CH(CH_3)$, $Q^2$ is a bond or $CH_2$ and $R^1$ is hydrogen.

1.110 A compound according to Embodiment 1.108 or Embodiment 1.109 wherein x is 0 or 1.

1.111 A compound selected from the title compounds of Examples 1 to 43 herein.

1.112 A compound according to any one of Embodiments 1.0 to 1.111 which is in the form of a salt.

1.113 A compound according to Embodiment 1.112 wherein the salt is an acid addition salt.

1.114 A compound according to Embodiment 1.112 or Embodiment 1.113 wherein the salt is a pharmaceutically acceptable salt.

1.115 A compound according to any one of Embodiments 1.0 to 1.114 which is in the form of a solvate.

1.116 A compound according to Embodiment 1.115 wherein the solvate is a hydrate.

Definitions

References to "carbocyclic" and "heterocyclic" groups as used herein shall, unless the context indicates otherwise, include both aromatic and non-aromatic ring systems. Thus, for example, the term "carbocyclic and heterocyclic groups" includes within its scope aromatic, non-aromatic, unsaturated, partially saturated and fully saturated carbocyclic and heterocyclic ring systems.

The carbocyclic or heterocyclic groups can be aryl or heteroaryl groups. The aryl or heteroaryl groups can be monocyclic or bicyclic groups, as defined herein. The term "aryl" as used herein refers to a carbocyclic group having aromatic character and the term "heteroaryl" is used herein to denote a heterocyclic group having aromatic character. Where the context permits, the terms "aryl" and "heteroaryl" may embrace bicyclic ring systems wherein both rings are aromatic or one ring is non-aromatic and the other is aromatic. In such bicyclic systems containing one aromatic and one non-aromatic group, the group may be attached by the aromatic ring, or by the non-aromatic ring.

The term 'C-linked' (for example as in "C-linked 4 to 7 membered monocyclic non-aromatic or carbocyclic or heterocyclic group") refers to a group as herein defined where the point of attachment is through a carbon atom.

In formula (1), $Ar^1$ is a monocyclic 5 or 6-membered aryl or heteroaryl ring containing 0, 1 or 2 heteroatom ring members selected from O, N and S. Examples of such rings include but are not limited to pyrrole, furan, thiophene, imidazole, oxazole, isoxazole, thiazole, isothiazole, pyrazole, pyridine, pyrazine, pyridazine, pyrimidine and phenyl groups.

The aryl or heteroaryl ring $Ar^1$ can be substituted with a substituent that consists of or includes a 3- to 7-membered carbocyclic or heterocyclic group. The carbocyclic or heterocyclic groups can be aryl or heteroaryl groups as defined above, or they can be non-aromatic groups.

The term "non-aromatic group" refers to unsaturated ring systems without aromatic character, partially saturated and fully saturated carbocyclic and heterocyclic ring systems. The terms "unsaturated" and "partially saturated" refer to rings wherein the ring structure(s) contains atoms sharing more than one valence bond e.g. the ring contains at least one multiple bond e.g. a C═C N═C bond. The term "saturated" refers to rings where there are no multiple bonds between ring atoms. Saturated carbocyclic groups include the cycloalkyl groups cyclopropyl, cyclobutyl, cyclopentyl, cyclohexyl and cycloheptyl. Partially saturated carbocyclic groups include the cycloalkenyl groups cyclopentenyl, cyclohexenyl, cycloheptenyl and cyclooctenyl. Non-aromatic heterocyclic groups include azetidine, pyrrolidine, piperidine, azepane, piperazine, morpholine, thiomorpholine, thiomorpholine S-oxide and S,S-dioxide, pyran (2H-pyran or 4H-pyran), dihydrothiophene, dihydropyran, dihydrofuran, dihydrothiazole, tetrahydrofuran, tetrahydrothiophene, dioxane, tetrahydropyran, imidazoline, imidazolidinone, oxazoline, thiazoline, pyrazoline, pyrazolidine.

In formula (1), $Ar^2$ is a bicyclic 8- to 11-membered heteroaryl group containing 1, 2, 3 or 4 heteroatom ring members selected from O, N and S. bicyclic heteroaryl group may be, for example, a group selected from a benzene ring fused to a 5- or 6-membered ring containing 1, 2 or 3 ring heteroatoms; a pyridine ring fused to a 5- or 6-membered ring containing 1, 2 or 3 ring heteroatoms; a pyrimidine ring fused to a 5- or 6-membered ring containing 1 or 2 ring heteroatoms; a pyrrole ring fused to a 5- or 6-membered ring containing 1, 2 or 3 ring heteroatoms; pyrazole ring fused to a 5- or 6-membered ring containing 1 or 2 ring heteroatoms; an imidazole ring fused to a 5- or 6-membered ring containing 1 or 2 ring heteroatoms; an oxazole ring fused to a 5- or 6-membered ring containing 1 or 2 ring heteroatoms; an isoxazole ring fused to a 5- or 6-membered ring containing 1 or 2 ring heteroatoms; a thiazole ring fused to a 5- or 6-membered ring containing 1 or 2 ring heteroatoms; an isothiazole ring fused to a 5- or 6-membered ring containing 1 or 2 ring heteroatoms; a thiophene ring fused to a 5- or 6-membered ring containing 1, 2 or 3 ring heteroatoms; a furan ring fused to a 5- or 6-membered ring containing 1, 2 or 3 ring heteroatoms; a cyclohexyl ring fused to a 5- or 6-membered ring containing 1, 2 or 3 ring heteroatoms; and a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole). Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole and pyrazolopyridine (e.g. pyrazolo[1,5-a]pyridine) groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

The term "hydrocarbyl" as used herein refers to aliphatic, alicyclic and aromatic groups having an all-carbon backbone and consisting of carbon and hydrogen atoms, except where otherwise stated. Examples of hydrocarbyl groups include alkyl, cycloalkyl, cycloalkenyl, carbocyclic aryl, alkenyl, alkynyl, cycloalkylalkyl, cycloalkenylalkyl, and carbocyclic aralkyl, aralkenyl and aralkynyl groups. Such groups can be unsubstituted or, where stated, substituted by one or more substituents as defined herein. In certain cases, as defined herein, one or more, but not all, of the carbon atoms of the hydrocarbyl group may be replaced by another atom or group of atoms.

The term "alkylene" (e.g. as in $C_{1-4}$ straight chain or branched chain alkylene) as used herein refers to an alkanediyl group, i.e. a divalent saturated acyclic straight chain or branched chain hydrocarbon group. Examples of straight chain alkylene groups include methylene ($CH_2$), ethylene ($CH_2CH_2$) and propylene (($CH_2CH_2CH_2$). Examples of branched chain alkylene groups include $CH(CH_3)$, $CH_2CH(CH_3)CH_2$ and $CH_2(CH_3)CH_2CH_2$.

Salts

The compounds of the invention as defined in Embodiments 1.0 to 1.111 may be presented in the form of salts.

The salts referred to above (and also defined in embodiments 1.112, 1.113 and 1.114) are typically acid addition salts.

The salts can be synthesized from the parent compound by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free base form of the compound with the acid in water or in an organic solvent, or in a mixture of the two;

generally, nonaqueous media such as ether, ethyl acetate, ethanol, isopropanol, or acetonitrile are used.

Acid addition salts (as defined in Embodiment 1.113) may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, (+)-L-lactic, (±)-DL-lactic, lactobionic, maleic, malic, (−)-L-malic, malonic, (±)-DL-mandelic, methanesulphonic, naphthalene-2-sulphonic, naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, p-toluenesulphonic, undecylenic and valeric acids, as well as acylated amino acids and cation exchange resins.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci*., Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

N-Oxides

Many compounds of the Embodiments 1.0 to 1.116 may form N-oxides. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry, by Jerry March, 4$^{th}$* Edition, Wiley Interscience, pages. More particularly, N-oxides can be made by the procedure of L. W. Deady (*Syn. Comm*. 1977, 7, 509-514) in which the amine compound is reacted with m-chloroperoxybenzoic acid (MCPBA), for example, in an inert solvent such as dichloromethane.

Further examples of conditions for forming N-oxides are disclosed in our earlier application WO2008/139152.

Geometric Isomers and Tautomers

The compounds of the invention may exist in a number of different geometric isomeric, and tautomeric forms and references to the compounds of formula (1) as defined in Embodiments 1.0 to 1.116 include all such forms. For the avoidance of doubt, where a compound can exist in one of several geometric isomeric or tautomeric forms and only one is specifically described or shown, all others are nevertheless embraced by formula (1) or subgroups, subsets, preferences and examples thereof.

Optical Isomers

Where compounds of the formula contain one or more chiral centres, and can exist in the form of two or more optical isomers, references to the compounds include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and—isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.,* 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the invention exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound having one or more chiral centres, wherein at least 55% (e.g. at least 60%, 65%, 70%, 75%, 80%, 85%, 90% or 95%) of the compound of the formula (1) is present as a single optical isomer (e.g. enantiomer or diastereoisomer). In one general embodiment, 99% or more (e.g. substantially all) of the total amount of the compound of the formula (1) may be present as a single optical isomer (e.g. enantiomer or diastereoisomer).

Isotopes

The compounds of the invention as defined in any one of Embodiments 1.0 to 1.116 may contain one or more isotopic substitutions, and a reference to a particular element includes within its scope all isotopes of the element. For example, a reference to hydrogen includes within its scope $^{1}H$, $^{2}H$ (D), and $^{3}H$ (T). Similarly, references to carbon and oxygen include within their scope respectively $^{12}C$, $^{13}C$ and $^{14}C$ and $^{16}O$ and $^{18}O$.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Solvates

Compounds of the formula (1) as defined in any one of Embodiments 1.0 to 1.116 may form solvates.

Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulphoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates.

Particularly preferred solvates are hydrates, and examples of hydrates include hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Prodrugs

The compounds of the formula (1) as defined in any one of Embodiments 1.0 to 1.116 may be presented in the form of a pro-drug.

By "prodrugs" is meant for example any compound that is converted in vivo into a biologically active compound of the formula (1), as defined in any one of Embodiments 1.0 to 1.116.

For example, some prodrugs are esters of the active compound (e.g., a physiologically acceptable metabolically labile ester). During metabolism, the ester group (—C(═O)OR) is cleaved to yield the active drug. Such esters may be formed by esterification, for example, of any hydroxyl groups present in the parent compound with, where appropriate, prior protection of any other reactive groups present in the parent compound, followed by deprotection if required.

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Complexes and Clathrates

Also encompassed by formula (1) or subgroups, subsets, preferences and examples thereof are complexes (e.g. inclusion complexes or clathrates with compounds such as cyclodextrins, or complexes with metals) of the compounds.

Biological Activity

Compounds of the formula (1) as defined in any one of Embodiments 1.0 to 1.116 have activity as inhibitors of p70S6 kinase. As such, they may be useful in preventing or treating disease states and conditions in which p70S6 kinase or mutant forms thereof play an active part.

For example, it is envisaged that the compounds of Embodiments 1.0 to 1.116 will be useful in treating a range of proliferative disorders such as cancers.

Accordingly, in further embodiments (Embodiments 2.1 to 2.9), the invention provides:

2.1 A compound of the formula (1) as defined in any one of Embodiments 1.0 to 1.116 for use in medicine or therapy.

2.2 A compound of the formula (1) as defined in any one of Embodiments 1.0 to 1.116 for use in preventing or treating disease states and conditions mediated by p70S6 kinase or mutant forms thereof.

2.3 A compound of the formula (1) as defined in any one of Embodiments 1.0 to 1.116 for use in preventing or treating disease states and conditions characterised by abnormal expression of p70S6 kinase (e.g. over-expression or expression of a mutant form of p70S6 kinase).

2.4 A compound of the formula (1) as defined in any one of Embodiments 1.0 to 1.116 for use as an anti-cancer agent.

2.5 The use of a compound of the formula (1) as defined in any one of Embodiments 1.0 to 1.116 for the manufacture of a medicament for the treatment of cancer.

2.6 A method of treating a cancer, which method comprises administering to a subject in need thereof a therapeutically effective amount of a compound of the formula (1) as defined in any one of Embodiments 1.0 to 1.116, optionally together with another anti-cancer agent or radiation therapy.

2.7 A compound of the formula (1) as defined in any one of Embodiments 1.0 to 1.116 for use in enhancing a therapeutic effect of radiation therapy or chemotherapy in the treatment of a proliferative disease such as cancer.

2.8 The use of a compound of the formula (1) as defined in any one of Embodiments 1.0 to 1.116 for the manufacture of a medicament for enhancing a therapeutic effect of radiation therapy or chemotherapy in the treatment of a proliferative disease such as cancer.

2.9 A method for the prophylaxis or treatment of a proliferative disease such as cancer, which method comprises administering to a patient in combination with radiotherapy or chemotherapy a compound of the formula (1) as defined in any one of Embodiments 1.0 to 1.116.

Examples of proliferative disorders (e.g. cancers) as defined in Embodiments 2.4 to 2.9 include, but are not limited to carcinomas, for example carcinomas of the bladder, breast, colon, kidney, epidermis, liver, lung, oesophagus, gall bladder, ovary, pancreas, stomach, cervix, thyroid, prostate, gastrointestinal system, or skin, hematopoieitic tumours such as leukaemia, B-cell lymphoma, T-cell lymphoma, Hodgkin's lymphoma, non-Hodgkin's lymphoma, hairy cell lymphoma, or Burkett's lymphoma; hematopoieitic tumours of myeloid lineage, for example acute and chronic myelogenous leukaemias, myelodysplastic syndrome, or promyelocytic leukaemia; thyroid follicular cancer; tumours of mesenchymal origin, for example fibrosarcoma or rhabdomyosarcoma; tumours of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

One particular subset of cancers against which the compounds of Embodiments 1.0 to 1.116 should prove particularly active are cancers which are characterised by P70S6 overexpression or elevated expression of P70S6 or the presence of mutant forms of P70S6 or elevated levels of activated (phosphorylated) p70S6K.

The ability of the compounds of the invention to inhibit P70S6 kinase can be determined by means of the protocols set out in the Examples section below.

Further particular examples of cancers against which the compounds of Embodiments 1.0 to 1.116 should prove particularly active are:

- Breast Cancer (over expression is linked to poor prognosis and metastasis (see Mol. Can. Ther, 2010, 9, 1180), particularly triple negative breast cancer
- Diffuse large B-cell lymphoma: (see Expert Opin Ther Targets. 2009 September; 13(9):1085-93.)
- Glioblastoma multiforme (associated with increased levels of P70S6K (see J Clin Oncol. 2005 Aug. 10; 23(23):5294-304))
- Human colorectal cancer (in which the mtor pathway & p70S6K are highly activated (see Ann. Surg. Oncol. 2009 September; 16(9):2617-28. Epub 2009 Jun. 11))

Another subset of cancers against which the compounds of Embodiments 1.0 to 1.116 should prove particularly active includes:

- breast cancer
- glioblastoma multiforme;
- adenocarcinomas of the colon;
- non-small cell lung cancer;
- small-cell lung cancer;
- cisplatin-resistant small-cell lung cancer;
- ovarian cancer;
- leukemia;

- pancreatic cancer;
- prostate cancer;
- mammary carcinoma;
- renal cell carcinoma;
- multiple myeloma;
- Kaposi's sarcoma;
- Hodgkin's lymphoma;
- lymphangioeiomyomatosis; and
- non-Hodgkin's lymphoma or sarcoma A further sub-set of cancers against which the compounds of Embodiments 1.0 to 1.116 should prove particularly active includes cancers of the brain such as:

- brain metastases from Triple-Negative Breast Cancer; and
- gliomas and glioblastomas.

Triple-Negative Breast Cancer

The majority of breast cancers are hormone-positive breast cancers, wherein the growth of cancer cells is stimulated by exposure to oestrogen and/or progesterone. Patients suffering from such cancers are typically treated with therapeutic agents that prevent or reduce the formation of oestrogen in the body or prevent oestrogen from binding to the cell and stimulating growth. Examples of such therapeutive agents include selective estrogen-receptor response modulators (SERMs) such as tamoxifen and toremifene; aromatase inhibitors such as anastrozole, exemestane and letrozole; oestrogen-receptor downregulators (ERDs) such as fulvestrant; and luteinizing hormone-releasing hormone agents (LHRHs) such as goserelin, leuprolide), and triptorelin. The stimulation of progesterone on hormone-positive cancer cells is affected by estrogen receptor activity; therefore, if estrogen exposure is reduced, progesterone sensitivity is often also affected.

Approximately one quarter of breast cancers are HER2-positive breast cancers which are characterised by overexpression of human epidermal growth factor receptor 2 (HER2). HER2-positive cancers are typically treated with therapeutic agents (e.g. Herceptin) that target the receptor to slow growth and replication.

There are however some breast cancers that are not oestrogen- or progesterone-positive and do not overexpress HER2 to a level that would characterise them as HER2-positive. Such forms of breast cancer are commonly referred to as triple-negative breast cancers. Patients with triple-negative breast cancer have fewer treatment options than patients with either hormone-positive or HER2-positive disease, and hence are generally more difficult to treat than oestrogen-positive, progesterone-positive and HER2-positive cancers. Triple negative breast cancers are also recognised as being more likely to spread (metastasize) to the brain. Patients with brain metastases are typically considered to be incurable with standard treatment approaches.

The compounds of formula (1) as defined in Embodiments 1.0 to 1.116 herein may be used in the treatment of triple negative breast cancer and the treatment of brain metastases arising from triple negative breast cancer. The compounds may also be used in the treatment of brain metastases arising from other forms of cancer.

Furthermore, the compounds of formula (1) as defined in Embodiments 1.0 to 1.116 herein may be used in the prevention or treatment of metastases in general, for example in the prevention or treatment of metastases in the brain, lung, liver, pancreas, kidney, bladder and gallbladder.

Accordingly, in further Embodiments 2.10 to 2.18, the invention provides:

2.10 A compound as defined in any one of Embodiments 1.0 to 1.116 for use in the treatment of triple negative breast cancers.

2.11 A compound as defined in any one of Embodiments 1.0 to 1.116 for use in the prevention or treatment of metastases, for example metastases in the brain, bones, lung, liver, pancreas, kidney, bladder and gallbladder, e.g. brain metastases arising from triple negative breast cancers.

2.12 A compound as defined in any one of Embodiments 1.0 to 1.116 for use in the treatment of brain metastases arising from non-brain cancers.

2.13 The use of a compound as defined in any one of Embodiments 1.0 to 1.116 for the manufacture of a medicament for the treatment of triple negative breast cancers.

2.14 The use of a compound as defined in any one of Embodiments 1.0 to 1.116 for the manufacture of a medicament for the prevention or treatment of metastases, for example metastases in the brain, bones, lung, liver, pancreas, kidney, bladder and gallbladder, e.g. brain metastases arising from triple negative breast cancers.

2.15 The use of a compound as defined in any one of Embodiments 1.0 to 1.116 for the manufacture of a medicament for the treatment of brain metastases arising from non-brain cancers.

2.16 A method of treating a triple negative breast cancer in a subject (e.g. a human subject) in need thereof, which method comprises administering to the subject a therapeutically effective amount of a compound as defined in any one of Embodiments 1.0 to 1.116.

2.17 A method of preventing or treating metastases, for example metastases in the brain, bones, lung, liver, pancreas, kidney, bladder and gallbladder (e.g. brain metastases arising from triple negative breast cancers), in a subject (e.g. a human subject) in need thereof, which method comprises administering to the subject a therapeutically effective amount of a compound as defined in any one of Embodiments 1.0 to 1.116.

2.18 A method of treating brain metastases arising from non-brain cancers in a subject (e.g. a human subject) in need thereof, which method comprises administering to the subject a therapeutically effective amount of a compound as defined in any one of Embodiments 1.0 to 1.116.

Gliomas

It is envisaged that the compounds of formula (1) as defined in Embodiments 1.0 to 1.116 herein will be useful in the treatment of gliomas on account of their potency as inhibitors of S6K1 (which is known to have a role in glial transformation) and their ability to reach the site of action, i.e. the brain.

Gliomas are a common type of primary brain tumour that originate in the glial cells in the brain, and account for about 30% of all primary brain and central nervous system tumours, and about 80% of all malignant brain tumours. Gliomas typically arise from three different types of cells that are normally found in the brain, namely astrocytes, oligodendrocytes, and ependymal cells. Major types of gliomas include ependymomas (associated with ependymal cells), astrocytomas (associated with astrocytes), oligodendrogliomas (associated with oligodendrocytes), brainstem glioma (which develops in the brain stem), optic nerve glioma (which develops in or around the optic nerve) and mixed gliomas (which contain cells from different types of glia).

An ependymoma is a type of glioma that develops from ependymal cells, usually in the lining of the ventricles of the brain or in the spinal cord. In children, they are most commonly found near the cerebellum. Ependymomas are rare, accounting for only about 2-3% of primary brain tumours. However, they account for about 8-10% of brain tumours in children and occur most often in children younger than 10 years of age.

Astrocytomas originate in the star-shaped glial cells (astrocytes) in the cerebrum. Astrocytomas do not usually spread outside the brain and spinal cord and do not usually affect other organs but they are the most common glioma and can occur in most parts of the brain and occasionally in the spinal cord. Two broad classes of astrocytoma are generally recognised, namely those with narrow zones of infiltration (mostly invasive tumours; e.g., pilocytic astrocytoma, subependymal giant cell astrocytoma, pleomorphic xanthoastrocytoma), that often are clearly outlined on diagnostic images; and those with diffuse zones of infiltration (e.g., high-grade astrocytoma, anaplastic astrocytoma, glioblastoma). Glioblastoma multiforme is a malignant astrocytoma and the most common primary brain tumour among adult humans.

An oligodendrogliomas is a type of glioma that develops from oliogodendrocytes, which are the supportive tissue cells of the brain, and are usually found in the cerebrum. About 4% of primary brain tumours are oliogodendrogliomas and they are most common in young and middle-aged adults. Seizures are a very common symptom of these gliomas, as well as headache, weakness, or changes in behavior or sleepiness.

Brain stem gliomas, as the name suggests, are tumours found in the brain stem. Most brain stem tumours cannot be surgically removed because of the remote location and delicate and complex function this area controls. Brain stem gliomas occur almost exclusively in children, typically in school-age children.

A mixed glioma is a malignant glioma made up of more than one type of glial cell. This type of glioma may also be referred to as an oligoastrocytoma. Mixed gliomas are often found in the cerebrum, but may metastasize to other parts of the brain. Only about 1% of primary brain tumours are mixed gliomas and they are most commonly found in adult men.

An optic nerve glioma is a type of malignant glioma (brain tumour) found in the optic chiasm. Optic nerve gliomas often surround the optic nerves, and are frequently found in people who have neurofibromatosis. A person suffering from an optic nerve glioma typically experiences loss of vision, and may also suffer from hormone disturbances as the tumours are often found at the base of the brain where the structures responsible for hormonal control are located. Optic nerve gliomas are typically difficult to treat because of the sensitivity of the surrounding brain structures.

In addition to being classified according to the type of glial cell from which they originate or the region of the brain in which they develop, gliomas can also be classified according to their "grade", which is a measure of the growth potential and aggressiveness of the tumour.

Thus, gliomas are most often referred to as "low-grade" or "high-grade" gliomas, the grade being determined by pathological evaluation of the tumour. Tumours can be further graded according to the World Health Organization (WHO) grading system, under which tumours are graded from I (least advanced disease—best prognosis) to IV (most advanced disease—worst prognosis).

Gliomas can also be classified according to whether they are located above or below the tentorium membrane which tentorium separates the cerebrum (above) region of the brain from the cerebellum (below). Supratentorial gliomas (i.e. tumours located above the tentorium in the cerebrum), are mostly found in adults (70%), whereas infratentorial gliomas (tumours located below the tentorium, in the cerebellum) are found mostly in children (70%).

A further class of gliomas consists of those tumours found in the pons of the brainstem. The brainstem has three parts (pons, midbrain and medulla); the pons controls critical functions such as breathing, making surgery on pontine gliomas extremely dangerous.

Accordingly, in further Embodiments 2.19 to 2.34, the invention provides:

2.19 A compound as defined in any one of Embodiments 1.0 to 1.116 for use in the treatment of gliomas and glioblastomas.

2.20 A compound for use according to Embodiment 2.19 wherein the glioma is an ependymoma.

2.21 A compound for use according to Embodiment 2.19 wherein the glioma is an astrocytoma.

2.22 A compound for use according to Embodiment 2.19 wherein the glioma is a glioblastoma.

2.23 A compound for use according to Embodiment 2.19 wherein the glioma is glioblastoma multiforme.

2.24 A compound for use according to Embodiment 2.19 wherein the glioma is an oligodendroglioma.

2.25 A compound for use according to Embodiment 2.19 wherein the glioma is a brainstem glioma.

2.26 A compound for use according to Embodiment 2.19 wherein the glioma is an optic nerve glioma.

2.27 A compound for use according to Embodiment 2.19 wherein the glioma is a mixed glioma.

2.28 A compound for use according to Embodiment 2.19 wherein the glioma is a low-grade glioma.

2.29 A compound for use according to Embodiment 2.19 wherein the glioma is a high-grade glioma.

2.30 A compound for use according to Embodiment 2.19 wherein the glioma is a supratentorial glioma.

2.31 A compound for use according to Embodiment 2.19 wherein the glioma is an infratentorial glioma.

2.32 A compound for use according to Embodiment 2.19 wherein the glioma is a pontine glioma.

2.33 The use of a compound as defined in any one of Embodiments 1.0 to 1.116 for the manufacture of a medicament for the treatment of a glioma as defined in any one of Embodiments 2.19 to 2.32.

2.34 A method of treating a glioma as defined in any one of Embodiments 2.19 to 2.32 in a subject in need thereof, which method comprises administering to the subject an effective therapeutic amount of a compound as defined in any one of Embodiments 2.19 to 2.32.

Neurodevelopmental Diseases and Neurodegenerative Diseases

As discussed above, P70S6K also has a crucial role in the pathology of a number of neurodevelopmental diseases and neurodegenerative disorders and diseases and it is envisaged that the inhibition of P70S6K will provide a means of treating many such diseases. Accordingly, in further embodiments 2.35 to 2.48, the invention provides:

2.35 A compound as defined in any one of Embodiments 1.0 to 1.116 for use in the treatment of a neurodevelopmental disorder.

2.36 A compound for use according to Embodiment 2.35 wherein the neurodevelopmental disorder is Fragile X Syndrome.

2.37 A compound for use according to Embodiment 2.35 wherein the neurodevelopmental disorder is Autism or an Autism Spectrum Disorder.

2.38 A compound for use according to Embodiment 2.35 wherein the neurodevelopmental disorder is Fragile X-associated tremor/ataxia syndrome (FXTAS).

2.39 A compound for use according to Embodiment 2.35 wherein the neurodevelopmental disorder is Angleman's syndrome.

2.40 A compound for use according to Embodiment 2.35 wherein the neurodevelopmental disorder is Tuberous sclerosis complex.

2.41 A compound for use according to Embodiment 2.35 wherein the neurodevelopmental disorder is MECP2 duplication syndrome.

2.42 A compound for use according to Embodiment 2.35 wherein the neurodevelopmental disorder is Down Syndrome.

2.43 A compound as defined in any one of Embodiments 1.0 to 1.116 for use in the treatment of a neurodegenerative disease.

2.44 A compound for use according to Embodiment 2.43 wherein the neurodegenerative disease is Alzheimer's disease.

2.45 A compound for use according to Embodiment 2.43 wherein the neurodegenerative disease is Huntington's disease.

2.46 A compound for use according to Embodiment 2.43 wherein the neurodegenerative disease is Parkinson's disease.

2.47 The use of a compound of the formula (1) as defined in any one of Embodiments 1.0 to 1.116 for the manufacture of a medicament for the treatment of a brain disorder, e.g. a brain disorder as defined in any one of Embodiments 2.35 to 2.46.

2.48 A method of treating a brain disorder (e.g. a brain disorder as defined in any one of Embodiments 2.35 to 2.46) in a subject (e.g. a mammalian subject such as a human), which method comprises administering to the subject a therapeutically effective amount of a compound of the formula (1), (2), (3) or (4) as defined in any one of Embodiments 1.0 to 1.116.

Fragile X syndrome usually manifests first in childhood. A delay in speech is common and is often the first symptom that brings the child to medical attention (around the age of two or three). Accordingly, in further embodiments, the invention provides:

2.48A A compound according to any one of Embodiments 1.0 to 1.116 for use in the treatment of Fragile X syndrome in a patient under the age of 20, for example under the age of 15, or under the age of 12, or under the age of 10, preferably below the age of 8, and even more preferably under the age of 5.

2.48B A method for the treatment of Fragile X syndrome which method comprises administering a patient in need thereof a compound as defined in any one of Embodiments 1.0 to 1.116, wherein the patient is under the age of 20, for example under the age of 15, or under the age of 12, or under the age of 10, preferably below the age of 8, and even more preferably under the age of 5.

2.48C The use of a compound as defined in any one of Embodiments 1.0 to 1.116 for the manufacture of a medicament for the treatment or prophylaxis of Fragile X syndrome in a patient under the age of 20, for example under the age of 15, or under the age of 12, or under the age of 10, preferably below the age of 8, and, even more preferably under the age of 5.

Other Diseases and Conditions in which S6K1 May be Implicated

As discussed above, P70S6K inhibitors may also be useful in the treatment of PTEN hamartoma syndrome, neurofibromatosis type 1 and lymphangioleiomyomatosis (LAM). Accordingly, in further embodiments (Embodiments 2.49 to 2.52), the invention provides:

2.49 A compound as defined in any one of Embodiments 1.0 to 1.116 for use in the treatment of a condition which is PTEN hamartoma syndrome.

2.50 A compound as defined in any one of Embodiments 1.0 to 1.116 for use in the treatment of a condition which is neurofibromatosis type 1.

2.51 A compound as defined in any one of Embodiments 1.0 to 1.116 for use in the treatment of a condition which is lymphangioleiomyomatosis.

2.52 The use of a compound as defined in any one of Embodiments 1.0 to 1.116 for the manufacture of a medicament for the treatment of a condition as defined in any one of Embodiments 2.49 to 2.51.

2.53 A method of treating a condition as defined in any one of Embodiments 2.49 to 2.51 in a subject (e.g. a mammalian subject such as a human), which method comprises administering to the subject a therapeutically effective amount of a compound of the formula (1), (2), (3) or (4) as defined in any one of Embodiments 1.0 to 1.116.

Determination of Biological Properties

The ability of the compounds of Embodiments 1.0 to 1.116 to inhibit cell proliferation can also be determined using the protocols set out in the Examples section below.

One advantage of compounds of Embodiments 1.0 to 1.116 is that they are selective kinase inhibitors.

Preferred compounds of Embodiments 1.0 to 1.116 are those having an $IC_{50}$ against p70S6 kinase of less than 5 μM, or less than 1 μM and preferably less than 0.1 μM.

For example, compounds of Embodiments 1.0 to 1.116 are selective inhibitors of p70S6 kinase compared to activity against Akt2 kinase. Preferred compounds of Embodiments 1.0 to 1.116 are at least 5 fold more active against p70S6 kinase than they are against Akt2 kinase, and more preferred compounds of Embodiments 1.0 to 1.116 are at least 10 fold or at least 20 fold more active against p70S6 kinase than they are against Akt2 kinase. Particularly preferred compounds of Embodiments 1.0 to 1.116 are at least 100 fold more active against p70S6 kinase than they are against Akt2 kinase.

Furthermore, compounds of Embodiments 1.0 to 1.116 are selective inhibitors of p70S6 kinase compared to activity against Aurora kinase. Preferred compounds of Embodiments 1.0 to 1.116 are at least 5 fold more active against p70S6 kinase than they are against Aurora A and/or B kinase, and more preferred compounds of Embodiments 1.0 to 1.116 are at least 10 fold more active against p70S6 kinase than they are against Aurora A and/or B kinase.

Compounds of Embodiments 1.0 to 1.116 having greater selectivity for p70S6 kinase versus Aurora A and/or Aurora B kinase and/or Akt kinase are expected to exhibit improved side effect profiles in relation to side effects arising from Aurora kinase and Akt kinase inhibition. For example, in the case of inhibition of Aurora kinases, neutropenia is a well known side effect in the clinic.

Accordingly, in further embodiments (Embodiments 2.54 to 2.57), the invention provides:

2.54 A compound according to any one of Embodiments 1.0 to 1.116 having an $IC_{50}$ against p70S6 kinase of less than 5 μM.

2.55 A compound according to any one of Embodiments 1.0 to 1.116 having an $IC_{50}$ against p70S6 kinase of or less than 1 μM.

2.56 A compound according to any one of Embodiments 1.0 to 1.116 having an $IC_{50}$ against p70S6 kinase of less than 0.1 μM.

2.57 A compound according to any one of Embodiments 2.54 to 2.56 for use in a therapy, treatment, method or use according to any one of Embodiments 2.1 to 2.52.

Many compounds defined in Embodiments 1.0 to 1.116 have good brain penetration and therefore are useful in treating brain disorders in which inhibition of p70S6 kinase is therapeutically effective.

The brain penetrating ability of the compounds of Embodiments 1.0 to 1.116 can be determined by means of an in vivo cassette mouse model which is an industry-standard means of assessing brain penetration of small molecules (see for example "In vitro permeability analysis, pharmacokinetic and brain distribution study in mice of imperatorin, isoimperatorin and cnidilin in Radix Angelicae Dahuricae", Fitoterapia, Volume 85, March 2013, Pages 144-153).

Methods for the Preparation of Compounds of the Invention

The invention also provides methods for the preparation of a compound of the formula (1).

Accordingly, in another embodiment (Embodiment 3.1), the invention provides a method for preparing a compound as defined in any one of Embodiments 1.0 to 1.116 wherein Y is $R^3$ and Z is $Ar^2$, which method comprises:

(a) the reaction of a compound of the formula (8):

(8)

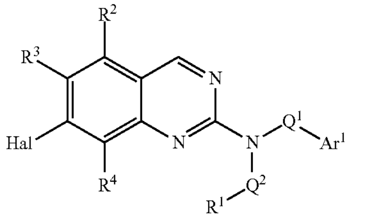

or a protected form thereof, wherein Hal is a halogen such as bromine, with a boronic acid or boronate reagent of the formula $Ar^2$—Bor where Bor is a boronate or boronic acid residue, in the presence of a palladium catalyst; and thereafter optionally removing any protecting group present; or (b) the reaction of a compound of the formula (9):

(9)

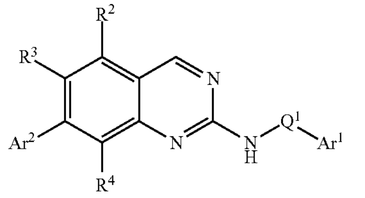

or a protected form thereof, with a compound of the formula LG-$Q^2$-$R^1$ where LG is a leaving group such as a halogen; and thereafter optionally removing any protecting group present.

In another embodiment (Embodiment 3.2), the invention provides a method for preparing a compound as defined in any one of Embodiments 1.0 to 1.116 wherein Y is $Ar^2$ and Z is $R^3$, which method comprises:

(a) the reaction of a compound of the formula (10):

(10)

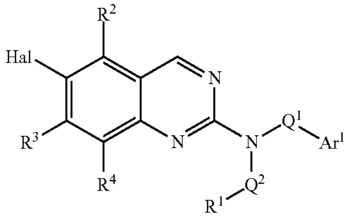

or a protected form thereof, wherein Hal is a halogen such as bromine, with a boronic acid or boronate reagent of the formula $Ar^2$—Bor where Bor is a boronate or boronic acid residue, in the presence of a palladium catalyst; and thereafter optionally removing any protecting group present; or (b) the reaction of a compound of the formula (11):

(11)

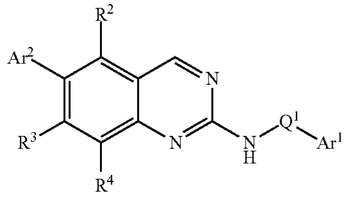

or a protected form thereof, with a compound of the formula LG-$Q^2$-$R^1$ where LG is a leaving group such as a halogen; and thereafter optionally removing any protecting group present.

Reaction (a) in Embodiments 3.1 and 3.2 above may be carried out under Suzuki coupling conditions, in the presence of a palladium catalyst such as bis(tri-t-butylphosphine)palladium (0) and a base (e.g. a carbonate such as potassium carbonate or caesium carbonate). The reaction may be carried out in a polar solvent such as dimethyl formamide (DMF) or dioxane, and the reaction mixture is typically subjected to heating, for example to a temperature in excess of 100° C.

Reaction (b) in Embodiments 3.1 and 3.2 above is typically carried out at room temperature in a polar solvent such as dimethyl sulphoxide or dimethyl formamide in the presence of a non-nucleophilic base such as an alkali metal hydride (e.g. sodium hydride).

Illustrative reaction schemes for the preparation of compounds of the formula (1) are set out below.

Scheme 1

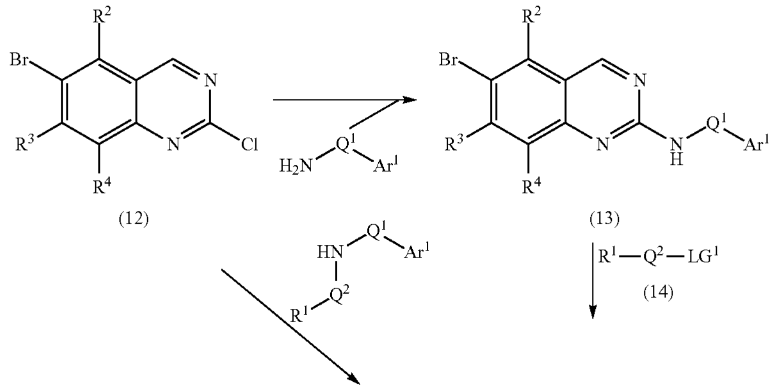

(12) (13) (14)

-continued

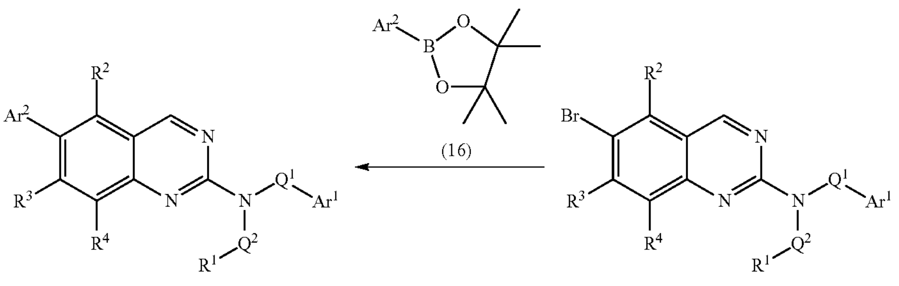

(1)

(15)

In Scheme 1, when $R^2$, $R^3$ and $R^4$ are hydrogen the starting material is the 6-bromo-2-chloro-quinazoline (12) which is commercially available. The 6-bromo-2-chloro-quinazoline (12) is reacted with the aryl- or heteroarylalkylamine $H_2N$-$Q^1$-$Ar^1$ in a polar solvent such as dimethylsulphoxide, typically at room temperature or optionally with mild heating, to give the intermediate compound (13). The compound (13) is reacted with sodium hydride in dimethylformamide at a reduced temperature of around 0° C. and a compound of formula (14), wherein $LG^1$ is a suitable leaving group (e.g. halogen, methanesulphonate or tosylate), is then added to the resulting reaction mixture. The reaction mixture may then be heated to a mild temperature of around 50° C. to give the bromo-intermediate (15).

Alternatively, the bromo-intermediate (15) can be synthesised directly from the 6-bromo-2-chloro-quinazoline starting material (12) by reacting with amine $NH(Q^1Ar^1)(Q^2R^1)$ in a polar solvent such as dimethylsulphoxide, typically at room temperature or optionally with mild heating.

The bromo-intermediate (15) is then reacted with the heteroaryl boronate (16) in a polar solvent such as dioxane in the presence of bis(tri-tert-butylphosphine)palladium (0) and caesum or potassium carbonate and optionally in the presence of potassium iodide under Suzuki reaction conditions to give the compound of formula (1) or a protected derivative thereof. The heteroaryl group $Ar^2$ may be present in the boronate compound (16) in a protected form. For example, when $Ar^2$ contains an NH group, a protecting group such as a Boc (tert-butoxycarbonyl) group may be attached to the nitrogen atom, replacing the hydrogen atom. After the reaction between the boronate compound (16) and the intermediate (15), a deprotection step may be required in order to give the compound of formula (1). In the case of a Boc protecting group, this can be removed by treatment with an acid such as hydrochloric acid.

Boronates and boronic acids of the formula $Ar^2$—Bor are widely available commercially or can be prepared for example as described in the review article by N. Miyaura and A. Suzuki, *Chem. Rev.* 1995, 95, 2457. Thus, boronates can be prepared by reacting the corresponding bromo-compound with an alkyl lithium such as butyl lithium and then reacting with a borate ester. The resulting boronate ester derivative can, if desired, be hydrolysed to give the corresponding boronic acid.

Compounds of the formula (1) wherein $Q^2$ is a bond and $R^1$ is a cyclic group $Cy^1$ can be prepared by the sequence of reactions shown in Scheme 2.

Scheme 2

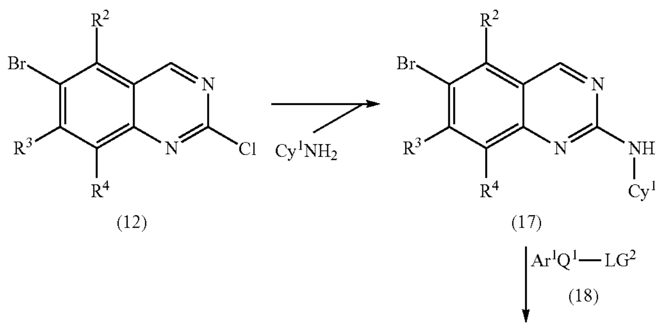

(12)

(17)

-continued

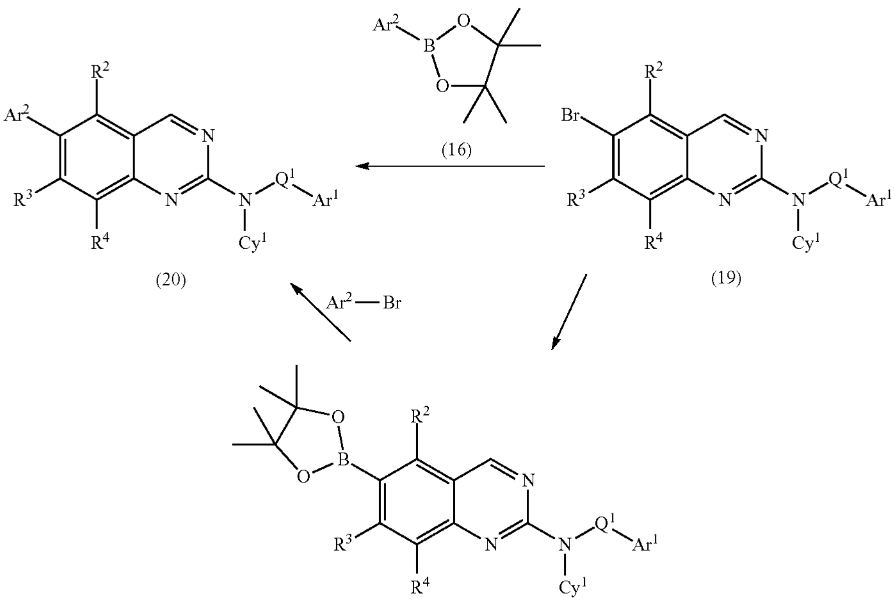

(19a)

In Scheme 2, the 6-bromo-2-chloro-quinazoline (12) is reacted with the carbocyclyl or heterocyclyl amine $Cy^1$-$NH_2$ in a polar solvent such as dimethylsulphoxide, typically at room temperature or optionally with mild heating, to give the intermediate compound (17) which is then treated with compound (18), wherein $LG^1$ is a suitable leaving group (e.g. halogen, methanesulphonate or tosylate), under standard alkylation conditions to give the bromo-compound (19). The bromo-compound (19) is then reacted with the heteroaryl boronate (16) under the Suzuki reaction conditions described above to give the compound of formula (20) which corresponds to a compound of the formula (1) in which $Q^2$ is a bond and $R^1$ is a cyclic group $Cy^1$. Alternatively, the bromo-compound (19) is reacted with bis borane pinacol ester to give the boronate (19a) which is then reacted with a heteroaryl bromide $Ar^2$—Br under Suzuki coupling conditions to give compound (20).

In cases where it is not possible to isolate a suitable reagent $Ar^2$-Bor for use in the Suzuki reaction, then the reactivity of the Suzuki reaction can be reversed as illustrated in Scheme 3 below.

Scheme 3

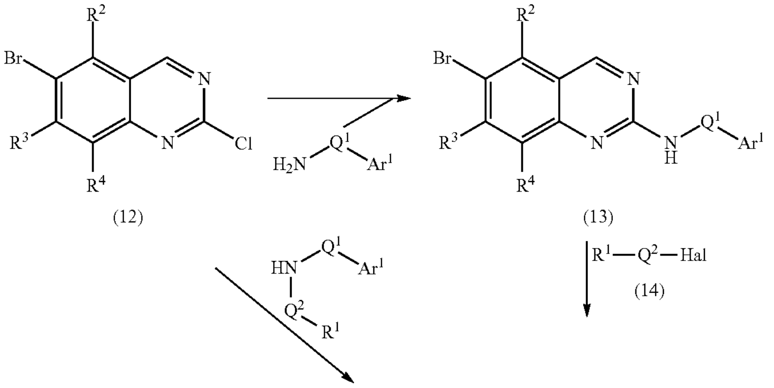

-continued

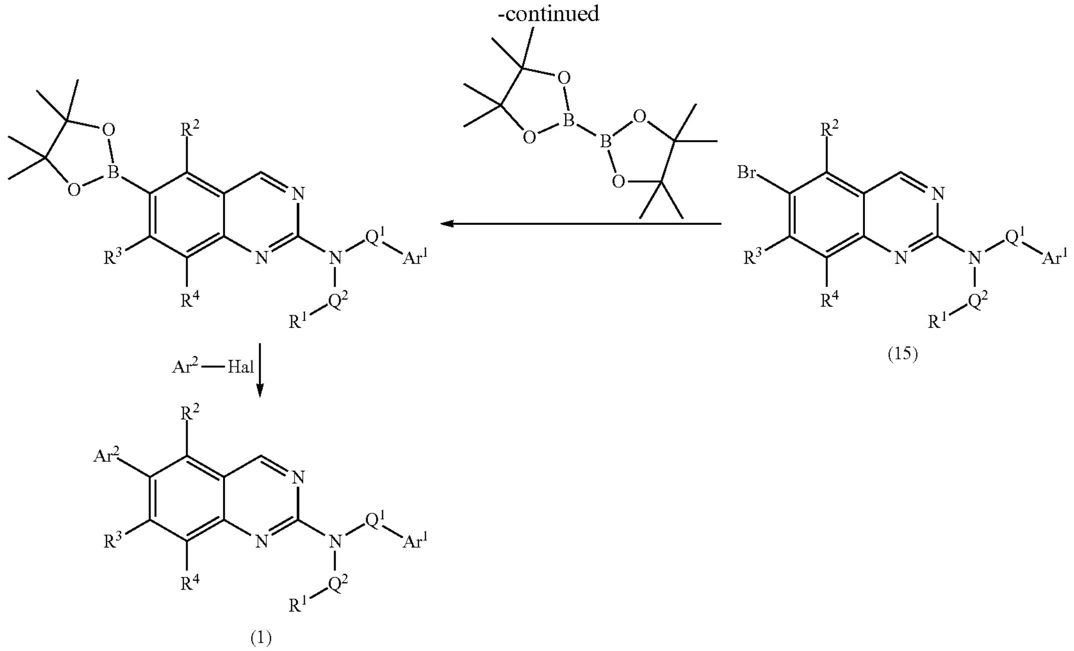

In Scheme 3 the bromide (15) is converted to a boronate ester via coupling with bispinacolate diborane in the presence of potassium acetate using a palladium catalyst such as [1,1'-Bis(diphenylphosphino)ferrocene]dichloropalladium (II), complex with dichloromethane. A polar solvent such as DMSO is preferred and the reaction mixture is heated at 80° C. under an atmosphere of nitrogen or argon to enable the reaction to take place. The resulting boronate ester is then reacted with a halogen-substituted aromatic or heteroaromatic group under Suzuki reaction conditions already described herein.

Compounds of formula (1) wherein Z is $Ar^2$ and Y is $R^3$ can be prepared as described herein using the 7-bromo-2-chloro-quinazoline regioisomer as the starting material.

Once formed, one compound of the formula (1), or a protected derivative thereof, can be converted into another compound of the formula (1) by methods well known to the skilled person. Examples of synthetic procedures for converting one functional group into another functional group are set out in standard texts such as *Advanced Organic Chemistry*, by Jerry March, $4^{th}$ edition, 119, Wiley Interscience, New York; *Fiesers' Reagents for Organic Synthesis*, Volumes 1-17, John Wiley, edited by Mary Fieser (ISBN: 0-471-58283-2); and *Organic Syntheses*, Volumes 1-8, John Wiley, edited by Jeremiah P. Freeman (ISBN: 0-471-31192-8)).

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

Compounds made by the foregoing methods may be isolated and purified by any of a variety of methods well known to those skilled in the art and examples of such methods include recrystallisation and chromatographic techniques such as column chromatography (e.g. flash chromatography) and HPLC.

Pharmaceutical Formulations

While it is possible for the active compound to be administered alone, it is preferable to present it as a pharmaceutical composition (e.g. formulation).

Accordingly, in another embodiment (Embodiment 4.1) of the invention, there is provided a pharmaceutical composition comprising at least one compound of the formula (1) as defined in any one of Embodiments 1.0 to 1.116 together with a pharmaceutically acceptable excipient.

The pharmaceutically acceptable excipient can be, for example, a carrier (e.g. a solid, liquid or semi-solid carrier), a diluent or bulking agent, a granulating agent, coating agent, binding agent, disintegrant, lubricating agent, preservative, antioxidant, buffering agent, suspending agent, thickening agent, flavouring agent, sweetener, taste masking agent or any other excipient conventionally used in pharmaceutical compositions. Examples of excipients for various types of pharmaceutical compositions are set out in more detail below.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump.

Pharmaceutical formulations adapted for parenteral administration include aqueous and non-aqueous sterile injection solutions which may contain anti-oxidants, buffers, bacteriostats, co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, interalia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

A drug molecule that is ionizable can be solubilized to the desired concentration by pH adjustment if the drug's $pK_a$ is sufficiently away from the formulation pH value. The acceptable range is pH 2-12 for intravenous and intramuscular administration, but subcutaneously the range is pH 2.7-9.0. The solution pH is controlled by either the salt form of the drug, strong acids/bases such as hydrochloric acid or sodium hydroxide, or by solutions of buffers which include but are not limited to buffering solutions formed from glycine, citrate, acetate, maleate, succinate, histidine, phosphate, tris(hydroxymethyl)-aminomethane (TRIS), or carbonate.

The combination of an aqueous solution and a water-soluble organic solvent/surfactant (i.e., a co-solvent) is often used in injectable formulations. The water-soluble organic solvents and surfactants used in injectable formulations include but are not limited to propylene glycol, ethanol, polyethylene glycol 300, polyethylene glycol 400, glycerin, dimethylacetamide (DMA), N-methyl-2-pyrrolidone (NMP; Pharmasolve), dimethylsulphoxide (DMSO), Solutol HS 15, Cremophor EL, Cremophor RH 60, and polysorbate 80. Such formulations can usually be, but are not always, diluted prior to injection.

Propylene glycol, PEG 300, ethanol, Cremophor EL, Cremophor RH 60, and polysorbate 80 are the entirely organic water-miscible solvents and surfactants used in commercially available injectable formulations and can be used in combinations with each other. The resulting organic formulations are usually diluted at least 2-fold prior to IV bolus or IV infusion.

Alternatively, increased water solubility can be achieved through molecular complexation with cyclodextrins.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyophilising a compound of Formula (1) or acid addition salt thereof. Lyophilisation refers to the procedure of freeze-drying a composition. Freeze-drying and lyophilisation are therefore used herein as synonyms. A typical process is to solubilise the compound and the resulting formulation is clarified, sterile filtered and aseptically transferred to containers appropriate for lyophilisation (e.g. vials). In the case of vials, they are partially stoppered with lyo-stoppers. The formulation can be cooled to freezing and subjected to lyophilisation under standard conditions and then hermetically capped forming a stable, dry lyophile formulation. The composition will typically have a low residual water content, e.g. less than 5% e.g. less than 1% by weight based on weight of the lyophile.

The lyophilisation formulation may contain other excipients for example, thickening agents, dispersing agents, buffers, antioxidants, preservatives, and tonicity adjusters. Typical buffers include phosphate, acetate, citrate and glycine. Examples of antioxidants include ascorbic acid, sodium bisulphite, sodium metabisulphite, monothioglycerol, thiourea, butylated hydroxytoluene, butylated hydroxyl anisole, and ethylenediaminetetraacetic acid salts. Preservatives may include benzoic acid and its salts, sorbic acid and its salts, alkyl esters of para-hydroxybenzoic acid, phenol, chlorobutanol, benzyl alcohol, thimerosal, benzalkonium chloride and cetylpyridinium chloride. The buffers mentioned previously, as well as dextrose and sodium chloride, can be used for tonicity adjustment if necessary.

Bulking agents are generally used in lyophilisation technology for facilitating the process and/or providing bulk and/or mechanical integrity to the lyophilized cake. Bulking agent means a freely water soluble, solid particulate diluent that when co-lyophilised with the compound or salt thereof, provides a physically stable lyophilized cake, a more optimal freeze-drying process and rapid and complete reconstitution. The bulking agent may also be utilised to make the solution isotonic.

The water-soluble bulking agent can be any of the pharmaceutically acceptable inert solid materials typically used for lyophilisation. Such bulking agents include, for example, sugars such as glucose, maltose, sucrose, and lactose; polyalcohols such as sorbitol or mannitol; amino acids such as glycine; polymers such as polyvinylpyrrolidine; and polysaccharides such as dextran.

The ratio of the weight of the bulking agent to the weight of active compound is typically within the range from about 1 to about 5, for example of about 1 to about 3, e.g. in the range of about 1 to 2.

Alternatively, they can be provided in a solution form which may be concentrated and sealed in a suitable vial. Sterilisation of dosage forms may be via filtration or by autoclaving of the vials and their contents at appropriate stages of the formulation process. The supplied formulation may require further dilution or preparation before delivery for example dilution into suitable sterile infusion packs.

Extemporaneous injection solutions and suspensions may be prepared from sterile powders, granules and tablets.

In one preferred embodiment of the invention, the pharmaceutical composition is in a form suitable for i.v. administration, for example by injection or infusion.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Pharmaceutical compositions containing compounds of the formula (I) can be formulated in accordance with known techniques, see for example, Remington's Pharmaceutical Sciences, Mack Publishing Company, Easton, Pa., USA.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg: tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound.

Osmotic release and other delayed release or sustained release formulations may be prepared in accordance with methods well known to those skilled in the art.

The compound of formula (1), as defined in any one of Embodiments 1.0 to 1.116, or a prodrug thereof, may be formulated with a carrier and administered in the form of nanoparticles. Nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. August 1, (2006) 5, 1909.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use include ointments, creams, sprays, patches, gels, liquid drops and inserts (for example intraocular inserts). Such compositions can be formulated in accordance with known methods.

Compositions for parenteral administration are typically presented as sterile aqueous or oily solutions or fine suspensions, or may be provided in finely divided sterile powder form for making up extemporaneously with sterile water for injection.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of Embodiments 1.0 to 1.116 will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Methods of Treatment

It is envisaged that the compounds of Embodiments 1.0 to 1.116 will be useful either as sole chemotherapeutic agents or, more usually, in combination therapy with chemotherapeutic agents or radiation therapy in the prophylaxis or treatment of a range of proliferative disease states or conditions. Examples of such disease states and conditions are set out above.

Particular examples of chemotherapeutic agents that may be co-administered with the compounds of Embodiments 1.0 to 1.116 include:

- Topoisomerase I inhibitors
- Antimetabolites
- Tubulin targeting agents
- DNA binder and topoisomerase II inhibitors
- EGFR inhibitors (e.g. Gefitinib—see Biochemical Pharmacology 78 2009 460-468)
- mTOR inhibitors (e.g. Everolimus)
- PI3K pathway inhibitors (e.g. PI3K, PDK1)
- Akt inhibitors
- Alkylating Agents (e.g. temozolomide, cyclophosphamide)
- Monoclonal Antibodies (e.g. antibodies targeting CTLA-4, PD-1, PD-L1, CD52 or CD20)
- Anti-Hormones
- Signal Transduction Inhibitors
- Proteasome Inhibitors
- DNA methyl transferases
- Cytokines and retinoids
- Hypoxia triggered DNA damaging agents (e.g. Tirapazamine)
- Aromatase inhibitors
- Anti Her2 antibodies, (see for example http://www.wipo.int/pctdb/en/wo.jsp?wo=2007056118),
- Inhibitors of angiogenesis
- HDAC inhibitors
- MEK inhibitors
- B-Raf inhibitors ERK inhibitors
HER2 small molecule inhibitors (e.g. lapatinib)
Bcr-Abl tyrosine-kinase inhibitors (e.g. imatinib)
CDK4/6 inhibitor e.g. Ibrance
VEGFR inhibitors
IGFR-1 inhibitors
Inhibitors of the Hedgehog signalling pathway Further examples of chemotherapeutic agents that may be co-administered with a compound as defined in any one Embodiments 1.0 to 1.116 include:

Torc 1 inhibitors
PI3K pathway inhibitors (e.g. PI3K, PDK1)
EGFR inhibitors (e.g. Gefitinib—refer to: Everolimus restores gefitinib sensitivity in resistant non-small cell lung cancer cell lines, Biochemical Pharmacology 78 2009 460-468)
Taxanes (e.g. paclitaxel, docetaxel, cabazitaxel)
Platinum agents (e.g. cisplatin, carboplatin, oxaliplatin)
Anthracyclines (e.g. Doxorubicin)
Inhibitors of Bcl-2 family proteins e.g. ABT263 (navitoclax), a Bcl-2/Bcl-extra large (Bcl-xL) inhibitor One particular combination comprises a compound according to any one of Embodiments 1.0 to 1.116 together with an EGFR inhibitor such as Gefitinib or Erlotinib or with an mTOR inhibitor such as Everolimus.

The compounds may also be administered in conjunction with radiotherapy.

The compounds may be administered over a prolonged term to maintain beneficial therapeutic effects or may be administered for a short period only. Alternatively they may be administered in a pulsatile or continuous manner.

The compounds of the invention will be administered in an effective amount, i.e. an amount which is effective to bring about the desired therapeutic effect. For example, the "effective amount" can be a quantity of compound which, when administered to a subject suffering from cancer, slows tumour growth, ameliorates the symptoms of the disease and/or increases longevity.

The amount of P70S6 inhibitor compound of the invention administered to the subject will depend on the type and severity of the disease or condition and on the characteristics of the subject, such as general health, age, sex, body weight and tolerance to drugs. The skilled person will be able to determine appropriate dosages depending on these and other factors.

The compounds are generally administered to a subject in need of such administration, for example a human or animal patient, preferably a human.

A typical daily dose of the compound of any of Embodiments 1.0 to 1.116 can be in the range from 100 picograms to 100 milligrams per kilogram of body weight, more typically 5 nanograms to 25 milligrams per kilogram of bodyweight, and more usually 10 nanograms to 15 milligrams per kilogram of bodyweight (e.g. 10 nanograms to 10 milligrams, and more typically 1 microgram per kilogram to 20 milligrams per kilogram, for example 1 microgram to 10 milligrams per kilogram) although higher or lower doses may be administered where required. The compound can be administered on a daily basis or on a repeat basis every 2, or 3, or 4, or 5, or 6, or 7, or 10 or 14, or 21, or 28 days for example.

In one particular dosing schedule, a patient will be given an infusion of a compound for periods of one hour daily for up to ten days in particular up to five days for one week, and the treatment repeated at a desired interval such as two to four weeks, in particular every three weeks.

More particularly, a patient may be given an infusion of a compound for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of compound administered and the type of composition used will be commensurate with the nature of the disease or physiological condition being treated and will be at the discretion of the physician.

Methods of Diagnosis

Prior to administration of a compound of any one of Embodiments 1.0 to 1.116, a patient may be screened to determine whether a disease or condition from which the patient is or may be suffering is one which would be susceptible to treatment with a compound having activity against p70S6 kinase.

For example, a biological sample taken from a patient may be analysed to determine whether a condition or disease, such as cancer, that the patient is or may be suffering from is one which is characterised by a genetic abnormality or abnormal protein expression which leads to up-regulation of p70S6 kinase or to sensitisation of a pathway to normal p70S6 kinase activity or to over-expression of phosphorylated p70S6 kinase. The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of p70S6 kinase. The term diagnosis includes screening. By marker we include genetic markers including, for example, the measurement of DNA composition to identify mutations of p70S6. The term marker also includes markers which are characteristic of up-regulation of p70S6, including enzyme activity, enzyme levels, enzyme state (e.g. phosphorylated or not) and mRNA levels of the aforementioned proteins.

Tumours with upregulation of p70S6 kinase may be particularly sensitive to p70S6 inhibitors. Tumours may preferentially be screened for upregulation of p70S6. Thus, the patient may be subjected to a diagnostic test to detect a marker characteristic of up-regulation of p70S6. The diagnostic tests are typically conducted on a biological sample selected from tumour biopsy samples, blood samples (isolation and enrichment of shed tumour cells), stool biopsies, sputum, chromosome analysis, pleural fluid, peritoneal fluid, Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridisation.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, 3rd Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828;

4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649).

Generally, in situ hybridization comprises the following major steps: (1) fixation of tissue to be analyzed; (2) pre-hybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. Current Protocols in Molecular Biology, 2004, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Alternatively, the protein products expressed from the mRNAs may be assayed by immunohistochemistry of tumour samples, solid phase immunoassay with microtiter plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of up-regulation of p70S6 kinase could be applicable in the present case.

Accordingly, in another embodiment of the invention (Embodiment 5.1), there is provided a method for the diagnosis and treatment of a disease state or condition mediated by p70S6 kinase which method comprises (i) screening a patient to determine whether a disease or condition from which the patient is or may be suffering is one which would be susceptible to treatment with a compound having activity against p70S6 kinase; and (ii) where it is indicated that the disease or condition from which the patient is thus susceptible, thereafter administering to the patient a compound as defined in any one of Embodiments 1.0 to 1.116.

In another embodiment (Embodiment 5.2), there is provided the use of a compound as defined in any one of Embodiments 1.0 to 1.116 for the manufacture of a medicament for the treatment or prophylaxis of a disease state or condition in a patient who has been screened and has been determined as suffering from, or being at risk of suffering from, a disease or condition which would be susceptible to treatment with a compound having activity against p70S6.

In a further embodiment (Embodiment 5.3), there is provided a compound as defined in any one of Embodiments 1.0 to 1.116 for use in the treatment or prophylaxis of a disease state or condition in a patient who has been screened and has been determined as suffering from, or being at risk of suffering from, a disease or condition which would be susceptible to treatment with a compound having activity against p70S6.

In another embodiment of the invention (Embodiment 5.4), there is provided a method for the diagnosis and treatment of a disease state or condition characterised by up-regulation of p70S6 kinase or the presence of a mutated form of p70S6, which method comprises (i) screening a patient to determine whether a disease or condition from which the patient is or may be suffering is one which would be susceptible to treatment with a compound having activity against p70S6 kinase; and (ii) where it is indicated that the disease or condition from which the patient is thus susceptible, thereafter administering to the patient a compound as defined in any one of Embodiments 1.0 to 1.116.

In a further embodiment (Embodiment 5.5), there is provided a method for the treatment of a disease state or condition characterised by up-regulation of p70S6 kinase or the presence of a mutated form of p70S6, which method comprises administering a therapeutically effective amount of a compound as defined in any one of Embodiments 1.0 to 1.116 to a patient who has been screened and has been determined as suffering from, or being at risk of suffering from, a disease or condition which would be susceptible to treatment with a compound having activity against p70S6.

In another embodiment (Embodiment 5.6), there is provided the use of a compound as defined in any one of Embodiments 1.0 to 1.116 for the manufacture of a medicament for the treatment or prophylaxis of a disease, condition of disorder as defined in any one of Embodiments 2.1 to 2.43 in a patient who has been screened and has been determined as suffering from, or being at risk of suffering, from a said disease, condition or disorder which would be susceptible to treatment with a compound having activity against p70S6.

In a further embodiment (Embodiment 5.7), there is provided a compound as defined in any one of Embodiments 1.0 to 1.116 for use in the treatment or prophylaxis of a disease or brain disorder in a patient who has been screened and has been determined as suffering from, or being at risk of suffering from, a disease, condition of disorder as defined in any one of Embodiments 2.1 to 2.43 which would be susceptible to treatment with a compound having activity against p70S6.

Triple-negative breast cancers are characterised in that the cancer does not express the genes for estrogen receptor (ER), progesterone receptor (PR) or HER2. The presence of ER and PR can be determined by standard immuno-histochemical staining methods (see for example, Narod et al, Triple-Negative Breast Cancer: Clinical Features and Patterns of Recurrence, Clin Cancer Res Aug. 1, 2007 13; 4429). Alternatively, it is possible to assess gene expression of these proteins by methods such as Quantitative real-time polymerase chain reaction (QRT-PCR) with commercially available PCR assays (see Jozefczuk et al, Quantitative real-time PCR-based analysis of gene expression, Methods Enzymol. 2011; 500:99-109).

Overexpression of the HER2 protein can be evaluated using the CB11 monoclonal antibody in representative paraffin sections of each tumour using the peroxidase-antiperoxidase technique for immunohistochemical assay. A tumour is defined as exhibiting HER2 positivity when strong complete membrane staining is observed in at least 10% of tumour cells (Narod et al, Clin Cancer Res Aug. 1, 2007 13; 4429).

Accordingly, in another embodiment of the invention (Embodiment 5.8), there is provided a method for the diagnosis and treatment of a cancer as defined in any one of Embodiments 2.10 to 2.18, which method comprises (i) screening a patient to determine whether a cancer from which the patient is or may be suffering is one which does not express estrogen receptor, progesterone receptor and/or HER2; and (ii) where it is indicated that the cancer which the patient is thus susceptible to, thereafter administering to the patient a compound as defined in any one of Embodiments 1.0 to 1.116.

In another embodiment (Embodiment 5.9), there is provided the use of a compound as defined in any one of Embodiments 1.0 to 1.116 for the manufacture of a medicament for the treatment or prophylaxis of a cancer as defined in any one of Embodiments 2.10 to 2.18 in a patient who has been screened and has been determined as suffering from, or being at risk of suffering, from a cancer which does not express estrogen receptor, progesterone receptor and/or HER2.

In a further embodiment (Embodiment 5.10), there is provided a compound as defined in any one of Embodiments 1.0 to 1.116 for use in the treatment or prophylaxis of a cancer as defined in any one of Embodiments 2.10 to 2.18 in a patient who has been screened and has been determined as suffering from, or being at risk of suffering, from a cancer which does not express estrogen receptor, progesterone receptor and/or HER2.

Fragile X syndrome occurs as a result of a mutation of the fragile X mental retardation 1 gene (FMR1). In individuals affected by FXS, the FMR1 gene contains over 45, more commonly over 55 and in some cases over 200 repeats of the CGG codon compared to between 5 and 44 times, more commonly either 29 or 30 times, in unaffected individuals. This mutation results in a failure to express fragile X mental retardation protein FMRP leading to excessive production of an array of proteins normally controlled by FMRP. As FXS is a genetic disease, diagnosis of FXS can be readily accomplished by running a genetic test from a blood or skin sample of the patient in question. FXS patients will not express or have much lower FMR1 mRNA levels than unaffected individuals. The levels of FMR1 mRNA levels may be quantified using real-time PCR, assays for which are commercially available. In addition, the size of the CGG repeat can be determined by isolating genomic DNA by salting out followed by PCR. See, for example, Kumari et al. (HUMAN MUTATION, Vol. 35, No. 12, 1485-1494, 2014) for laboratory methods to obtain this data. Thus, biomarkers that enable FXS to be identified in a patient include FMR1 mRNA levels and the presence of oversized CGG repeats in a patient's genomic DNA.

Accordingly, in another embodiment of the invention (Embodiment 5.11), there is provided a method for the diagnosis and treatment of Fragile X syndrome, which method comprises (i) screening a patient for one or more biomarkers indicative of Fragile X syndrome; and (ii) where such a biomarker is detected, thereafter administering to the patient a compound as defined in any one of Embodiments 1.0 to 1.116.

In another embodiment (Embodiment 5.12), there is provided the use of a compound as defined in any one of Embodiments 1.0 to 1.116 for the manufacture of a medicament for the treatment or prophylaxis of Fragile X syndrome in a patient who has been screened for and found to harbour one or more biomarkers indicative of Fragile X syndrome.

In a further embodiment (Embodiment 5.13), there is provided a compound as defined in any one of Embodiments 1.0 to 1.116 for use in the treatment or prophylaxis of Fragile X syndrome in a patient who has been screened for and found to harbour one or more biomarkers indicative of Fragile X syndrome.

In another embodiment of the invention (Embodiment 5.14), there is provided a method for the diagnosis and treatment of Fragile X syndrome, which method comprises (i) screening a patient to determine whether they have levels of FMR1 mRNA indicative of Fragile X syndrome; and (ii) where it is indicated that they do have such levels of FMR1 mRNA, thereafter administering to the patient a compound as defined in any one of Embodiments 1.0 to 1.116.

In another embodiment (Embodiment 5.15), there is provided the use of a compound as defined in any one of Embodiments 1.0 to 1.116 for the manufacture of a medicament for the treatment or prophylaxis of Fragile X syndrome in a patient who has been screened and has been determined as having levels of FMR1 mRNA indicative of Fragile X syndrome.

In a further embodiment (Embodiment 5.16), there is provided a compound as defined in any one of Embodiments 1.0 to 1.116 for use in the treatment or prophylaxis of Fragile X syndrome in a patient who has been screened and has been determined as having levels of FMR1 mRNA indicative of Fragile X syndrome.

EXAMPLES

Examples 1 to 43

Figure 1:
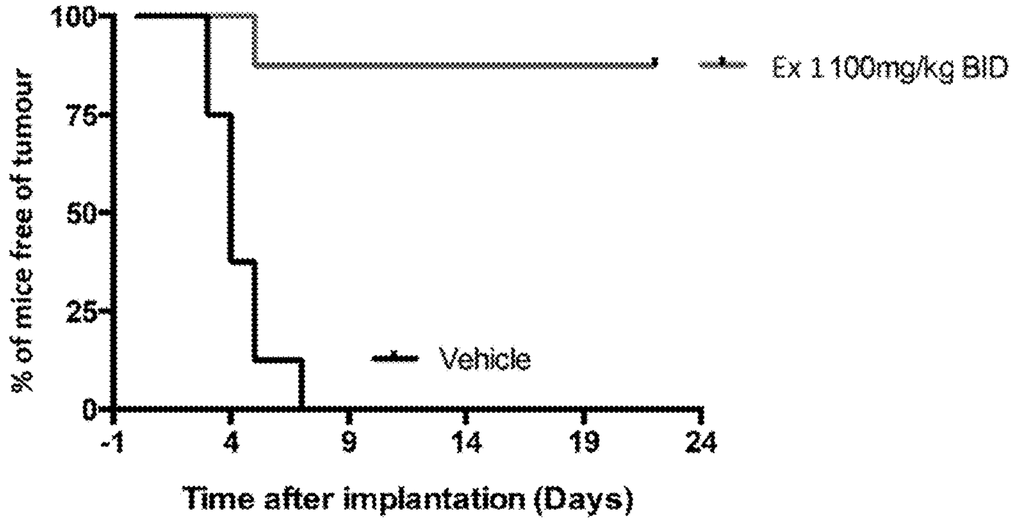
FIG. 1 illustrates results obtained from in an in vivo model of triple negative breast cancer as described in Example 44 herein, and in particular shows the percentage of mice free of tumour against the number of days after implantation of the tumour when treated with 100 mg/kg of Example 1 or the vehicle.

The compounds of Examples 1 to 43 in Table 1 below are illustrative of the invention.

Example 1

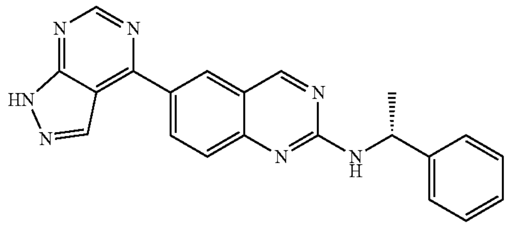 [SMILES: C[C@@H](Nc1ncc2cc(-c3ncnc4[nH]ncc34)ccc2n1)c1ccccc1]

-continued
Example 2
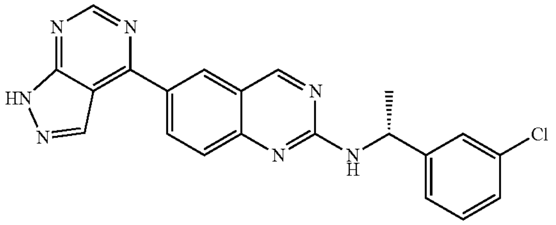 [SMILES: C[C@@H](Nc1ncc2cc(-c3ncnc4[nH]ncc34)ccc2n1)c1cccc(Cl)c1]
Example 3
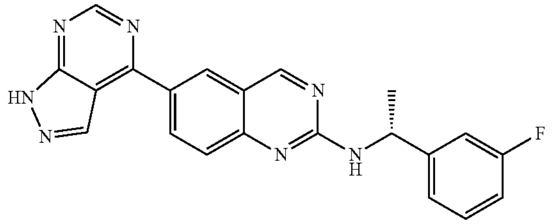 [SMILES: C[C@@H](Nc1ncc2cc(-c3ncnc4[nH]ncc34)ccc2n1)c1cccc(F)c1]
Example 4
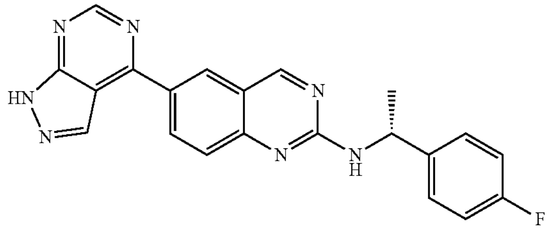 [SMILES: C[C@@H](Nc1ncc2cc(-c3ncnc4[nH]ncc34)ccc2n1)c1ccc(F)cc1]
Example 5
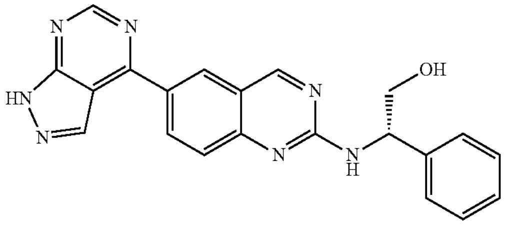 [SMILES: OC[C@@H](Nc1ncc2cc(-c3ncnc4[nH]ncc34)ccc2n1)c1ccccc1]
Example 6
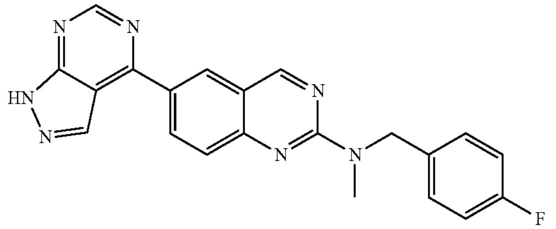 [SMILES: CN(Cc1ccc(F)cc1)c1ncc2cc(-c3ncnc4[nH]ncc34)ccc2n1]
Example 7
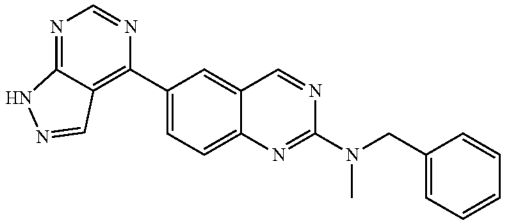 [SMILES: CN(Cc1ccccc1)c1ncc2cc(-c3ncnc4[nH]ncc34)ccc2n1]
Example 8
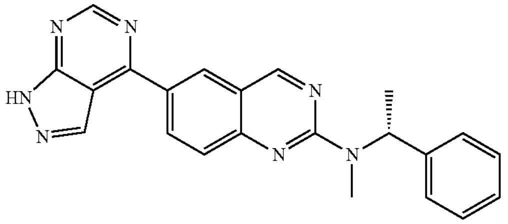

-continued
Example 9
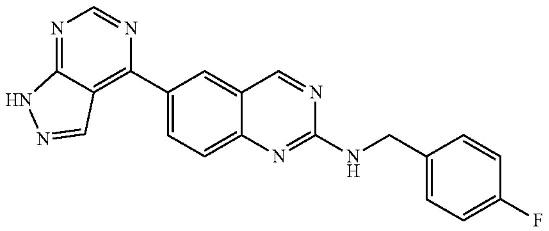 [SMILES: Fc1ccc(CNc2ncc3cc(-c4ncnc5[nH]ncc45)ccc3n2)cc1]
Example 10
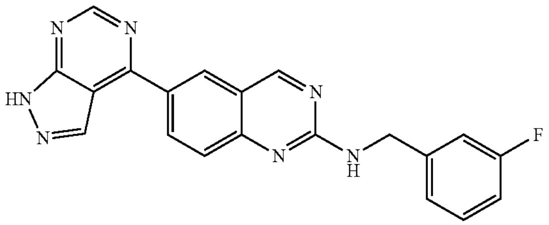 [SMILES: Fc1cccc(CNc2ncc3cc(-c4ncnc5[nH]ncc45)ccc3n2)c1]
Example 11
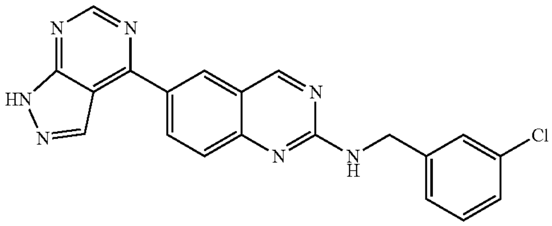 [SMILES: Clc1cccc(CNc2ncc3cc(-c4ncnc5[nH]ncc45)ccc3n2)c1]
Example 12
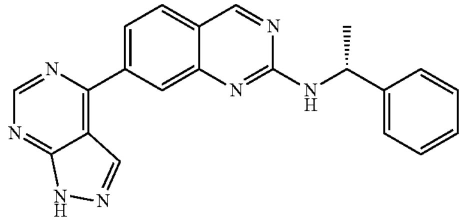 [SMILES: C[C@@H](Nc1ncc2ccc(-c3ncnc4[nH]ncc34)cc2n1)c1ccccc1]
Example 13
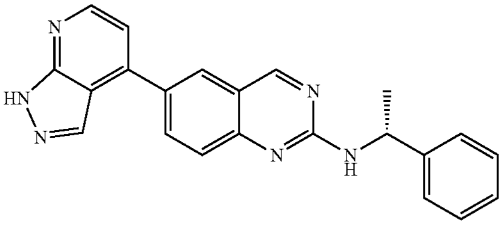 [SMILES: C[C@@H](Nc1ncc2cc(-c3ccnc4[nH]ncc34)ccc2n1)c1ccccc1]
Example 14
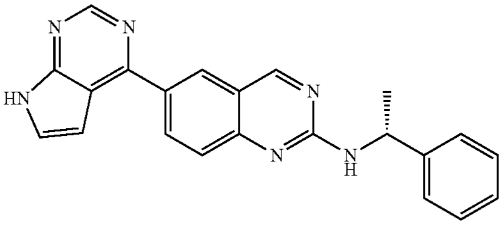 [SMILES: C[C@@H](Nc1ncc2cc(-c3ncnc4[nH]ccc34)ccc2n1)c1ccccc1]

-continued
Example 15
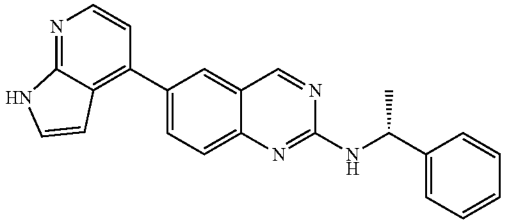 [SMILES: C[C@@H](Nc1ncc2cc(-c3ccnc4[nH]ccc34)ccc2n1)c1ccccc1]
Example 16
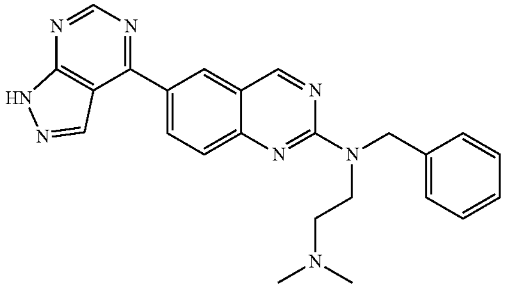 [SMILES: CN(C)CCN(Cc1ccccc1)c1ncc2cc(-c3ncnc4[nH]ncc34)ccc2n1]
Example 17
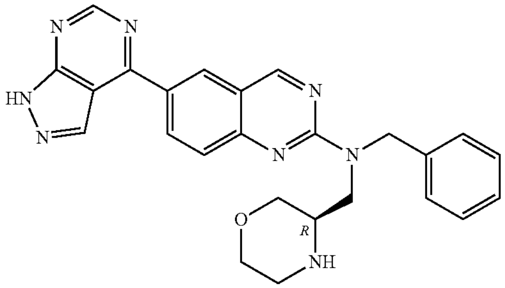
Example 18
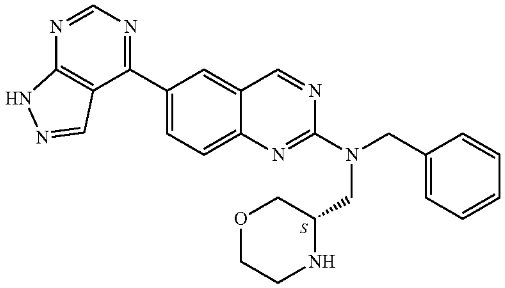
Example 19
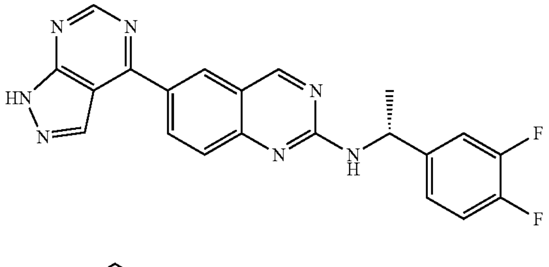
Example 20
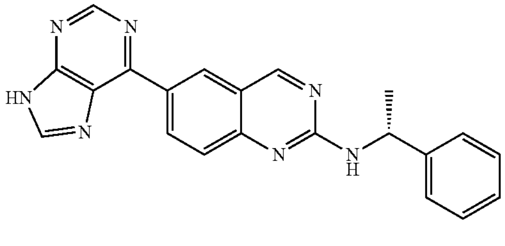 [SMILES: C[C@@H](Nc1ncc2cc(-c3ncnc4[nH]cnc34)ccc2n1)c1ccccc1]

-continued
Example 21
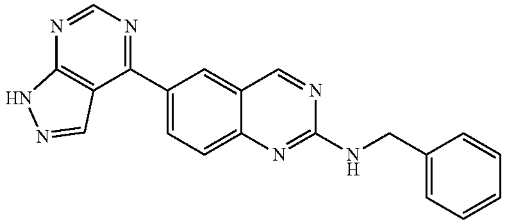 [SMILES: c1ccc(CNc2ncc3cc(-c4ncnc5[nH]ncc45)ccc3n2)cc1]
Example 22
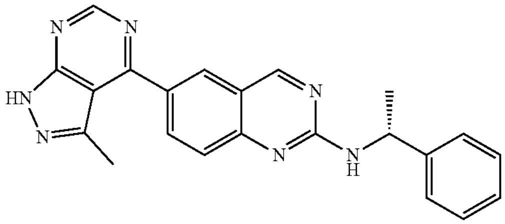 [SMILES: Cc1n[nH]c2ncnc(-c3ccc4nc(N[C@H](C)c5ccccc5)ncc4c3)c12]
Example 23
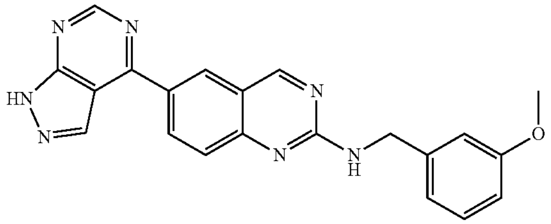 [SMILES: COc1cccc(CNc2ncc3cc(-c4ncnc5[nH]ncc45)ccc3n2)c1]
Example 24
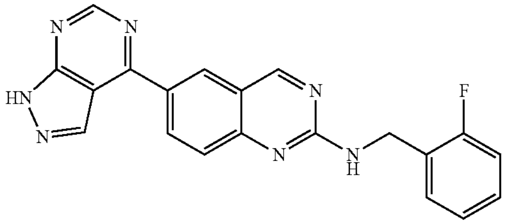 [SMILES: Fc1ccccc1CNc1ncc2cc(-c3ncnc4[nH]ncc34)ccc2n1]
Example 25
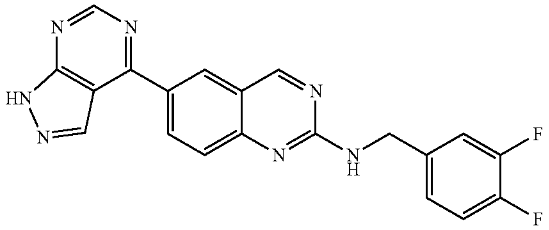 [SMILES: Fc1ccc(CNc2ncc3cc(-c4ncnc5[nH]ncc45)ccc3n2)cc1F]
Example 26
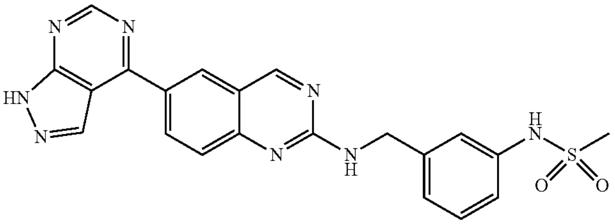 [SMILES: CS(=O)(=O)Nc1cccc(CNc2ncc3cc(-c4ncnc5[nH]ncc45)ccc3n2)c1]
Example 27
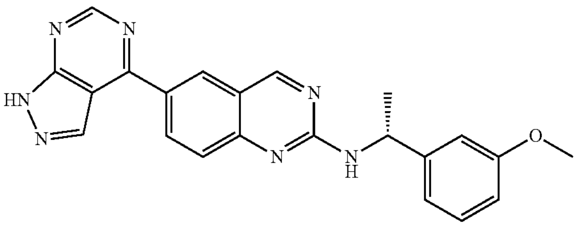 [SMILES: COc1cccc([C@@H](C)Nc2ncc3cc(-c4ncnc5[nH]ncc45)ccc3n2)c1]

-continued
Example 28
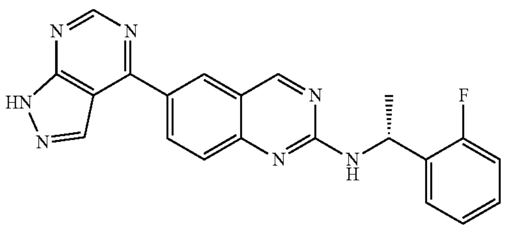 [SMILES: C[C@@H](Nc1ncc2cc(-c3ncnc4[nH]ncc34)ccc2n1)c1ccccc1F]
Example 29
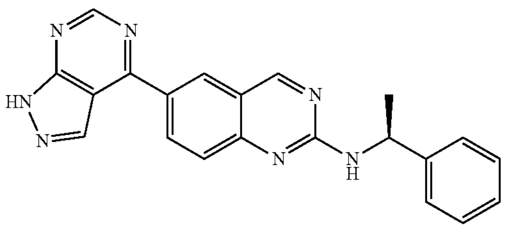 [SMILES: C[C@H](Nc1ncc2cc(-c3ncnc4[nH]ncc34)ccc2n1)c1ccccc1]
Example 30
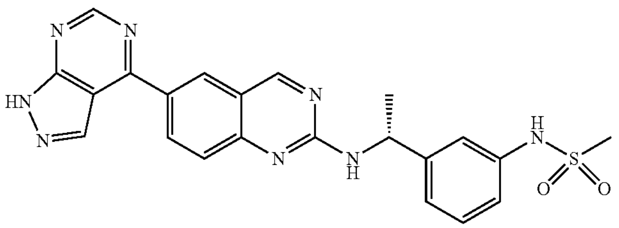 [SMILES: C[C@@H](Nc1ncc2cc(-c3ncnc4[nH]ncc34)ccc2n1)c1cccc(NS(C)(=O)=O)c1]
Example 31
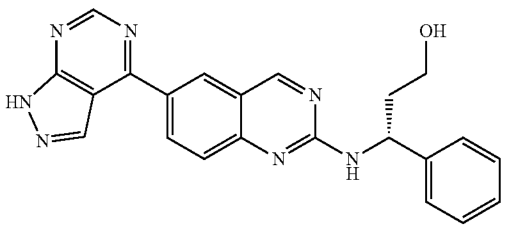 [SMILES: OCC[C@@H](Nc1ncc2cc(-c3ncnc4[nH]ncc34)ccc2n1)c1ccccc1]
Example 32
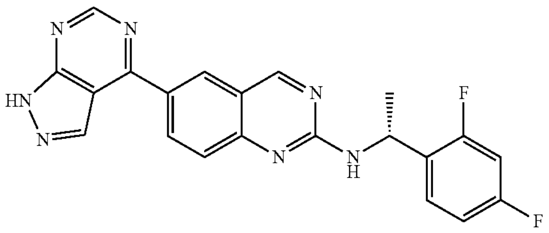 [SMILES: C[C@@H](Nc1ncc2cc(-c3ncnc4[nH]ncc34)ccc2n1)c1ccc(F)cc1F]
Example 33
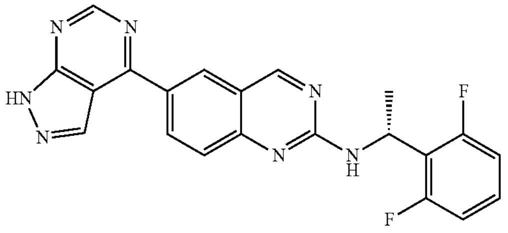 [SMILES: C[C@@H](Nc1ncc2cc(-c3ncnc4[nH]ncc34)ccc2n1)c1c(F)cccc1F]

-continued
Example 34
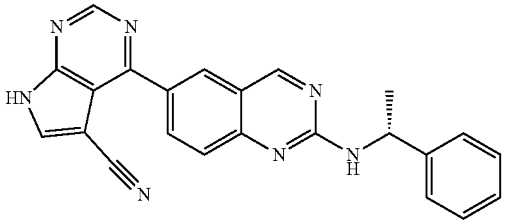 [SMILES: C[C@@H](Nc1ncc2cc(-c3ncnc4[nH]cc(C#N)c34)ccc2n1)c1ccccc1]
Example 35
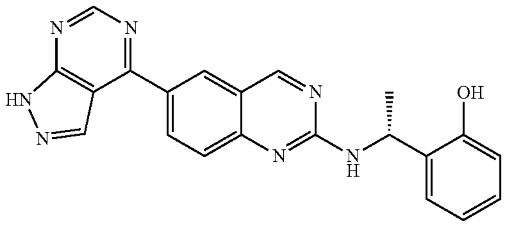 [SMILES: C[C@@H](Nc1ncc2cc(-c3ncnc4[nH]ncc34)ccc2n1)c1ccccc1O]
Example 36
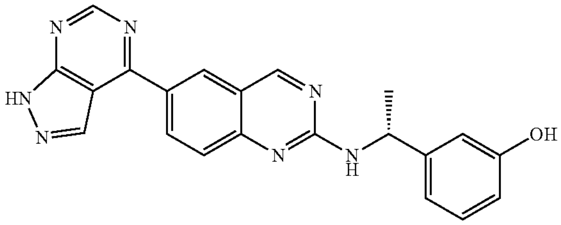 [SMILES: C[C@@H](Nc1ncc2cc(-c3ncnc4[nH]ncc34)ccc2n1)c1cccc(O)c1]
Example 37
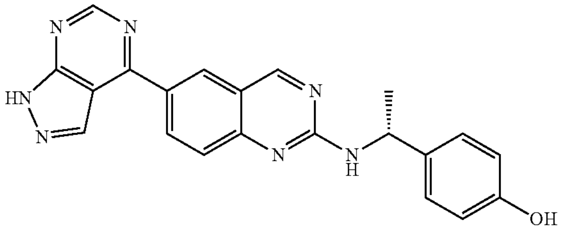 [SMILES: C[C@@H](Nc1ncc2cc(-c3ncnc4[nH]ncc34)ccc2n1)c1ccc(O)cc1]
Example 38
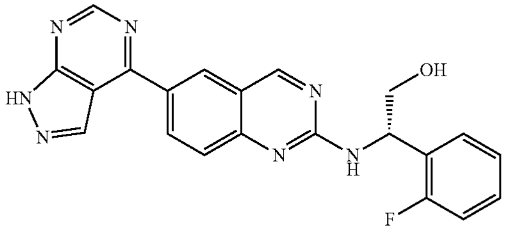 [SMILES: OC[C@@H](Nc1ncc2cc(-c3ncnc4[nH]ncc34)ccc2n1)c1ccccc1F]
Example 39
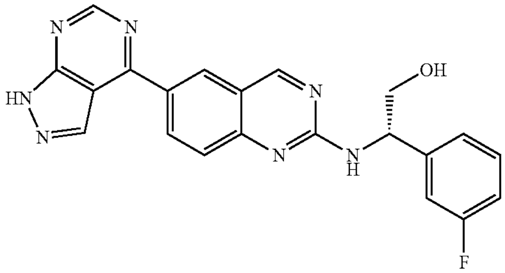 [SMILES: OC[C@@H](Nc1ncc2cc(-c3ncnc4[nH]ncc34)ccc2n1)c1cccc(F)c1]

-continued

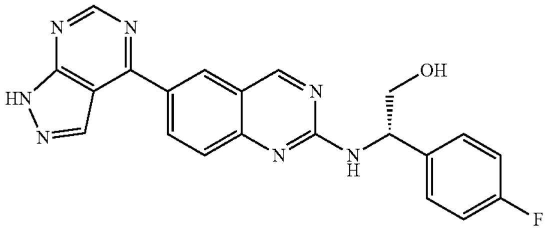 [SMILES: OC[C@@H](Nc1ncc2cc(-c3ncnc4[nH]ncc34)ccc2n1)c1ccc(F)cc1]
Example 40

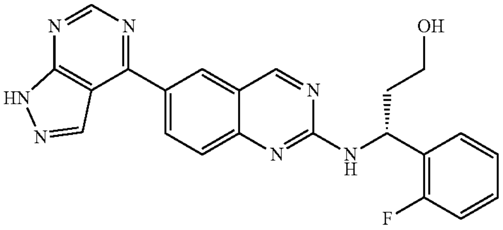 [SMILES: OCC[C@@H](Nc1ncc2cc(-c3ncnc4[nH]ncc34)ccc2n1)c1ccccc1F]
Example 41

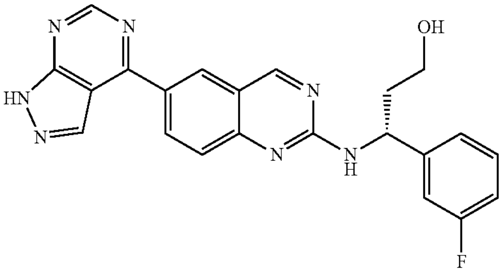 [SMILES: OCC[C@@H](Nc1ncc2cc(-c3ncnc4[nH]ncc34)ccc2n1)c1cccc(F)c1]
Example 42

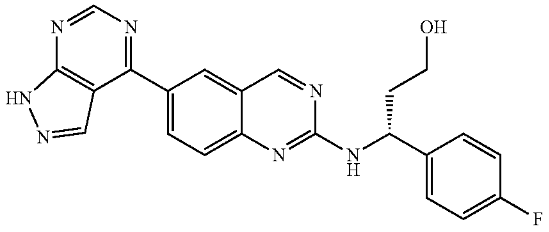 [SMILES: OCC[C@@H](Nc1ncc2cc(-c3ncnc4[nH]ncc34)ccc2n1)c1ccc(F)cc1]
Example 43

Analytical Data $^1$H NMR spectra were recorded on a Bruker 400 machine.

LCMS Methods:

LCMS analysis was carried using the following method (s):

LCMS Method 1

| Parameter | Information |
|---|---|
| LCMS equipment | Waters Alliance 2690 |
| Column flow (mL/min) | 1.2 |
| Eluent solvents (mobile phase) | (A) 0.1% Ammonia in water; (B) 100% methanol |
| Column supplier | Waters |
| Column name | X BRIDGE C18 column |
| Column length (mm) | 100 |
| Column internal diameter (mm) | 4.6 |
| Column particle size (micron) | 5 |

Elution Gradient:

| Time (min) | % A | % B |
|---|---|---|
| 0.0 | 90 | 10 |
| 1.00 | 90 | 10 |

-continued

| Time (min) | % A | % B |
|---|---|---|
| 5.00 | 0 | 100 |
| 7.00 | 0 | 100 |
| 7.50 | 90 | 10 |
| 8.00 | 90 | 10 |

LCMS Method 2

LC-MS was carried out using a Waters Acquity H class device with SingleQda-Mass Detector using Positive/negative electrospray ionisation. The column used was as follows: Waters Acquity BEH C18 (50×2.1 mm) 1.7 micron. Column flow rate: 0.55 mL/min. Solvent system used: mobile phase (A) 5 mm Ammonium Acetate+0.1% Formic acid (FA) in water and (B) 0.1% FA in Acetonitrile according to the following gradient:

| Time (min) | A % | B % |
|---|---|---|
| 0.01 | 95 | 5 |
| 0.4 | 95 | 5 |
| 0.8 | 65 | 35 |

-continued

| Time (min) | A % | B % |
|---|---|---|
| 1.2 | 45 | 55 |
| 2.5 | 0 | 100 |
| 3.3 | 0 | 100 |
| 3.31 | 95 | 5 |
| 4.00 | 95 | 5 |

LCMS Method 3

| Parameter | Information |
|---|---|
| LCMS equipment | Waters Alliance 2690 |
| Column flow (mL/min) | 1.2 |
| Eluent solvents (mobile phase) | (A) 10 nM Ammonium bicarbonate in water; (B) 100% methanol |
| Column supplier | Waters |
| Column name | X BRIDGE C18 column |
| Column length (mm) | 100 |
| Column internal diameter (mm) | 4.6 |
| Column particle size (micron) | 5 |

Elution Gradient:

| Time (min) | % A | % B |
|---|---|---|
| 0.0 | 90 | 10 |
| 1.00 | 90 | 10 |
| 5.00 | 0 | 100 |
| 7.00 | 0 | 100 |
| 7.50 | 90 | 10 |
| 8.00 | 90 | 10 |

LCMS Method 4

| Parameter | Information |
|---|---|
| LCMS equipment | Waters Alliance 2690 |
| Column flow (mL/min) | 1.2 |
| Eluent solvents (mobile phase) | (A) % triflouroacetic acid in water; (B) 100% methanol |
| Column supplier | Waters |
| Column name | X BRIDGE C18 column |
| Column length (mm) | 100 |
| Column internal diameter (mm) | 4.6 |
| Column particle size (micron) | 5 |

Elution Gradient:

| Time (min) | % A | % B |
|---|---|---|
| 0.01 | 90 | 10 |
| 3.00 | 10 | 90 |
| 6.00 | 0 | 100 |
| 7.00 | 0 | 100 |
| 7.01 | 90 | 10 |
| 10.00 | 90 | 10 |

LCMS Method 5

| Parameter | Information |
|---|---|
| LCMS equipment | Waters ACQUITY UPLC System |
| Column flow (mL/min) | 0.8 |
| Eluent solvents (mobile phase) | (A) 0.1% formic acid in water; (B) 100% acetonitrile |
| Column supplier | Waters |
| Column name | BEH C18 column |
| Column length (mm) | 50 |
| Column internal diameter (mm) | 2.1 |
| Column particle size (micron) | 1.7 |

Elution Gradient:

| Time (min) | % A | % B |
|---|---|---|
| 0.00 | 90 | 10 |
| 0.75 | 90 | 10 |
| 2.80 | 10 | 90 |
| 4.50 | 00 | 100 |
| 4.60 | 00 | 100 |
| 4.70 | 90 | 10 |
| 6.00 | 90 | 10 |

LCMS Method 6

| Parameter | Information |
|---|---|
| LCMS equipment | Waters Alliance 2690 |
| Column flow (mL/min) | 1.2 |
| Eluent solvents (mobile phase) | (A) 10 nM Ammonium bicarbonate in water; (B) 100% methanol |
| Column supplier | Waters |
| Column name | X BRIDGE C18 column |
| Column length (mm) | 50 |
| Column internal diameter (mm) | 4.6 |
| Column particle size (micron) | 3.5 |

Elution Gradient:

| Time (min) | % A | % B |
|---|---|---|
| 0.00 | 90 | 10 |
| 1.00 | 90 | 10 |
| 4.00 | 0 | 100 |
| 6.00 | 0 | 100 |
| 6.50 | 90 | 10 |
| 7.00 | 90 | 10 |

Chiral HPLC Methods:

Chiral HPLC analysis was carried out using the following methods:

Chiral HPLC Method 1

Chiral HPLC was carried out using a Waters Super-critical Fluid Chromatography (SFC) Investigator analytical HPLC device with PDA Detector. Flow rate: 4.0 ml/min. Injection volume: 10 uL. Analytical column used: Chiralpak IB (250*4.6 mm) 5 micron particle size. Solvent system used: mobile phase (A) liquid carbon dioxide (B) 100% methanol according to the following gradient:

| Time (min) | A % | B % |
|---|---|---|
| 0 | 95 | 5 |
| 5 | 50 | 50 |
| 10 | 50 | 50 |

Chiral HPLC Method 2

| Parameter | Information |
|---|---|
| Chiral HPLC equipment | SHIMADZU-2010 CHT |
| Column flow (mL/min) | 1.0 |
| Eluent solvents (mobile phase) | (A) 0.1% DEA in hexane; (B) 0.1% DEA in ethanol |
| Column supplier | Daicel |
| Column name | Chiralpak IA |
| Column length (mm) | 250 |
| Column internal diameter (mm) | 4.6 |
| Column particle size (micron) | 5 |

An isocratic elution was used:

| % A | % B |
|---|---|
| 60 | 40 |

Chiral HPLC Method 3

Chiral HPLC was carried out using a Waters Supercritical Fluid Chromatography (SFC) Investigator analytical HPLC device with PDA Detector. Flow rate: 4.0 ml/min. Injection volume: 35 uL. Analytical column used: Chiralpak IB (250*4.6 mm) 5 micron particle size. Solvent system used: mobile phase (A) liquid carbon dioxide (B) 100% methanol according to the following gradient:

| Time (min) | A % | B % |
|---|---|---|
| 0 | 90 | 10 |
| 2 | 90 | 10 |
| 5 | 50 | 50 |
| 10 | 50 | 50 |

Chiral HPLC Method 4

Chiral HPLC was carried out using a Waters Supercritical Fluid Chromatography (SFC) Investigator analytical HPLC device with PDA Detector. Flow rate: 4.0 ml/min. Injection volume: 20 uL. Analytical column used: Chiralpak IB (250*4.6 mm) 5 micron particle size. Solvent system used: mobile phase (A) liquid carbon dioxide (B) 50:50 isopropanol:acetonitrile according to the following gradient:

| Time (min) | A % | B % |
|---|---|---|
| 0 | 95 | 5 |
| 5 | 50 | 50 |
| 10 | 50 | 50 |

Chiral HPLC Method 5

| Parameter | Information |
|---|---|
| Chiral HPLC equipment | SHIMADZU-2010 CHT |
| Column flow (mL/min) | 1.0 |
| Eluent solvents (mobile phase) | (A) 0.1% DEA in hexane; (B) 0.1% DEA in ethanol |
| Column supplier | Daicel |
| Column name | Chiralpak IA |
| Column length (mm) | 250 |
| Column internal diameter (mm) | 4.6 |
| Column particle size (micron) | 5 |

An isocratic elution was used:

| % A | % B |
|---|---|
| 50 | 50 |

Chiral HPLC Method 6

| Parameter | Information |
|---|---|
| Chiral HPLC equipment | SHIMADZU-2010 CHT |
| Column flow (mL/min) | 1.0 |
| Eluent solvents (mobile phase) | (A) 0.1% diethylamine (DEA) in hexane; (B) ethanol |
| Column supplier | Daicel |
| Column name | Chiralpak IA |
| Column length (mm) | 250 |
| Column internal diameter (mm) | 4.6 |
| Column particle size (micron) | 5 |

An isocratic elution was used:

| % A | % B |
|---|---|
| 50 | 50 |

Chiral HPLC Method 7

| Parameter | Information |
|---|---|
| Chiral HPLC equipment | SHIMADZU-2010 CHT |
| Column flow (mL/min) | 1.0 |
| Eluent solvents (mobile phase) | (A) 0.1% DEA in hexane; (B) 0.1% DEA in IPA |
| Column supplier | Daicel |
| Column name | Chiralpak IA |
| Column length (mm) | 250 |
| Column internal diameter (mm) | 4.6 |
| Column particle size (micron) | 5 |

An isocratic elution was used:

| % A | % B |
|---|---|
| 25 | 75 |

Chiral HPLC Method 8

| Parameter | Information |
|---|---|
| Chiral HPLC equipment | SHIMADZU-2010 CHT |
| Column flow (mL/min) | 1.0 |
| Eluent solvents (mobile phase) | (A) 0.1% DEA in water; (B) 0.1% DEA in acetonitrile |
| Column supplier | Daicel |
| Column name | Chiralpak IA |
| Column length (mm) | 250 |
| Column internal diameter (mm) | 4.6 |
| Column particle size (micron) | 5 |

Elution Gradient:

| Time (min) | % A | % B |
|---|---|---|
| 0.01 | 90 | 10 |
| 9.00 | 10 | 90 |
| 11.00 | 0 | 100 |

-continued

| Time (min) | % A | % B |
|---|---|---|
| 20.00 | 0 | 100 |
| 20.01 | 90 | 10 |
| 27.00 | 90 | 10 |

Chiral HPLC Method 9

| Parameter | Information |
|---|---|
| Chiral HPLC equipment | SHIMADZU-2010 CHT |
| Column flow (mL/min) | 1.0 |
| Eluent solvents (mobile phase) | (A) 10 mM $NH_4HCO_3$ in water (B) 100% acetonitrile |
| Column supplier | Daicel |
| Column name | Chiralpak IA |
| Column length (mm) | 250 |
| Column internal diameter (mm) | 4.6 |
| Column particle size (micron) | 5 |

Elution Gradient:

| Time (min) | % A | % B |
|---|---|---|
| 0.01 | 90 | 10 |
| 9.00 | 10 | 90 |
| 11.00 | 0 | 100 |
| 20.00 | 0 | 100 |
| 20.01 | 90 | 10 |
| 27.00 | 90 | 10 |

Chiral HPLC Method 10

| Parameter | Information |
|---|---|
| Chiral HPLC equipment | Agilent 1200 series PDA |
| Column flow (mL/min) | 1.0 |
| Eluent solvents (mobile phase) | (A) 0.1% DEA in hexane; (B) 100% IPA |
| Column supplier | Daicel |
| Column name | Chiralpak IB |
| Column length (mm) | 250 |
| Column internal diameter (mm) | 4.6 |
| Column particle size (micron) | 5 |

Elution Gradient:

| Time (min) | % A | % B |
|---|---|---|
| 0.00 | 90 | 10 |
| 5.00 | 90 | 10 |
| 10.00 | 70 | 30 |
| 15.00 | 70 | 30 |
| 25.00 | 40 | 60 |
| 30.00 | 15 | 85 |
| 35.00 | 15 | 85 |
| 35.01 | 90 | 10 |
| 40.00 | 90 | 10 |

Chiral HPLC Method 11

The same method was used as for Chiral method 10 except that ethanol was used as solvent B Chiral HPLC Method 12

| Parameter | Information |
|---|---|
| Chiral HPLC equipment | Agilent 1200 series PDA |
| Column flow (mL/min) | 1.0 |
| Eluent solvents (mobile phase) | (A) 0.1% DEA in heptanes; (B) 100% IPA |
| Column supplier | Daicel |
| Column name | Chiralpak IA |
| Column length (mm) | 250 |
| Column internal diameter (mm) | 4.6 |
| Column particle size (micron) | 5 |

An isocratic elution was used:

| Time (min) | % A | % B |
|---|---|---|
| 50.00 | 90 | 10 |

Preparative HPLC Methods:

Preparative HPLC Method 1

Purification was carried out using a Waters PHP-01 Preparative HPLC system using an X Bridge C18 (250 mm length×19 mm internal diameter) column with 5 micron particle size and a flow rate of 15 mL/min. Solvent system used: mobile phases (A) 0.1% ammonia in 100% water and (B) 100% acetonitrile using the following gradient:

| Time (min) | % A | % B |
|---|---|---|
| 0.01 | 70 | 30 |
| 14.00 | 20 | 80 |
| 14.01 | 0 | 100 |
| 16.00 | 0 | 100 |
| 16.01 | 70 | 30 |
| 17.00 | 70 | 30 |

Preparative HPLC Method 2

Purification was carried out using a Waters PHP-01 Preparative HPLC system using an X Bridge C18 (250 mm length×30 mm internal diameter) column with 5 micron particle size and a flow rate of 30 mL/min. Solvent system used: mobile phases (A) 0.1% ammonia in 100% water and (B) 100% acetonitrile using the following gradient:

| Time (min) | % A | % B |
|---|---|---|
| 0.01 | 75 | 25 |
| 16.00 | 20 | 80 |
| 16.01 | 0 | 100 |
| 17.00 | 0 | 100 |
| 17.01 | 75 | 25 |
| 18.00 | 75 | 25 |

Preparative HPLC Method 3

| Parameter | Information |
|---|---|
| chiral HPLC equipment | Waters PHP-01 (2487) |
| Column flow (mL/min) | 22 |
| Eluent solvents (mobile phase) | (A) 10 mM $NH_4HCO_3$ in water (B) acetonitrile:methanol:isopropyl alcohol (65:25:10) |
| Column supplier | Waters |
| Column name | X BRIDGE C18 column |
| Column length (mm) | 250 |
| Column internal diameter (mm) | 30 |
| Column particle size (micron) | 5 |

Elution Gradient:

| Time (min) | % A | % B |
|---|---|---|
| 0.01 | 70 | 30 |
| 6.00 | 54 | 46 |
| 6.01 | 54 | 46 |
| 23.00 | 54 | 46 |
| 23.01 | 0 | 100 |
| 25.00 | 0 | 100 |
| 25.01 | 70 | 30 |
| 26.00 | 70 | 30 |

Preparative HPLC Method 4

| Parameter | Information |
|---|---|
| chiral HPLC equipment | Waters PHP-01 (2487) |
| Column flow (mL/min) | 22 |
| Eluent solvents (mobile phase) | (A) 10 mM $NH_4HCO_3$ in water (B) acetonitrile:methanol:isopropyl alcohol (65:25:10) |
| Elution gradient | See below |
| Column supplier | Waters |
| Column name | Grace Alltech Denali C18 Reversed Phase Column |
| Column length (mm) | 250 |
| Column internal diameter (mm) | 25 |
| Column particle size (micron) | 5 |

Elution Gradient:

| Time (min) | A | B |
|---|---|---|
| 0.01 | 65 | 35 |
| 7.00 | 65 | 35 |
| 26.00 | 45 | 55 |
| 26.01 | 0 | 100 |
| 27.00 | 0 | 100 |
| 27.01 | 65 | 35 |
| 28.00 | 65 | 35 |

Preparative HPLC Method 5

| Parameter | Information |
|---|---|
| chiral HPLC equipment | Waters PHP-01 (2487) |
| Column flow (mL/min) | 22 |
| Eluent solvents (mobile phase) | (A) 10 mM $NH_4HCO_3$ in water (B) 100% acetonitrile |
| Elution gradient | See below |
| Column supplier | Waters |
| Column name | Grace Alltech Denali C18 Reversed Phase Column |
| Column length (mm) | 250 |
| Column internal diameter (mm) | 25 |
| Column particle size (micron) | 5 |

Elution Gradient:

| Time (min) | A | B |
|---|---|---|
| 0.01 | 70 | 30 |
| 3.00 | 50 | 50 |
| 22.00 | 50 | 50 |
| 22.01 | 0 | 100 |
| 23.00 | 0 | 100 |
| 23.01 | 70 | 30 |
| 24.00 | 70 | 30 |

Preparative HPLC Method 6

The same method was used as for Preparative HPLC method 5 except that the following elution gradient was used:

| Time (min) | % A | % B |
|---|---|---|
| 0.01 | 90 | 10 |
| 3.00 | 53 | 47 |
| 22.00 | 50 | 50 |
| 22.01 | 0 | 100 |
| 23.00 | 0 | 100 |
| 23.01 | 90 | 10 |
| 24.00 | 90 | 10 |

Preparative HPLC Method 7

The same method was used as for Preparative HPLC method 5 except that the following elution gradient was used:

| Time (min) | % A | % B |
|---|---|---|
| 0.01 | 90 | 10 |
| 3.00 | 63 | 37 |
| 16.00 | 58 | 42 |
| 16.01 | 0 | 100 |
| 17.00 | 0 | 100 |
| 17.01 | 90 | 10 |
| 18.00 | 90 | 10 |

Synthetic Scheme A

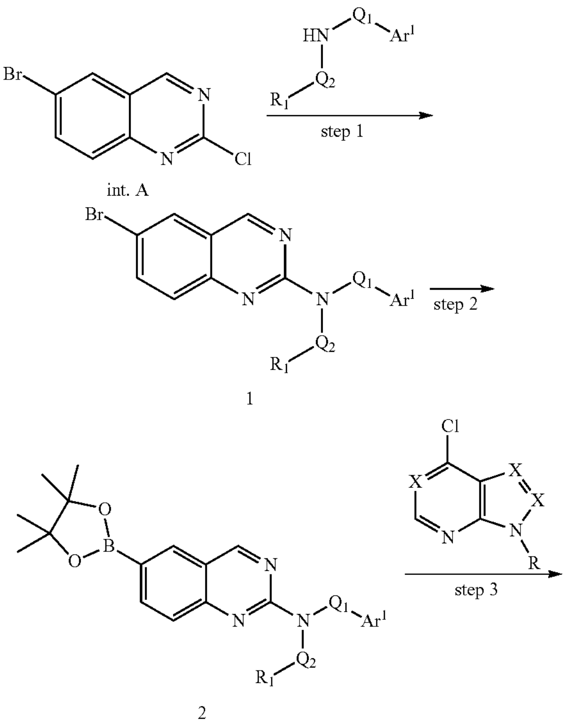

int. A

1

2

-continued

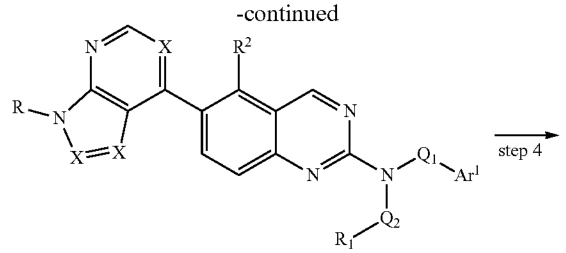

3

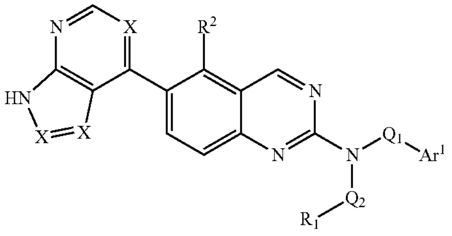

4

Int A is commercially available and can also be synthesized by methods described in the literature (Jain, Rama et al, PCT International Application WO2009153313)

Where X═CH or N and where R=protecting group such as THP

Compound 4 may be isolated as the free base or a salt form, e.g. monohydrochloride salt, depending on the method of isolation used.

Synthetic scheme B

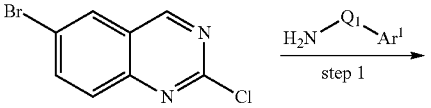

int. A

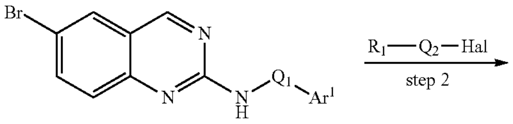

1

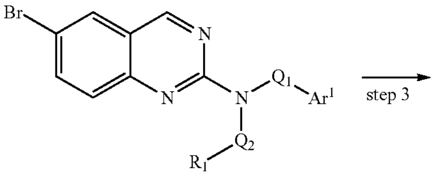

2

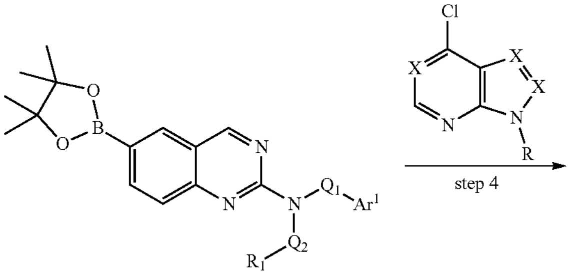

3

-continued

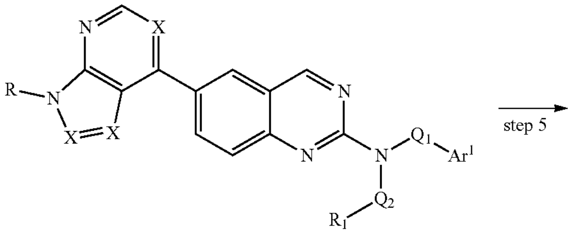

4

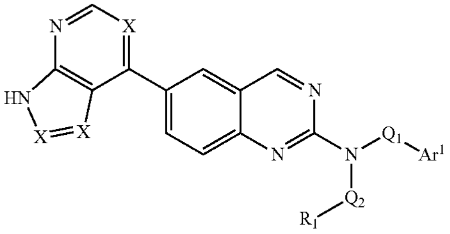

5

Where X═CH or N and where R=protecting group such as THP

Compound 5 may be isolated as the free base or a salt form e.g. monohydrochloride salt depending on the method of isolation used.

Synthetic scheme C

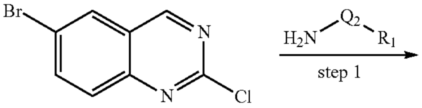

int. A

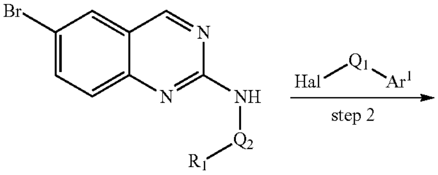

1

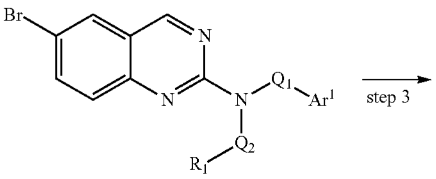

2

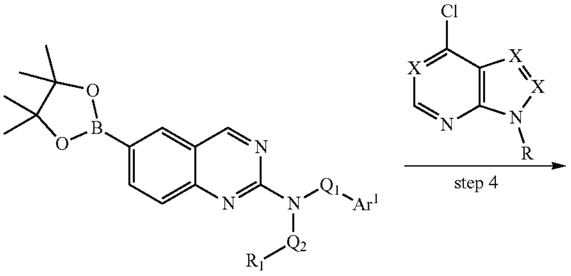

3

-continued

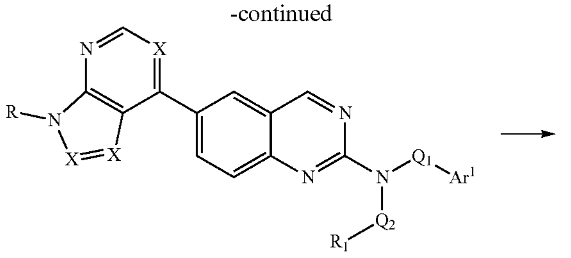

4

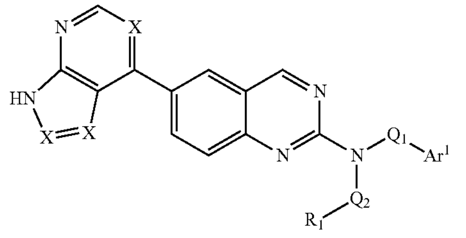

5

Where X═CH or N and where R=protecting group such as THP

Compound 5 may be isolated as the free base or a salt form, e.g. monohydrochloride salt, depending on the method of isolation used.

Synthesis of Intermediates

Intermediate A: 6-Bromo-2-chloro-quinazoline

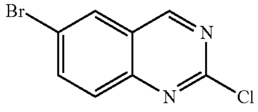 [SMILES: Clc1ncc2cc(Br)ccc2n1]

A suspension of 6-Bromo-quinazolin-2-ol (2 g, 8.89 mmol) in $POCl_3$ (20 mL) was stirred at 110° C. for 5 h. After completion of the reaction, the reaction mixture was concentrated in vacuo and the residue was slowly poured into ice, resulting in a solid precipitate. The solid was filtered, washed with water followed by hexanes and then dried in vacuo to afford the title product (1.5 g, 69%).

6-Bromo-quinazolin-2-ol is commercially available and can also be synthesized by methods described in the literature (Jain, Rama et al, PCT Int. Appl., 2009153313)

Intermediate B: 4-Chloro-1-(tetrahydro-pyran-2-yl)-1H-pyrazolo[3,4-d]pyrimidine

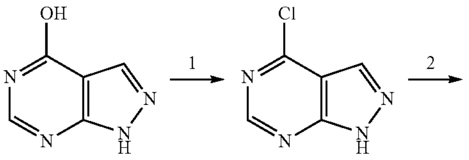

-continued

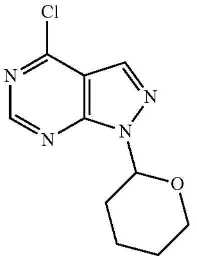

B

Step 1: 4-Chloro-1H-pyrazolo[3,4-d]pyrimidine

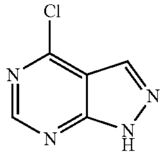

1H-Pyrazolo [3,4-d]pyrimidin-4-ol (5.0 g, 36.7 mmol) was dissolved in $POCl_3$ (61.2 mL, 100.67 g, 657 mmol) at room temperature under nitrogen. N,N-diisopropyl ethylamine (10.2 mL, 58.5 mmol) was added into the reaction mixture and the resulting mixture was refluxed at 110° C. for 4 hrs. After 4 hrs, $POCl_3$ was distilled off under vacuum at 40° C. to obtain a blackish red thick gum. The thick gum was poured into ice cold water (25 mL) and extracted by DCM (25 mL×3). The organic layer was concentrated to 25 mL. The product was used as crude for the next step.

Step 2: 4-Chloro-1-(tetrahydro-pyran-2-yl)-1H-pyrazolo[3,4-d]pyrimidine

To a solution of 4-chloro-1H-pyrazolo[3,4-d]pyrimidine (2 g, 12.9 mmol) and D-10-Camphor sulphonic acid (0.324 g, 1.39 mmol) in anhydrous ethyl acetate (20 mL) was slowly added 3,4-dihydropyrane (6 mL, 5.53 g, 65.8 mmol) at room temperature. The reaction mixture was then allowed to stir at room temperature for 24 h. After completion of reaction, as judged by TLC, the reaction mixture was concentrated in vacuo and purified by flash column chromatography on silica gel eluting with 10% ethyl acetate in hexanes to afford the title product (1.92 g, 62%).

Intermediate C: N'-Benzyl-N,N-dimethyl-ethane-1,2-diamine

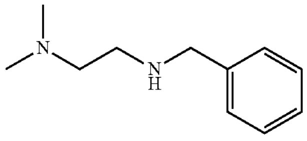

To a stirred solution of Benzaldehyde (1.0 g, 9.42 mmol) in methanol (20 mL) was added N,N dimethyl ethylene diamine (0.83 g, 9.42 mmol) and glacial acetic acid (1.13 g, 1.18 mmol) at RT under nitrogen. The mixture was stirred at RT for 2 h. To the reaction mixture was added sodium triacetoxyborohydride (5.99 g, 2.83 mmol) at 0° C. and the reaction mixture was stirred for 18 h at RT under nitrogen. The reaction mixture was concentrated in vacuo. Then to the crude was added 20 ml 1N HCl and the aqueous was extracted with ethyl acetate (20 mL). The aqueous layer was separated off, basified to pH 8 with solid $NaHCO_3$ and extracted with DCM (7×30 mL). The DCM layer was separated off, dried over $Na_2SO_4$ and concentrated in vacuo to afford title product (1.0 g, 60%).

Intermediate D: (R)-3-Aminomethyl-morpholine-4-carboxylic Acid Tert-Butyl Ester

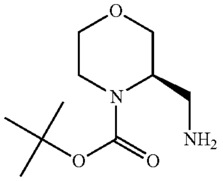

Step 1: (R)-3-(1,3-Dioxo-1,3-dihydro-isoindol-2-ylmethyl)-morpholine-4-carboxylic Acid Tert-Butyl Ester

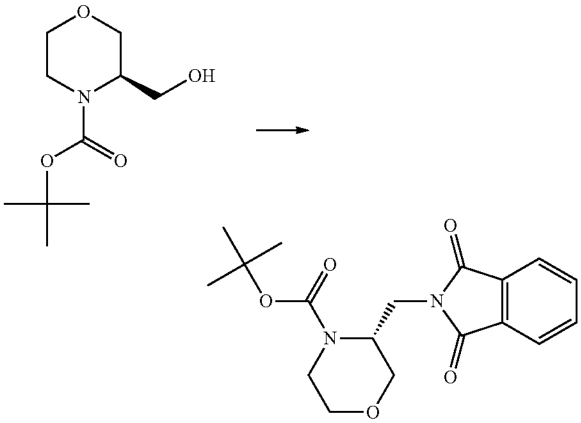

To a solution of (R)-4-Boc-3-hydroxymethylmorpholine (1.5 g, 6.90 mmol) in THF (7.5 mL) was added phthalimide (1.21 g, 8.22 mmol) and triphenylphosphine (5.43 g, 20.70 mmol) at RT. To the reaction mixture was added a solution of Diisopropylazodicarboxylate (DIAD) (4.18 g, 0.0207 mol) in THF (7.5 mL) dropwise and the reaction mixture was stirred at RT for 30 min. The reaction mixture was poured into water and extracted with ethyl acetate (3×50 mL). The organic layer was then washed with brine (1×30 mL) as well as water (1×30 mL), dried over anhydrous sodium sulphate and concentrated in vacuo. The residue was further purified by column chromatography on silica gel, eluting with 16% ethyl acetate in hexane to afford an oil (4.3 g, >100%).

Step 2: (R)-3-Aminomethyl-morpholine-4-carboxylic Acid Tert-Butyl Ester

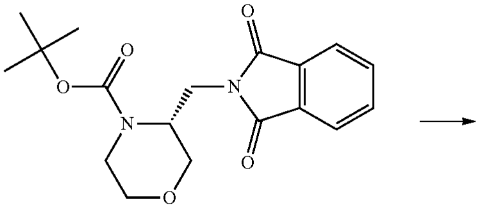

-continued

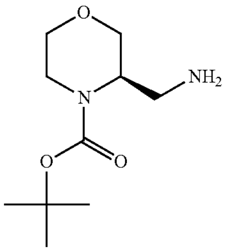

To a solution of (R)-3-(1,3-Dioxo-1,3-dihydro-isoindol-2-ylmethyl)-morpholine-4-carboxylic acid tert-butyl ester (4.3 g, 12.4 mmol) in ethanol (26 mL) and toluene (26 mL) was added hydrazine hydrate (99% in water, 1.19 g, 23.53 mmol) at RT. The reaction mixture was refluxed for 30 min, concentrated in vacuo, and the residue was poured into ice-water and extracted with ethyl acetate (3×100 mL). The organic layers were combined and washed with brine, separated off and dried over sodium sulphate, then concentrated in vacuo to afford crude product. The crude product was further purified by flash column chromatography on silica gel, eluting with 4% methanol in chloroform to afford the title product (1.63 g, 61%).

Intermediate E: (S)-3-Aminomethyl-morpholine-4-carboxylic Acid Tert-Butyl Ester

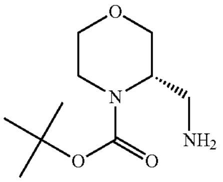

Intermediate E was prepared from (S)-4-Boc-3-hydroxymethylmorpholine using the same method as described for intermediate D.

Intermediate F: 6-Chloro-9-(tetrahydro-pyran-2-yl)-9H-purine

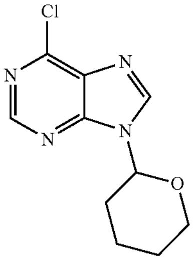 [SMILES: Clc1ncnc2c1ncn2C1CCCCO1]

Intermediate F is commercially available (CAS No.: 7306-68-5).

Intermediate G: 4-Chloro-3-methyl-1-(tetrahydro-pyran-2-yl)-1H-pyrazolo[3,4d]pyrimidine

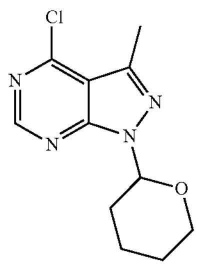 [SMILES: Cc1nn(C2CCCCO2)c2ncnc(Cl)c12]

To a suspension of 4-chloro-3-methyl-1H-pyrazolo[3,4-d]pyrimidine (0.5 g, 2.97 mmol) in ethyl acetate (21 mL) was sequentially added D-10 camphor sulfonic acid (0.07 g, 0.301 mmol) and 3,4-dihydropyran (1.24 g, 14.7 mmol) at RT. The reaction mixture was stirred for 24 h at RT and was then concentrated in vacuo prior to purification by flash column chromatography on silica, eluting with 8% ethyl acetate in hexane to afford title product (0.59 g, 79%).

Intermediate H: N-{3-[(6-Bromo-quinazolin-2-ylamino)-methyl]-phenyl}-methanesulfonamide

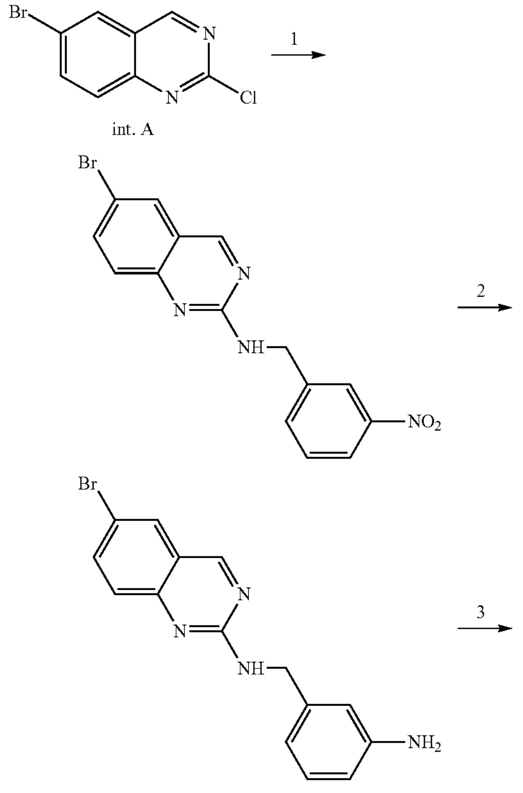

-continued

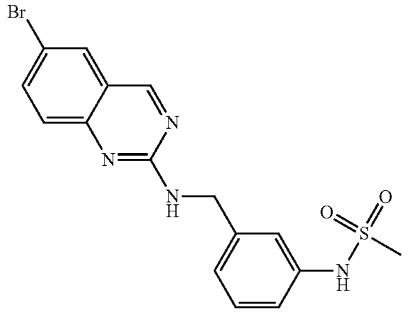

Step 1: (6-Bromo-quinazolin-2-yl)-(3-nitro-benzyl)-amine

To a stirred solution of 6-bromo-2-chloro-quinazoline (0.6 g, 2.46 mmol) in DMSO (6 mL) was added 3-nitrobenzylamine hydrochloride (0.56 g, 2.97 mmol) and DIPEA (1.28 g, 1.73 mL, 9.89 mmol) at RT. The resulting mixture was heated at 80° C. for 12 h. The reaction mixture was poured into cold water and extracted with ethyl acetate (2×50 mL). The organic layer was washed with brine (20 mL) then water (20 mL), separated off, dried over anhydrous sodium sulphate and concentrated in vacuo to afford crude product. The crude product was purified by flash column chromatography on silica gel, eluting with 18% ethyl acetate in hexane to afford the title product (0.97 g, >100%).

Step 2: (3-Amino-benzyl)-(6-bromo-quinazolin-2-yl)-amine

To a stirred solution of (6-Bromo-quinazolin-2-yl)-(3-nitro-benzyl)-amine (0.97 g, 2.70 mmol) in methanol (10 mL) was added glacial acetic acid (0.30 g, 5.0 mmol) and Iron powder (100 mesh) (0.30 g, 5.4 mmol) at RT. The resulting mixture was heated at 60° C. for 4 h. The reaction mixture was poured into cold water and extracted with ethyl acetate (2×50 mL). The organic layer was washed with brine (20 mL) then water (20 mL), separated off, dried over anhydrous sodium sulphate and concentrated in vacuo to afford crude product which was used directly in the next step.

Step 3: N-{3-[(6-Bromo-quinazolin-2-ylamino)-methyl]-phenyl}-methanesulfonamide

To a stirred solution of (3-Amino-benzyl)-(6-bromo-quinazolin-2-yl)-amine (0.85 g, 2.58 mmol) in DCM (13 mL) was added 2,6-lutidine (0.30 g, 0.33 mL, 2.80 mmol) and methane sulphonyl chloride (0.29 g, 0.196 mL, 2.53 mmol) at 00° C. The resulting mixture was then stirred for 6 h at RT. The reaction mixture was poured into cold water and extracted with ethyl acetate (2×50 mL). The organic layer was washed with brine (20 mL) then water (20 mL), separated off, dried over anhydrous sodium sulphate and concentrated in vacuo to afford crude product. The crude product was purified by flash column chromatography on silica gel, eluting with 40% ethyl acetate in hexane to afford the title product (0.6 g, 57%).

Intermediate I: N-{3-[(R)-1-(6-Bromo-quinazolin-2-ylamino)-ethyl]-phenyl}-methanesulfonamide

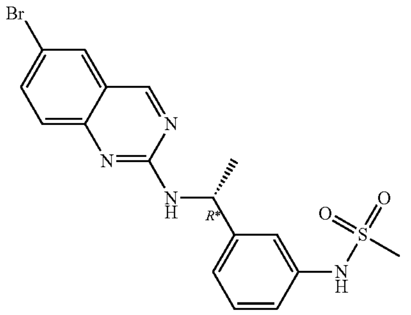 [SMILES: C[C@@H](Nc1ncc2cc(Br)ccc2n1)c1cccc(NS(C)(=O)=O)c1]

The title compound was prepared using the same method as described for intermediate H, with the exception that (R)-1-(3-nitrophenyl)ethylamine hydrochloride (0.70 g, 3.45 mmol) was used instead of 3-nitrobenzylamine hydrochloride in step 1. Yield of final step: 0.7 g (57%).

Synthetic scheme A is illustrated with reference to Example 1 below.

Example 1

((R)-1-Phenyl-ethyl)-[6-(1H-pyrazolo[3,4-d]pyrimidin-4-yl)-quinazolin-2-yl]-amine

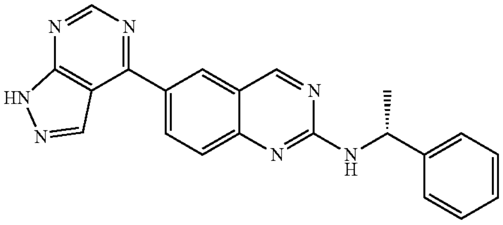 [SMILES: C[C@@H](Nc1ncc2cc(-c3ncnc4[nH]ncc34)ccc2n1)c1ccccc1]

Step 1: (6-Bromo-quinazolin-2-yl)-((R)-1-phenyl-ethyl)-amine

To a solution of 6-Bromo-2-chloro-quinazoline (10 g, 41.07 mmol) in DMSO (100 mL) was added (R)-(+)-1-phenylethylamine (6.0 g, 49.51 mmol) and DIPEA (21.4 g, 28.84 mL, 166 mmol). The resulting mixture was heated at 80° C. for 12 h. The reaction mixture was poured into cold water resulting in a solid precipitate. The solid was collected in vacuo and washed with cold water (3×100 mL) to afford title product which was used in the next step without purification (13.2 g, 98%).

Step 2: ((R)-1-Phenyl-ethyl)-[6-(4,4,5,5-tetramethyl-[1,3,2]dioxaborolan-2-yl)-quinazolin-2-yl]-amine To a stirred solution of (6-Bromo-quinazolin-2-yl)-((R)-1-phenyl-ethyl)-amine (13.2 g, 40.22 mol) in 1, 4-dioxane (149 mL) was added bis(pinacolato)diborane (17.4 g, 68.52 mmol) followed by potassium acetate (11.8 g, 120.2 mmol) under nitrogen at RT. Nitrogen gas was bubbled through the resulting mixture for 30 min. To the reaction mixture was then added 1, 1-bis(diphenylphosphino)ferrocene palladium (II)dichloride dichloromethane complex (1.6 g, 1.96 mmol). The reaction mixture was then heated at 80° C. for 3 h. The reaction mixture was poured into water and extracted with ethyl acetate (3×200 mL). The organic layers were combined and washed with brine (100 mL) followed by water (100 mL), then separated off and dried over anhydrous sodium sulphate. The organic layer was concentrated in vacuo then purified by flash column chromatography on silica eluting with 15% ethyl acetate in hexanes to afford title product which was used in the next step without further purification (19.9 g, >100%).

Step 3: ((R)-1-Phenyl-ethyl)-{6-[1-(tetrahydro-pyran-2-yl)-1H-pyrazolo[3,4-d]pyrimidin-4-yl]-quinazolin-2-yl}-amine To a solution of ((R)-1-Phenyl-ethyl)-[6-(4,4,5,5-tetramethyl-[1,3,2]dioxaborolan-2-yl)-quinazolin-2-yl]-amine (19.9 g, 67.89 mmol) in a mixture of THF: water (267 mL, 4:1 ratio) was added Intermediate B (19.4 g, 81.28 mmol) followed by $Cs_2CO_3$ (88.3 g, 271.01 mmol) under nitrogen at RT. Nitrogen gas was bubbled through the resulting mixture for 45 min and to the reaction mixture was then added tetrakis(triphenylphosphine)palladium (0) (7.84 g, 6.78 mmol). The reaction mixture was then heated at 80° C. for 4 h under nitrogen. The reaction mixture was poured into water and extracted with ethyl acetate (2×300 mL). The organic layers were combined and washed with water (100 mL), separated off then dried over anhydrous sodium sulphate. The organic layer was concentrated in vacuo then purified by flash column chromatography on silica eluting with 45% ethyl acetate in hexanes to afford title product (15 g, 49%).

Step 4: ((R)-1-Phenyl-ethyl)-[6-(1H-pyrazolo[3,4-d]pyrimidin-4-yl)-quinazolin-2-yl]-amine To a stirred solution of ((R)-1-Phenyl-ethyl)-{6-[1-(tetrahydro-pyran-2-yl)-1H-pyrazolo[3,4-d]pyrimidin-4-yl]-quinazolin-2-yl}-amine (15.0 g, 33.2 mol) in a mixture of methanol (36 mL) and 1,4-dioxane (150 mL) was added 4N HCl in 1,4-dioxane (41.5 mL) under nitrogen at RT. The reaction mixture was further stirred for 3 h at RT.

The reaction mixture was filtered in vacuo, and the filtered solid was washed with ethyl acetate (3×50 mL) then hexane (3×50 mL) to afford the HCl salt. The solid was added to water (100 mL) and the resulting mixture was basified to pH 8.3 using saturated aqueous $NaHCO_3$ solution. The resulting suspension was stirred for 30 min at RT then filtered in vacuo. The solid was re-suspended in water on a Büchner funnel and the resulting slurry was stirred for 10 mins and then filtered in vacuo. The slurrying in water process was repeated a further seven times. The resulting filtered solid was dried in vacuo to afford the title product (9.0 g, 74%).

Optionally, it is possible to retain the title compound as the HCl salt by omitting the final basification procedure.

Example 2

((R)-1-(3-Chloro-phenyl)-ethyl)-[6-(1H-pyrazolo[3,4-d]pyrimidin-4-yl)-quinazolin-2-yl]-amine The title product was prepared from intermediate A (0.4 g, 1.64 mmol) using the same method as described for Example 1 with the following exceptions: (a) (R)-1-(3-chloro-phenyl)-ethylamine was used instead of (R)-1-phenyl-ethylamine in Step 1 (b) in step 4, the following method was used: N—((R)-1-(3-chlorophenyl)ethyl)-6-(1-(tetrahydro-2H-pyran-2-yl)-1H-pyrazolo[3,4-d]pyrimidin-4-yl)quinazolin-2-amine (0.12 g, 0.247 mmol) was dissolved in methanol (1 mL) and 4 N HCl in dioxane (3 mL) was added at RT. After stirring at RT for 4 h, the solid precipitate thus formed was filtered and washed with ethyl acetate to afford title product as the monohydrochloride salt (0.050 g, 46%).

Example 3

((R)-1-(3-Fluoro-phenyl)-ethyl)-[6-(1H-pyrazolo[3,4-d]pyrimidin-4-yl)-quinazolin-2-yl]-amine The title product was prepared from intermediate A (0.4 g, 1.64 mmol) using the same method as described for Example 1 with the following exceptions: (a) (R)-1-(3-fluoro-phenyl)-ethylamine was used instead of (R)-1-phenyl-ethylamine in step 1 (b) in step 4, the method described for example 2 was used resulting in the compound being isolated as the monohydrochloride salt (0.040 g, 68%).

Example 4

((R)-1-(4-Fluoro-phenyl)-ethyl)-[6-(1H-pyrazolo[3,4-d]pyrimidin-4-yl)-quinazolin-2-yl]-amine The title product was prepared from intermediate A (0.35 g, 1.43 mmol) using the same method as described for Example 1 with the following exceptions: (a) (R)-1-(4-fluoro-phenyl)-ethylamine was used instead of (R)-1-phenyl-ethylamine in step 1 (b) in step 4, following concentration of the reaction mixture in vacuo, the crude product was purified by preparative HPLC purification to afford the title product (0.020 g, 22%).

Example 5

((S)-2-Hydroxy-1-phenyl-ethyl)-[6-(1H-pyrazolo[3,4-d]pyrimidin-4-yl)-quinazolin-2-yl]-amine The title product was prepared from intermediate A (0.4 g, 1.64 mmol) using the same method as described for Example 1 with the following exceptions: (a) (S)-2-phenylglycinol was used instead of (R)-1-phenyl-ethylamine in step 1 (b) in step 4, following concentration of the reaction mixture in vacuo, the crude product was purified by preparative HPLC purification to afford the free base. To a solution of free base in ethyl acetate (1 ml) at 10° C. was added 4N HCl in dioxane (0.05 ml) followed by stirring at RT for 30 min. After 30 min, the reaction mixture was concentrated in vacuo and triturated with ethyl acetate to afford the title product as the monohydrochloride salt (0.050 g, 37%).

Example 6

(4-Fluorobenzyl)-[6-(1H-pyrazolo[3,4-d]pyrimidin-4-yl)-quinazolin-2-yl]-methylamine The title product was prepared from intermediate A (0.4 g, 1.64 mmol) using the same method as described for Example 1 with the following exceptions: (a) N-(4-fluorobenzyl)-N-methylamine was used instead of (R)-1-phenyl-ethylamine in step 1 (b) in step 4, following concentration of the reaction mixture in vacuo, the product was triturated with methanol and ethyl acetate to afford the title product as the monohydrochloride salt (0.080 g, 59%).

Example 7

Benzyl-[6-(1H-pyrazolo[3,4-d]pyrimidin-4-yl)-quinazolin-2-yl]-methylamine

The title product was prepared from intermediate A (0.6 g, 2.46 mmol) using the same method as described for Example 1 with the following exceptions: (a) N-benzyl-N-methylamine was used instead of (R)-1-phenyl-ethylamine in step 1 (b) in step 4, the method of example 6 was applied. The title product was isolated as the monohydrochloride salt (0.080 g, 60%).

Example 8

((R)-1-Phenyl-ethyl)-[6-(1H-pyrazolo[3,4-d]pyrimidin-4-yl)-quinazolin-2-yl]-methylamine The title product was prepared from intermediate A and by following scheme B and the method described below.

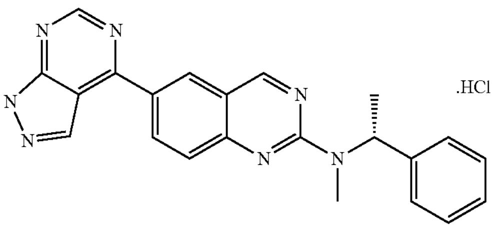 [SMILES: C[C@H](c1ccccc1)N(C)c1ncc2cc(-c3ncnc4[nH]ncc34)ccc2n1 ; ".HCl"]

Step 1: (6-Bromo-quinazolin-2-yl)-((R)-1-phenyl-ethyl)-amine

As described in step 1 of Example 1

Step 2: (6-Bromo-quinazolin-2-yl)-methyl-((R)-1-phenyl-ethyl)-amine

To a suspension of NaH (60% in mineral oil) (0.082 g, 2.05 mmol) in DMF (5 mL) at 0° C. under nitrogen was added a solution of (6-Bromo-quinazolin-2-yl)-((R)-1-phenyl-ethyl)-amine (0.45 g, 1.37 mmol) in DMF (5 mL). The reaction mixture was stirred at 0° C. for 30 minutes. MeI (0.233 g, 1.64 mmol) was added and the reaction mixture was stirred at RT for 2 h. The reaction mixture was then diluted with water (30 mL) and extracted with ethyl acetate (2×30 mL). The combined organic layers were separated off, dried over anhydrous sodium sulphate, the concentrated in vacuo to afford crude product. The crude product was purified by flash column chromatography on silica gel eluting with 5-8% ethyl acetate in hexanes to afford the title product (0.45 g, 96%).

Step 3: Methyl-((R)-1-phenyl-ethyl)-[6-(4,4,5,5-tetramethyl-[1,3,2]dioxaborolan-2-yl)-quinazolin-2-yl]-amine (6-Bromo-quinazolin-2-yl)-methyl-((R)-1-phenyl-ethyl)-amine (0.45 g, 1.31 mmol) was subjected to the conditions of step 2, Example 1 to afford the title product (0.25 g, 49%).

Step 4: Methyl-((R)-1-phenyl-ethyl)-{6-[1-(tetrahydro-pyran-2-yl)-1H-pyrazolo[3,4-d]pyrimidin-4-yl]-quinazolin-2-yl}-amine Methyl-((R)-1-phenyl-ethyl)-[6-(4,4,5,5-tetramethyl-[1,3,2]dioxaborolan-2-yl)-quinazolin-2-yl]-amine (0.25 g, 0.64 mmol) was subjected to the conditions of step 3, Example 1 to afford the title product (0.1 g, 34%).

Step 5: ((R)-1-Phenyl-ethyl)-[6-(1H-pyrazolo[3,4-d]pyrimidin-4-yl)-quinazolin-2-yl]-methylamine To a solution of Methyl-((R)-1-phenyl-ethyl)-{6-[1-(tetrahydro-pyran-2-yl)-1H-pyrazolo[3,4-d]pyrimidin-4-yl]-quinazolin-2-yl}-amine (0.1 g, 0.21 mmol) in methanol (3 mL) was added 4N HCl in dioxane (2 mL) at RT and the reaction mixture was stirred at RT for 5 h. During the reaction a solid precipitated out; the solid was thus filtered in vacuo and washed with ethyl acetate then dried in vacuo to afford the title product (0.080 g, 91%).

The compound is isolated as the monohydrochloride salt.

Example 9

(4-Fluorobenzyl)-[6-(1H-pyrazolo[3,4-d]pyrimidin-4-yl)-quinazolin-2-yl]-amine

The title product was prepared from intermediate A (1.2 g, 4.96 mmol) using the same method as described for Example 1 with the following exceptions: (a) 4-fluorobenzylamine was used instead of (R)-1-phenyl-ethylamine in step 1 (b) in step 4, following treatment with 4N HCl in dioxane (6.0 mL) and stirring for 3 h, the reaction mixture was concentrated in vacuo, poured into water and the resulting reaction mixture was basified up to pH 8 using saturated bicarbonate (aq) solution. The resulting suspension was filtered in vacuo to afford title product. Yield of final step: 0.105 g (48%).

Example 10

(3-Fluorobenzyl)-[6-(1H-pyrazolo[3,4-d]pyrimidin-4-yl)-quinazolin-2-yl]-amine

The title product was prepared from intermediate A (1.0 g, 4.13 mmol) using the same method as described for Example 1 with the following exceptions: (a) 3-fluorobenzylamine was used instead of (R)-1-phenyl-ethylamine in step 1 (b) in step 4, the method of isolation described in example 9 was used but additionally the filtered product was suspended in ethyl acetate (5 mL) for 15 min at RT, followed by filtration in vacuo. Yield of final step: 0.112 g (34%).

Example 11

(3-Chlorobenzyl)-[6-(1H-pyrazolo[3,4-d]pyrimidin-4-yl)-quinazolin-2-yl]-amine

The title product was prepared from intermediate A (0.60 g, 2.48 mmol) using the same method as described for Example 1 with the following exceptions: (a) 3-chlorobenzylamine was used instead of (R)-1-phenyl-ethylamine in step 1 (b) in step 4, the method of isolation described in example 9 was used but additionally the filtered product was further purified by preparative HPLC purification using preparative HPLC method 1. Yield of final step: 0.036 g (17%).

Example 12

((R)-1-Phenyl-ethyl)-[7-(1H-pyrazolo[3,4-d]pyrimidin-4-yl)-quinazolin-2-yl]-amine The title product was prepared using the same method as described for Example 1 with the following exceptions: (a) 7-bromo-quinazolin-2-ol (1.2 g, 4.96 mmol) was used instead of 6-bromo-quinazolin-2-ol in the synthesis of Int. A (b) in step 4, reaction time was 1 h. The method of isolation described in example 9 was used but the filtered solid was furthermore purified by flash column chromatography, eluting with 3% methanol in chloroform, followed by preparative HPLC purification using preparative HPLC method 2. Yield of final step: 0.022 g (17%).

7-Bromo-quinazolin-2-ol can be purchased from various commercial sources, as indicated by availability on Scifinder databases, or can be prepared via the route described in International patent application WO2007117607.

Example 13

((R)-1-Phenyl-ethyl)-[6-(1H-pyrazolo[3,4-b]pyridin-4-yl)-quinazolin-2-yl]-amine

The title product was prepared from ((R)-1-Phenyl-ethyl)-[6-(4,4,5,5-tetramethyl-[1,3,2]dioxaborolan-2-yl)-quinazolin-2-yl]-amine (0.3 g, 0.799 mmol) using the same method as described for Example 1 with the following exceptions: (a) in step 3, 4-chloro-1H-pyrazolo[3,4-b]pyridine was used instead of intermediate B. Furthermore, in step 3, a solvent mixture of DMF: water was used (4:1, 5 mL) and heating took place at 130° C. in a microwave reactor. Step 4 was a HCl salt formation step: to a suspension of ((R)-1-Phenyl-ethyl)-[6-(1H-pyrazolo[3,4-b]pyridin-4-yl)-quinazolin-2-yl]-amine (0.080 g, 0.218 mmol) in ethyl acetate (0.8 mL) was added 4N HCl in dioxane (0.08 mL) at 10° C. and the reaction mixture was stirred at the same temperature for 40 min. The reaction mixture was then concentrated in vacuo and triturated with ethyl acetate to afford the title product as the monohydrochloride salt (0.070 g, 80%)

4-Chloro-1H-pyrazolo[3,4-b]pyridine can be purchased from various commercial sources.

Example 14

((R)-1-Phenyl-ethyl)-[6-(7H-pyrrolo[2,3-d]pyrimidin-4-yl)-quinazolin-2-yl]-amine The title product was prepared from ((R)-1-Phenyl-ethyl)-[6-(4,4,5,5-tetramethyl-[1,3,2]dioxaborolan-2-yl)-quinazolin-2-yl]-amine (0.35 g, 0.933 mmol) using the same method as described for Example 1 with the following exceptions: (a) 4-chloro-7H-pyrrolo[2,3-d]pyrimidine was used in step 3 instead of intermediate B (b) a HCl salt formation step was included, the method for which is described in example 13 The compound is isolated as the monohydrochloride salt (0.055 g, 83%).

4-Chloro-7H-pyrrolo[2,3-d]pyrimidine can be purchased from various commercial sources.

Example 15

((R)-1-Phenyl-ethyl)-[6-(1H-pyrrolo[2,3-b]pyridin-4-yl)-quinazolin-2-yl]-amine

The title product was prepared from ((R)-1-Phenyl-ethyl)-[6-(4,4,5,5-tetramethyl-[1,3,2]dioxaborolan-2-yl)-quinazolin-2-yl]-amine (0.20 g, 0.533 mmol) using the same method as described for Example 1 with the following exceptions: (a) in step 3, 4-bromo-1H-pyrrolo[2,3-b]pyridine was used instead of intermediate B, potassium carbonate was used instead of cesium carbonate, and dioxane: water (4:1) was used as solvent rather than THF: water (b) a HCl salt formation step was included, the method for which is described in example 13. The compound is isolated as the monohydrochloride salt (0.070 g, 80%).

4-Bromo-1H-pyrrolo[2,3-b]pyridine can be purchased from various commercial sources.

Example 16

N-Benzyl-N',N'-dimethyl-N-[6-(1H-pyrazolo[3,4-d]pyrimidin-4-yl)-quinazolin-2-yl]-ethane-1,2-diamine The title compound can be prepared via Synthetic Scheme A, following the method of example 1, using N'-Benzyl-N,N-dimethyl-ethane-1,2-diamine (intermediate C) in step 1.

In step 4, the following method was followed:

Step 4

To a stirred solution of N-Benzyl-N',N'-dimethyl-N-{6-[1-(tetrahydro-pyran-2-yl)-1H-pyrazolo[3,4-d]pyrimidin-4-yl]-quinazolin-2-yl}-ethane-1,2-diamine (0.40 g, 0.79 mmol) in 1,4-dioxane (4 mL) was added 4N HCl in 1,4-dioxane (0.25 mL, 1.0 mmol) under nitrogen at RT. The reaction mixture was further stirred for 4 h at RT. An additional aliquot of 4N HCl in 1,4-dioxane (0.25 mL, 1.0 mol) was added and the reaction mixture was stirred for 3 h at RT. The reaction mixture was then concentrated in vacuo to afford crude product which was added to water. The resulting mixture was basified with saturated $NaHCO_3$ (aq) solution to pH 8. The resulting mixture was extracted by ethyl acetate and then concentrated in vacuo. The residue was purified by flash chromatography on silica gel, eluting with 2.5% methanol in chloroform to afford a crude yellow solid which was further triturated using diethyl ether. The solid recovered from trituration (0.086 g, 0.189 mmol) was dissolved in 1,4-dioxane (0.8 mL) at room temperature and 4M HCl in 1,4-dioxane (0.06 mL, 0.24 mmol) was added. The reaction mixture was stirred for 30 minutes at RT, after which the reaction mixture was concentrated in vacuo and triturated with diethyl ether (1 mL) to afford title product as the monohydrochloride salt (0.067 g, 19% overall yield).

Example 17

Benzyl-(R)-1-morpholin-3-ylmethyl-[6-(1H-pyrazolo[3,4-d]pyrimidin-4-yl)-quinazolin-2-yl]-amine The title compound was prepared according to Synthetic Scheme C.

Step 1: (tert-butyl (R)-3-(((6-bromoquinazolin-2-yl)amino)methyl)morpholine-4-carboxylate)

To a stirred solution of Int A (1.4 g, 5.75 mmol) in DMSO (14 mL) was added Int D (1.5 g, 6.93 mmol) and DIPEA (3.0 g, 4.04 mL, 23.21 mmol) at RT. The resulting mixture was heated at 80° C. for 18 h. The reaction mixture was poured into ice-cold water and extracted with ethyl acetate (3×50 mL). The organic layer was then washed with brine (50 mL) as well as water (50 mL), separated off, dried over anhydrous sodium sulphate and concentrated in vacuo to afford crude product. The crude product was purified by flash column chromatography on silica gel, eluting with 25% ethyl acetate in hexane to afford the title product (1.58 g, 65%).

Step 2: (tert-butyl (R)-3-((benzyl(6-bromoquinazolin-2-yl)amino)methyl)morpholine-4-carboxylate)

To a suspension of sodium hydride (0.74 g, 18.5 mmol) in dry DMF (22 mL) was added a solution of (tert-butyl (R)-3-(((6-bromoquinazolin-2-yl)amino)methyl)morpholine-4-carboxylate) (1.58 g, 3.73 mmol) in DMF (22 mL) at 00° C. under nitrogen. The reaction mixture was stirred for 30 min at 00° C. and then brought to RT before benzyl bromide (1.92 g, 11.23 mmol) was added. The reaction mixture was stirred at 00° C. for 30 min. The reaction mixture was poured into ice-water and extracted with ethyl acetate (3×50 mL). The organic layers were separated, combined and then washed with brine (50 mL) followed by water (50 mL), dried over sodium sulphate and concentrated in vacuo. The crude residue was purified by flash column chromatography on silica gel, eluting with 10% ethyl acetate in hexane to afford the title product (1.8 g, 94%).

Step 3: (tert-butyl (R)-3-((benzyl(6-(4,4,5,5-tetramethyl-1,3,2-dioxaborolan-2-yl)quinazolin-2-yl)amino)methyl) morpholine-4-carboxylate)

(Tert-butyl (R)-3-((benzyl(6-bromoquinazolin-2-yl)amino)methyl)morpholine-4-carboxylate) (1.8 g, 3.51 mmol) was subjected to the same conditions as described for example 1, step 2 to afford title product. Yield: 2.3 g (>100%).

Step 4: (tert-butyl (3R)-3-((benzyl(6-(1-(tetrahydro-2H-pyran-2-yl)-1H-pyrazolo[3,4-d]pyrimidin-4-yl)quinazolin-2-yl)amino)methyl) morpholine-4-carboxylate)

(Tert-butyl (R)-3-((benzyl(6-(4,4,5,5-tetramethyl-1,3,2-dioxaborolan-2-yl)quinazolin-2-yl)amino)methyl)morpholine-4-carboxylate) (2.30 g, 4.10 mmol) was subjected to the same conditions as described for example 1, step 3 to afford title product (1.2 g, 46%).

Step 5: ((R)—N-benzyl-N-(morpholin-3-ylmethyl)-6-(1H-pyrazolo[3,4-d]pyrimidin-4-yl)quinazolin-2-amine)

(Tert-butyl (3R)-3-((benzyl(6-(1-(tetrahydro-2H-pyran-2-yl)-1H-pyrazolo[3,4-d]pyrimidin-4-yl)quinazolin-2-yl)amino)methyl)morpholine-4-carboxylate) (1.2 g, 1.88 mmol) was subjected to the same conditions as described for example 1, step 4 and purified as follows: after completion of the reaction, the reaction mixture was filtered in vacuo and the resulting filtered solid was washed with ethyl acetate (3×50 mL) and hexane (3×50 mL). The solid was further triturated in acetone, then filtered in vacuo to afford the title product as a monohydrochloride salt (0.48 g, 52%).

Example 18

Benzyl-(S)-1-morpholin-3-ylmethyl-[6-(1H-pyrazolo[3,4-d]pyrimidin-4-yl)-quinazolin-2-yl]-amine The title compound was prepared from Int A (1.3 g, 5.34 mmol) via Synthetic Scheme C above using the same method as for Example 17 with the following exceptions: (a) in step 1, intermediate E, (S)-3-Aminomethyl-morpholine-4-carboxylic acid tert-butyl ester (prepared by an analogous procedure to intermediate D) was used instead of (R)-3-Aminomethyl-morpholine-4-carboxylic acid tert-butyl ester (b) in step 5 the acetone trituration was omitted. The compound is isolated as the monohydrochloride salt. Yield of final step: 0.63 g (67%).

Example 19

[(R)-1-(3,4-Difluoro-phenyl)-ethyl]-[6-(1H-pyrazolo[3,4-d]pyrimidin-4-yl)-quinazolin-2-yl]-amine Step 1: ((R)-6-bromo-N-(1-(3,4-difluorophenyl)ethyl)quinazolin-2-amine)

To a stirred solution of Intermediate A (0.5 g, 2.05 mol) in DMSO (5 mL) was added (R)-1-(3,4-difluorophenyl)ethylamine (0.39 g, 2.48 mmol) and DIPEA (1.08 g, 1.46 mL, 8.4 mmol) at room temperature. The resulting mixture was heated at 80° C. for 12 h. The reaction mixture was poured into ice water resulting in a precipitate. The solid was filtered off in vacuo and washed with cold water to afford the title product (0.7 g, 94%).

Step 2: ((R)—N-(1-(3,4-difluorophenyl)ethyl)-6-(4,4,5,5-tetramethyl-1,3,2-dioxaborolan-2-yl)quinazolin-2-amine)

To a stirred solution of ((R)-6-bromo-N-(1-(3,4-difluorophenyl)ethyl)quinazolin-2-amine) (0.70 g, 1.92 mmol) in 1,4-dioxane (8 mL) was added bis(pinacolato)diborane (0.84 g, 3.31 mmol) followed by potassium acetate (0.57 g, 5.80 mmol) under nitrogen at RT. The resulting mixture was purged by bubbling nitrogen through for 30 minutes. To the reaction mixture was added 1, 1-bis(diphenylphosphino)ferrocene palladium(II)dichloride dichloromethane complex (0.08 g, 0.098 mmol). The reaction mixture was then heated at 80° C. for 2 h. The reaction mixture was poured into water and extracted with ethyl acetate (2×40 mL). The combined organic layers were washed with brine (20 mL) then water (20 mL), separated off and dried over anhydrous sodium sulphate prior to concentration in vacuo. The crude residue was purified by flash column chromatography on silica gel, eluting with 7% ethyl acetate in hexane to afford the title product (0.94 g.>100%).

Step 3: (N—((R)-1-(3,4-difluorophenyl)ethyl)-6-(1-(tetrahydro-2H-pyran-2-yl)-1H-pyrazolo[3,4-d]pyrimidin-4-yl)quinazolin-2-amine)

To a stirred solution of ((R)—N-(1-(3,4-difluorophenyl)ethyl)-6-(4,4,5,5-tetramethyl-1,3,2-dioxaborolan-2-yl)quinazolin-2-amine) (0.94 g, 2.29 mmol) in a mixture of THF: water (12.5 mL, 4:1) was added Intermediate B (0.65 g, 2.72 mmol) followed by $Cs_2C03$ (2.97 g, 9.12 mmol) under nitrogen at RT. The mixture was purged by bubbling nitrogen gas through for 45 min, and to the resulting mixture was added Tetrakis(triphenylphosphine)palladium(0) (0.26 g, 0.225 mmol) at RT. The reaction mixture was then heated at 80° C. for 3 h. The resulting reaction mixture was poured into water and the product was extracted using ethyl acetate (2×30 mL). The combined organic layers were washed with brine (20 mL) then water (20 mL), separated off and dried over anhydrous sodium sulphate, then concentrated in vacuo to afford crude product. The crude was purified by flash column chromatography on silica gel, eluting with 45% ethyl acetate in hexane to afford title product (0.6 g, 54%).

Step 4: ((R)—N-(1-(3,4-difluorophenyl)ethyl)-6-(1H-pyrazolo[3,4-d]pyrimidin-4-yl)quinazolin-2-amine)

To a stirred solution of (N—((R)-1-(3,4-difluorophenyl)ethyl)-6-(1-(tetrahydro-2H-pyran-2-yl)-1H-pyrazolo[3,4-d]pyrimidin-4-yl)quinazolin-2-amine) (0.6 g, 1.23 mmol) in a mixture of methanol (1.4 mL) and 1,4-dioxane (6 mL) was added 4N HCl in 1,4-dioxane (6 mL) under nitrogen at RT. The reaction mixture was further stirred for 1 h at RT, at which point a precipitate had formed which was filtered off in vacuo and washed with ethyl acetate (3×30 mL) followed by hexane (3×30 mL). The solid was then added to water (10 mL) and the resulting mixture was basified up to pH 8 using saturated $NaHCO_3$ solution, with stirring for 30 min. The reaction mixture was filtered in vacuo, washing with water, to afford the title product (0.27 g, 54%).

Example 20

((R)-1-Phenyl-ethyl)-[6-(9H-purin-6-yl)-quinazolin-2-yl]-amine

The title product was prepared from intermediate A (10 g, 41.1 mmol) using the same method as described for Example 19 with the following exceptions: (a) in step 1, (R)-1-phenyl-ethylamine was used instead of (R)-1-(3,4-difluorophenyl)ethylamine (b) in step 3, intermediate F, 6-chloro-9-(tetrahydro-pyran-2-yl)-9H-purine, was used instead of intermediate B. Yield of final step: 0.26 g (46%).

Example 21

Benzyl-[6-(1H-pyrazolo[3,4-d]pyrimidin-4-yl)-quinazolin-2-yl]-amine

The title product was prepared from intermediate A (0.5 g, 2.05 mmol) using the same method as described for Example 19 except that in step 1, benzylamine was used instead of (R)-1-(3,4-difluorophenyl)ethylamine. Yield of final step: 0.2 g (40%).

Example 22

[6-(3-Methyl-1H-pyrazolo[3,4-d]pyrimidin-4-yl)-quinazolin-2-yl]-((R)-1-phenyl-ethyl)-amine The title product was prepared from intermediate A (10 g, 41.1 mmol) using the same method as described for Example 19 with the following exceptions: (a) in step 1, (R)-1-phenyl-ethylamine was used instead of (R)-1-(3,4-difluorophenyl)ethylamine (b) in step 3, intermediate G, 4-chloro-3-methyl-1-(tetrahydro-pyran-2-yl)-1H-pyrazolo[3,4-d]pyrimidine, was used instead of intermediate B (c) in step 4, preparative HPLC (using preparative HPLC method 3) was used as final step to purify title product. Yield of final step: 0.12 g (24%).

Example 23

(3-Methoxy-benzyl)-[6-(1H-pyrazolo[3,4-d]pyrimidin-4-yl)-quinazolin-2-yl]-amine

The title product was prepared from intermediate A (0.5 g, 2.05 mmol) using the same method as described for Example 19 except that in step 1, 3-methoxy benzylamine was used instead of (R)-1-(3,4-difluorophenyl)ethylamine. Yield of final step: 0.27 g (59%).

Example 24

2-Fluoro-benzyl)-[6-(1H-pyrazolo[3,4-d]pyrimidin-4-yl)-quinazolin-2-yl]-amine

The title product was prepared from intermediate A (0.4 g, 1.64 mmol) using the same method as described for Example 19 except that in step 1, 2-fluorobenzylamine was used instead of (R)-1-(3,4-difluorophenyl)ethylamine. Yield of final step: 0.17 g (46%).

Example 25

(3,4-Difluoro-benzyl)-[6-(1H-pyrazolo[3,4-d]pyrimidin-4-yl)-quinazolin-2-yl]-amine The title product was prepared from intermediate A (0.5 g, 2.05 mmol) using the same method as described for Example 19 except that in step 1, 3,4-difluorobenzylamine was used instead of (R)-1-(3,4-difluorophenyl)ethylamine. Yield of final step: 0.34 g (78%).

Example 26

N-(3-{[6-(1H-Pyrazolo[3,4-d]pyrimidin-4-yl)-quinazolin-2-ylamino]-methyl}-phenyl)-methanesulfonamide Intermediate H (0.6 g, 1.47 mmol) was subjected to the conditions of steps 2-4 of Example 19 followed by purification by preparative HPLC method 4 to afford the title product (0.05 g, 11%).

Example 27

[(R)-1-(3-Methoxy-phenyl)-ethyl]-[6-(1H-pyrazolo[3,4-d]pyrimidin-4-yl)-quinazolin-2-yl]-amine The title product was prepared from intermediate A (0.6 g, 2.46 mmol) using the same method as described for Example 19 except that in step 1, (R)-(+)-1-(3-methoxyphenyl)ethylamine was used instead of (R)-1-(3,4-difluorophenyl)ethylamine.

Yield of final step: 0.4 g (59%).

Example 28

[(R)-1-(2-Fluoro-phenyl)-ethyl]-[6-(1H-pyrazolo[3,4-d]pyrimidin-4-yl)-quinazolin-2-yl]-amine The title product was prepared from intermediate A (0.5 g, 2.05 mmol) using the same method as described for Example 19 with the following exceptions: (a) in step 1, (R)-1-(2-fluorophenyl)ethylamine was used instead of (R)-1-(3,4-difluorophenyl)ethylamine (b) in step 4, a final acetone trituration was applied. Yield of final step: 0.3 g (42%).

Example 29

((S)-1-Phenyl-ethyl)-[6-(1H-pyrazolo[3,4-d]pyrimidin-4-yl)-quinazolin-2-yl]-amine The title product was prepared from intermediate A (2.5 g, 10.3 mmol) using the same method as described for Example 19 with the following exceptions: (a) (S)-(−)-α-methyl benzyl amine was used instead of (R)-1-(3,4-difluorophenyl)ethylamine in step 1 (b) in step 4, a final ethyl acetate trituration was applied. Yield of final step: 0.56 g (47%).

Example 30

N-(3-{(R)-1-[6-(1H-Pyrazolo[3,4-d]pyrimidin-4-yl)-quinazolin-2-ylamino]-ethyl}-phenyl)-methanesulfonamide Intermediate I (1.0 g, 1.47 mmol) was subjected to the conditions of steps 2-4 of Example 19 to afford the title product. Yield of final step: 0.22 g (39%).

Example 31

(R)-3-Phenyl-3-[6-(1H-pyrazolo[3,4-d]pyrimidin-4-yl)-quinazolin-2-ylamino]-propan-1-ol The title product was prepared from intermediate A (0.5 g, 2.05 mmol) using the same method as described for Example 19 with the exception that in step 1, (R)-3-Amino-3-phenyl-propan-1-ol was used instead of (R)-1-(3,4-difluorophenyl)ethylamine. Yield of final step: 0.14 g (38%).

Example 32

[(R)-1-(2,4-Difluoro-phenyl)-ethyl]-[6-(1H-pyrazolo[3,4-d]pyrimidin-4-yl)-quinazolin-2-yl]-amine The title product was prepared from intermediate A (0.5 g, 2.05 mmol) using the same method as described for Example 19 with the exception that (R)-1-(2,4-Difluorophenyl)-ethylamine hydrochloride was used in step 1 instead of (R)-1-(3,4-difluorophenyl)ethylamine. Yield of final step: 0.205 g (56%).

Example 33

[(R)-1-(2,6-Difluoro-phenyl)-ethyl]-[6-(1H-pyrazolo[3,4-d]pyrimidin-4-yl)-quinazolin-2-yl]-amine The title product was prepared from intermediate A (0.5 g, 2.05 mmol) using the same method as described for Example 19 with the exception that (R)-1-(2,6-difluorophenyl)ethanamine hydrochloride was used in step 1 instead of (R)-1-(3,4-difluorophenyl)ethylamine. Yield of final step: 0.235 g (47%).

Example 34

4-[2-((R)-1-Phenyl-ethylamino)-quinazolin-6-yl]-7H-pyrrolo[2,3-d]pyrimidine-5-carbonitrile The title product was prepared from intermediate A (1.0 g, 4.11 mmol) using the same method as described for Example 19 with the following exceptions: (a) (R)-1-phenyl-ethylamine was used in step 1 instead of (R)-1-(3,4-difluorophenyl)ethylamine; (b) step 3 was carried out as described below; and (c) Step 4 was omitted. 4-Chloro-7H-pyrrolo[2,3-d]pyrimidine-5-carbonitrile is commercially available. Yield of final step: 0.142 g (19%).

Step 3: 4-[2-((R)-1-Phenyl-ethylamino)-quinazolin-6-yl]-7H-pyrrolo[2,3-d]pyrimidine-5-carbonitrile To a stirred solution of 4-chloro-7H-pyrrolo[2,3-d]pyrimidine-5-carbonitrile (0.35 g, 1.96 mmol) and ((R)-1-

Phenyl-ethyl)-[6-(4,4,5,5-tetramethyl-[1,3,2]dioxaborolan-2-yl)-quinazolin-2-yl]-amine (0.75 g, 2.00 mmol) in DMF (7 mL) was added 1M aqueous $NaHCO_3$ solution (5.9 mL, 5.9 mmol) under a nitrogen atmosphere at RT. The reaction mixture was purged with nitrogen gas for 30 minutes and then to the reaction mixture was added dichlorobis(triphenylphosphine)palladium(II) (0.07 g, 0.0997 mmol) at RT. The resulting reaction mixture was then heated at 80° C. for 18 h. The reaction mixture was poured into water and extracted with ethyl acetate (2×20 mL). The organic layers were combined and washed with brine (20 mL), then separated off, dried over anhydrous sodium sulphate and concentrated in vacuo to afford crude title product. The crude was purified by flash column chromatography on silica gel, eluting with 60% ethyl acetate in hexane to afford title product which was then further purified by preparative HPLC using method 5.

Example 35

2-{(R)-1-[6-(1H-Pyrazolo[3,4-d]pyrimidin-4-yl)-quinazolin-2-ylamino]-ethyl}-phenol The title product was prepared from intermediate A (0.8 g, 3.29 mmol) using the same method as described for Example 19 with the following exceptions: (1) 2-((R)-1-Amino-ethyl)-phenol was used in step 1 instead of (R)-1-(3,4-difluorophenyl)ethylamine; and (2) In step 4 the reaction mixture was not filtered immediately but was first basified up to pH 8 using aqueous saturated $NaHCO_3$ solution. The aqueous phase was extracted with EtOAc (2×20 mL). The organic layers were combined and concentrated in vacuo to afford crude title product which was purified by flash column chromatography on silica gel, eluting with 4% methanol in chloroform to afford title product which was then further purified by preparative HPLC using method 6. Yield of final step: 0.032 g (12%).

Example 36

3-{(R)-1-[6-(1H-Pyrazolo[3,4-d]pyrimidin-4-yl)-quinazolin-2-ylamino]-ethyl}-phenol The title product was prepared from intermediate A (0.8 g, 3.29 mmol) using the same method as described for Example 19 with the exception that 3-((R)-1-amino-ethyl)-phenol was used in step 1 instead of (R)-1-(3,4-difluorophenyl)ethylamine. Yield of final step: 0.126 g (16%).

Example 37

4-{(R)-1-[6-(1H-Pyrazolo[3,4-d]pyrimidin-4-yl)-quinazolin-2-ylamino]-ethyl}-phenol The title product was prepared from intermediate A (0.8 g, 3.29 mmol) using the same method as described for Example 19 with the following exceptions: (1) 4-((R)-1-Amino-ethyl)-phenol was used in step 1 instead of (R)-1-(3,4-difluorophenyl)ethylamine (2) In step 4 the reaction mixture was not filtered immediately but was first basified up to pH 8 using aqueous saturated $NaHCO_3$ solution, and was then filtered in vacuo. The isolated solid was then purified by preparative HPLC using method 6 to afford title product. Yield of final step: 0.1 g (20%).

Example 38

(S)-2-(2-Fluoro-phenyl)-2-[6-(1H-pyrazolo[3,4-d]pyrimidin-4-yl)-quinazolin-2-ylamino]-ethanol The title product was prepared from intermediate A (0.6 g, 2.46 mmol) using the same method as described for Example 19 with the exception that (S)-2-Amino-2-(2-fluoro-phenyl)-ethanol was used in step 1 instead of (R)-1-(3,4-difluorophenyl)ethylamine.

Example 39

(S)-2-(3-Fluoro-phenyl)-2-[6-(1H-pyrazolo[3,4-d]pyrimidin-4-yl)-quinazolin-2-ylamino]-ethanol The title product was prepared from intermediate A (0.8 g, 3.29 mmol) using the same method as described for Example 19 with the exception that (S)-2-amino-2-(3-fluoro-phenyl)-ethanol was used in step 1 instead of (R)-1-(3,4-difluorophenyl)ethylamine.

Example 40

(S)-2-(4-Fluoro-phenyl)-2-[6-(1H-pyrazolo[3,4-d]pyrimidin-4-yl)-quinazolin-2-ylamino]-ethanol The title product was prepared from intermediate A (0.8 g, 3.29 mmol) using the same method as described for Example 19 with the exception that (S)-2-amino-2-(4-fluoro-phenyl)-ethanol was used in step 1 instead of (R)-1-(3,4-difluorophenyl)ethylamine.

Example 41

(R)-3-(2-Fluoro-phenyl)-3-[6-(1H-pyrazolo[3,4-d]pyrimidin-4-yl)-quinazolin-2-ylamino]-propan-1-ol The title product was prepared from intermediate A (0.8 g, 3.29 mmol) using the same method as described for Example 19 with the exception that (R)-3-amino-3-(2-fluoro-phenyl)-propan-1-ol was used in step 1 instead of (R)-1-(3,4-difluorophenyl)ethylamine. Yield of final step: 0.144 g (34%).

Example 42

(R)-3-(3-Fluoro-phenyl)-3-[6-(1H-pyrazolo[3,4-d]pyrimidin-4-yl)-quinazolin-2-ylamino]-propan-1-ol The title product was prepared from intermediate A (0.8 g, 3.29 mmol) using the same method as described for Example 19 with the exception that (R)-3-amino-3-(3-fluoro-phenyl)-propan-1-ol was used in step 1 instead of (R)-1-(3,4-difluorophenyl)ethylamine. Yield of final step: 0.1 g (24%).

Example 43

(R)-3-(4-Fluoro-phenyl)-3-[6-(1H-pyrazolo[3,4-d]pyrimidin-4-yl)-quinazolin-2-ylamino]-propan-1-ol The title product was prepared from intermediate A (0.6 g, 2.46 mmol) using the same method as described for Example 19 with the following exceptions: (1) (R)-3-amino-3-(4-fluoro-phenyl)-propan-1-ol was used in step 1 instead of (R)-1-(3,4-difluorophenyl)ethylamine; and (2) in step 4 the reaction mixture was concentrated in vacuo, added into water and the resulting reaction mixture was basified up to pH 8 using aqueous saturated $NaHCO_3$ solution. The mixture was stirred for 30 min at RT and was then filtered in vacuo washing with water (3×30 mL) followed by hexane (2×15 mL). The crude material was purified by preparative HPLC using method 7. Yield of final step: 0.203 g (31%).

| Example No. | Name | Synthetic scheme | $^1$H NMR | Chiral HPLC RT (min) | LC RT (min) | MS | Chiral HPLC method | LCMS method |
|---|---|---|---|---|---|---|---|---|
| 1 | ((R)-1-Phenyl-ethyl)-[6-(1H-pyrazolo[3,4-d]pyrimidin-4-yl)-quinazolin-2-yl]-amine | A | 1H NMR (DMSO-d6) δ 14.39-14.10 (br s, 1H), 9.44 (1H, s), 9.04 (s, 1H), 8.90 (s, 2H), 8.74-8.55 (m, 2H), 7.68 (d, 1H), 7.49 (m, 2H), 7.32 (t, 2H), 7.22 (t, 1H), 5.46-5.33 (m, 1H), 1.52 (3H, d). | 34.981 | 6.148 | 368.3 (MH+) | 2 | 3 |
| 2 | ((R)-1-(3-Chloro-phenyl)-ethyl)-[6-(1H-pyrazolo[3,4-d]pyrimidin-4-yl)-quinazolin-2-yl]-amine monohydrochloride | A | 1H NMR (DMSO-d6) δ 14.29 (br s, 1H), 9.48 (br s, 1H), 9.06 (s, 1H), 8.94 (br s, 1H), 8.85 (br s, 1H), 8.70 (m, 1H), 7.73 (d, 1H), 7.58 (s, 1H), 7.47 (s, 1H), 7.38 (t, 1H), 7.29 (d, 1H), 5.44 (br m, 1H) 1.54 (d, 3H). | 6.29 | 2.289 | 402.3 (MH+) | 1 | 2 |
| 3 | ((R)-1-(3-Fluoro-phenyl)-ethyl)-[6-(1H-pyrazolo[3,4-d]pyrimidin-4-yl)-quinazolin-2-yl]-amine monohydrochloride | A | 1H NMR (DMSO-d6) δ 14.37 (br s, 1H), 9.50 (br s, 1H), 9.06 (s, 1H), 8.99-8.84 (m, 3H), 8.69 (br m, 1H), 7.74 (d, 1H), 7.41-7.29 (m, 3H), 7.04 (m, 1H), 5.47 (m, 1H), 1.55 (d, 3H). | 5.82 | 2.176 | 386.3 (MH+) | 1 | 2 |
| 4 | ((R)-1-(4-Fluoro-phenyl)-ethyl)-[6-(1H-pyrazolo[3,4-d]pyrimidin-4-yl)-quinazolin-2-yl]-amine | A | 1H NMR (DMSO-d6) δ 14.21 (br s, 1H), 9.39 (s, 1H), 9.03 (s, 1H), 8.89 (s, 1H), 8.85 (d, 1H), 8.63 (d, 1H), 8.36 (d, 1H), 7.57 (d, 1H), 7.55-7.45 (br m, 2H), 7.14 (t, 2H), 5.32 (br m, 1H), 1.51 (d, 3H). | 5.75 | 2.150 | 386.2 (MH+) | 1 | 2 |
| 5 | ((S)-2-Hydroxy-1-phenyl-ethyl)-[6-(1H-pyrazolo[3,4-d]pyrimidin-4-yl)-quinazolin-2-yl]-amine monohydrochloride | A | 1H NMR (DMSO-d6) δ 14.22 (s, 1H), 9.40 (s, 1H), 9.03 (s, 1H), 8.88 (d, 2H), 8.64 (br d, 1H), 8.23 (br s, 1H), 7.58 (br d, 1H), 7.47 (br m, 2H), 7.32 (t, 2H), 7.22 (t, 1H), 5.28 (br m, 1H), 3.70 (m, 2H). | 10.52 | 2.534 | 384.2 (MH+) | 1 | 2 |
| 6 | (4-Fluorobenzyl)-[6-(1H-pyrazolo[3,4-d]pyrimidin-4-yl)-quinazolin-2-yl]-methylamine monohydrochloride | A | 1H NMR (DMSO-d6) δ 14.30 (br s, 1H), 9.60 (s, 1H), 9.08 (s, 1H), 9.02 (d, 1H), 8.96 (s, 1H), 8.76 (br m, 1H), 7.96 (br m, 1H), 7.40 (br m, 2H), 7.19 (t, 2H) 5.09 (s, 2H), 3.30 (s, 3H). | N/A | 2.371 | 386.3 (MH+) | N/A | 2 |
| 7 | Benzyl-[6-(1H-pyrazolo[3,4-d]pyrimidin-4-yl)-quinazolin-2-yl]-methylamine monohydrochloride | A | 1H NMR (DMSO-d6) δ 14.35 (br s, 1H), 9.60 (s, 1H), 9.09 (s, 1H), 9.02 (s, 1H), 8.96 (s, 1H), 8.82-8.70 (br m, 1H), 7.95 (br m, 1H), 7.39-7.27 (m, 5H), 5.12 (s, 2H), 3.31 (s, 3H). | N/A | 2.373 | 368.3 (MH+) | N/A | 2 |
| 8 | ((R)-1-Phenyl-ethyl)-[6-(1H-pyrazolo[3,4-d]pyrimidin-4-yl)-quinazolin-2-yl]-methylamine monohydrochloride | B | 1H NMR (DMSO-d6) δ 14.13 (br s, 1H), 9.59 (s, 1H), 9.07 (s, 1H), 9.01 (s, 1H), 8.96 (s, 1H), 8.74 (d, 1H), 7.82 (br s, 1H), 7.37 (m, 4H), 7.32 (m, 1H), 6.48 | 7.33 | 2.492 | 382.3 (MH+) | 1 | 2 |

-continued

| Example No. | Name | Synthetic scheme | $^1$H NMR | Chiral HPLC RT (min) | LC RT (min) | MS | Chiral HPLC method | LCMS method |
|---|---|---|---|---|---|---|---|---|
| | | | (m, 1H), 3.01 (s, 3H), 1.64 (d, 3H). | | | | | |
| 9 | (4-Fluorobenzyl)-[6-(1H-pyrazolo[3,4-d]pyrimidin-4-yl)-quinazolin-2-yl]-amine | A | 1H NMR (DMSO-d6) δ 14.22 (s, 1H), 9.41 (s, 1H), 9.04 (s, 1H), 8.91 (d, 2H), 8.66 (dd, 1H), 8.37 (br s, 1H), 7.63 (d, 1H), 7.45 (br s, 2H), 7.16 (t, 2H), 4.64 (br d, 2H). | N/A | 6.057 | 372.17 (MH+) | N/A | 1 |
| 10 | (3-Fluorobenzyl)-[6-(1H-pyrazolo[3,4-d]pyrimidin-4-yl)-quinazolin-2-yl]-amine | A | 1H NMR (DMSO-d6) δ 14.23 (s, 1H), 9.43 (s, 1H), 9.04 (s, 1H), 8.90 (d, 2H), 8.65 (d, 1H), 8.40 (br s, 1H), 7.63 (d, 1H), 7.37 (q, 1H), 7.29-7.13 (m, 2H), 7.05 (t, 1H), 4.68 (d, 2H) | N/A | 6.118 | 372.14 (MH+) | N/A | 1 |
| 11 | (3-Chlorobenzyl)-[6-(1H-pyrazolo[3,4-d]pyrimidin-4-yl)-quinazolin-2-yl]-amine | A | 1H NMR (DMSO-d6) δ 9.45 (s, 1H), 9.04 (s, 1H), 8.89 (d, 2H), 8.65 (d, 1H), 8.35 (br s, 1H), 7.61 (d, 1H), 7.49-7.38 (m, 2H), 7.29 (m, 2H), 4.71 (d, 2H). | N/A | 6.162 | 388.1 (MH+) | N/A | 1 |
| 12 | ((R)-1-Phenyl-ethyl)-[7-(1H-pyrazolo[3,4-d]pyrimidin-4-yl)-quinazolin-2-yl]-amine | A | 1H NMR (DMSO-d6) δ 14.30 (br s, 1H), 9.26 (s, 1H), 9.11 (s, 1H), 8.70 (s, 1H), 8.23 (s, 1H), 8.17 (br s, 1H), 8.09-7.99 (m, 2H), 7.49 (br s, 2H), 7.31 (br m, 2H), 7.20 (d, 1H), 5.33 (m, 1H), 1.51 (d, 3H). | ND | 4.760 | 368.2 (MH+) | | 1 |
| 13 | ((R)-1-Phenyl-ethyl)-[6-(1H-pyrazolo[3,4-b]pyridin-4-yl)-quinazolin-2-yl]-amine monohydrochloride | A | 1H NMR (DMSO-d6) δ 13.90 (br s, 1H), 9.60-9.43 (br s, 1H), 8.63 (d, 1H), 8.55 (br s, 1H), 8.51 (s, 1H), 8.35 (br s, 1H), 7.95 (br s, 1H), 7.55 (br s, 2H), 7.48 (d, 1H), 7.36 (t, 2H), 7.26 (t, 1H), 5.60 (br s, 1H), 1.58 (d, 3H). | 7.53 | 2.191 | 367.30 (MH+) | 3 | 2 |
| 14 | ((R)-1-Phenyl-ethyl)-[6-(7H-pyrrolo[2,3-d]pyrimidin-4-yl)-quinazolin-2-yl]-amine monohydrochloride | A | 1H NMR (DMSO-d6) δ 13.10-12.81 (br s, 1H), 9.58-9.45 (br s, 1H), 9.01 (s, 1H), 8.75 (br s, 1H), 8.52 (br s, 1H), 7.92 (s, 1H), 7.79 (br s, 1H), 7.52 (br m, 2H) 7.33 (t, 2H), 7.23 (m, 2H), 5.47 (br s, 1H), 1.55 (d, 3H). | 5.81 | 2.110 | 367.3 (MH+) | 4 | 2 |
| 15 | ((R)-1-Phenyl-ethyl)-[6-(1H-pyrrolo[2,3-b]pyridin-4-yl)-quinazolin-2-yl]-amine monohydrochloride | A | 1H NMR (DMSO-d6) δ 9.46-9.42 (br s, 1H), 8.46 (d, 2H), 8.28 (br s, 1H), 7.95 (br s, 1H), 7.76 (t, 1H), 7.57-7.45 (m, 3H), 7.35 (t, 2H), 7.26 (t, 1H), 6.91 (br s, 1H), 5.59 (br s, 1H), 1.58 (d, 3H). | 7.64 | 2.225 | 366.3 (MH+) | 3 | 2 |
| 16 | N-Benzyl-N',N'-dimethyl-N-[6-(1H-pyrazolo[3,4-d]pyrimidin-4-yl)-quinazolin-2-yl]-ethane-1,2-diamine monohydrochloride | A | 1H NMR (DMSO-d6) δ 10.44 (br s, 1H), 9.58 (s, 1H), 9.09 (s, 1H), 9.00 (s, 1H), 8.95 (s, 1H), 8.73 (d, 1H), 7.78 (br m, 1H), 7.45-7.27 (m, 5H), 5.10 (s, 2H), | N/A | 4.318 | 425.3 (MH+) | N/A | 4 |

-continued

| Example No. | Name | Synthetic scheme | $^1$H NMR | Chiral HPLC RT (min) | LC RT (min) | MS | Chiral HPLC method | LCMS method |
|---|---|---|---|---|---|---|---|---|
| | | | 4.08 (m, 2H), 3.40 (m, 2H), 2.88 (s, 6H). | | | | | |
| 17 | Benzyl-(R)-1-morpholin-3-ylmethyl-[6-(1H-pyrazolo[3,4-d]pyrimidin-4-yl)-quinazolin-2-yl]-amine monohydrochloride | C | 1H NMR (DMSO-d6) δ 14.27 (br s, 1H), 9.94 (br m, 1H), 9.59 (br s, 2H), 9.07 (s, 1H), 9.00 (br s, 1H), 8.95 (s, 1H), 8.72 (d, 1H), 7.81 (br d, 1H), 7.41-7.23 (m, 5H), 5.25 (m, 1H), 5.01 (d, 1H), 4.04-3.65 (m, 7H), 3.30 (br m, 1H), 3.11-2.99 (m, 1H). | 16.272 | 5.285 | 453.3 (MH+) | 5 | 1 |
| 18 | Benzyl-(S)-1-morpholin-3-ylmethyl-[6-(1H-pyrazolo[3,4-d]pyrimidin-4-yl)-quinazolin-2-yl]-amine monohydrochloride | C | 1H NMR (DMSO-d6) δ 14.36 (br s, 1H), 9.89 (br m, 1H), 9.59 (br s, 2H), 9.07 (s, 1H), 9.00 (br s, 1H), 8.98 (s, 1H), 8.72 (d, 1H), 7.81 (br d, 1H), 7.42-7.25 (m, 5H), 5.25 (m, 1H), 5.01 (d, 1H), 4.04-3.65 (m, 7H), 3.30 (br m, 1H), 3.11-2.99 (m, 1H). | 13.719 | 5.246 | 453.4 (MH+) | 5 | 1 |
| 19 | [(R)-1-(3,4-Difluoro-phenyl)-ethyl]-[6-(1H-pyrazolo[3,4-d]pyrimidin-4-yl)-quinazolin-2-yl]-amine | A | 1H NMR (DMSO-d6) δ 14.30 (br s, 1H), 9.48 (s, 1H), 9.05 (s, 1H), 8.91 (s, 2H), 8.82 (br s, 1H), 8.70 (m, 1H), 7.76 (m, 1H), 7.55 (m, 1H), 7.43-7.31 (m, 2H), 5.43 (br m, 1H), 1.53 (d, 3H). | 27.631 | 6.195 | 404.3 (MH+) | 6 | 1 |
| 20 | ((R)-1-Phenyl-ethyl)-[6-(9H-purin-6-yl)-quinazolin-2-yl]-amine | A | 1H NMR (DMSO-d6) δ 13.69 (br s, 1H), 9.39-9.30 (m, 2H), 9.13 (br d, 1H), 8.95 (s, 1H), 8.68 (s, 1H), 8.37 (br s, 1H), 7.65-7.54 (m, 1H), 7.49-7.44 (m, 2H), 7.34-7.30 (t, 2H), 7.21 (t, 1H), 5.34 (m, 1H), 1.51 (d, 3H). | 7.958 | 4.824 | 368.2 (MH+) | 2 | 1 |
| 21 | Benzyl-[6-(1H-pyrazolo[3,4-d]pyrimidin-4-yl)-quinazolin-2-yl]-amine | A | 1H NMR (DMSO-d6) δ 14.24 (br s, 1H), 9.43 (s, 1H), 9.04 (s, 1H), 8.91 (s, 2H), 8.66 (d, 1H), 8.50 (br s, 1H), 7.65 (d, 1H), 7.41-7.30 (m, 4H), 7.23 (t, 1H), 4.70 (s, 2H). | N/A | 5.221 | 354.2 (MH+) | N/A | 1 |
| 22 | [6-(3-Methyl-1H-pyrazolo[3,4-d]pyrimidin-4-yl)-quinazolin-2-yl]-((R)-1-phenyl-ethyl)-amine | A | 1H NMR (DMSO-d6) δ 13.82 (s, 1H), 9.31 (s, 1H), 8.96 (s, 1H), 8.32-8.25 (m, 2H), 8.13 (br d, 1H), 7.56 (d, 1H), 7.51-7.43 (m, 2H), 7.33 (t, 2H), 7.20 (t, 1H), 5.34 (m, 1H), 2.42 (s, 3H), 1.51 (d, 3H). | 23.211 | 6.055 | 382.5 (MH+) | 6 | 1 |
| 23 | (3-Methoxy-benzyl)-[6-(1H-pyrazolo[3,4-d]pyrimidin-4-yl)-quinazolin-2-yl]-amine | A | 1H NMR (DMSO-d6) δ 14.23 (br s, 1H), 9.44 (s, 1H), 9.04 (s, 1H), 8.92 (s, 2H), 8.69 (br d, 1H), 8.60 (br s, 1H), 7.69 (d, 1H), 7.23 (t, 1H), 7.02-6.93 (m, 2H), 6.80 (dd, 1H), 4.68 (m, 2H), 3.73 (s, 3H). | N/A | 5.161 | 384.0 (MH+) | N/A | 1 |
| 24 | (2-Fluoro-benzyl)-[6-(1H-pyrazolo[3,4-d]pyrimidin-4-yl)-quinazolin-2-yl]-amine | A | 1H NMR (DMSO-d6) δ 14.21 (s, 1H), 9.43 (s, 1H), 9.03 (s, 1H), 8.90 (d, 2H), 8.66 (d, 1H), 8.37-8.25 (br s, 1H), | N/A | 5.260 | 372.1 (MH+) | N/A | 1 |

-continued

| Example No. | Name | Synthetic scheme | $^1$H NMR | Chiral HPLC RT (min) | LC RT (min) | MS | Chiral HPLC method | LCMS method |
|---|---|---|---|---|---|---|---|---|
| | | | 7.63 (d, 1H), 7.45 (br s, 1H), 7.30 (m, 1H), 7.22-7.13 (m, 2H), 4.72 (m, 2H). | | | | | |
| 25 | (3,4-Difluoro-benzyl)-[6-(1H-pyrazolo[3,4-d]pyrimidin-4-yl)-quinazolin-2-yl]-amine | A | 1H NMR (DMSO-d6) δ 14.50-14.12 (br s, 1H), 9.47 (s, 1H), 9.05 (s, 1H,), 9.00-8.90 (m, 2H), 8.89-8.61 (m, 2H), 7.74 (d, 1H), 7.51-7.36 (m, 2H), 7.28 (m, 1H), 4.70 (s, 2H). | N/A | 5.277 | 390.0 (MH+) | N/A | 1 |
| 26 | N-(3-{[6-(1H-Pyrazolo[3,4-d]pyrimidin-4-yl)-quinazolin-2-ylamino]-methyl}-phenyl)-methanesulfonamide | A | 1H NMR (DMSO-d6) δ 9.41 (s, 1H), 9.03 (s, 1H), 8.92 (s, 1H), 8.89 (s, 1H), 8.66 (d, 1H), 8.39-8.29 (br s, 1H), 7.62 (d, 1H), 7.31-7.24 (m, 2H), 7.15-7.03 (m, 2H), 4.63 (m, 2H), 2.94 (s, 3H). | N/A | 5.256 | 447.2 (MH+) | N/A | 1 |
| 27 | [(R)-1-(3-Methoxy-phenyl)-ethyl]-[6-(1H-pyrazolo[3,4-d]pyrimidin-4-yl)-quinazolin-2-yl]-amine | A | 1H NMR (DMSO-d6) δ 9.60-9.43 (br s, 1H), 9.05 (s, 1H), 8.98-8.90 (m, 2H), 8.79-8.65 (m, 2H), 7.80-7.69 (br s, 1H), 7.26 (t, 1H), 7.14-7.00 (m, 2H), 6.80 (dd, 1H), 5.41 (m, 1H), 3.74 (s, 3H), 1.53 (d, 3H). | 36.866 | 5.278 | 398.3 (MH+) | 7 | 1 |
| 28 | [(R)-1-(2-Fluoro-phenyl)-ethyl]-[6-(1H-pyrazolo[3,4-d]pyrimidin-4-yl)-quinazolin-2-yl]-amine | A | 1H NMR (DMSO-d6) δ 14.50-13.95 (br s, 1H), 9.60-9.46 (m, 1H), 9.05 (s, 1H), 8.95-8.89 (m, 2H), 8.90-8.72 (br s, 1H,), 8.66 (m, 1H), 7.81-7.64 (m, 1H), 7.56 (t, 1H), 7.30 (m, 1H), 7.19 (q, 2H), 5.64 (br s, 1H), 1.55 (d, 3H). | 16.652 | 6.180 | 386.3 (MH+) | 5 | 1 |
| 29 | ((S)-1-Phenyl-ethyl)-[6-(1H-pyrazolo[3,4d]pyrimidin-4-yl)-quinazolin-2-yl]-amine | A | 1H NMR (DMSO-d6) δ 14.28-14.05 (br s, 1H), 9.44 (s, 1H), 9.04 (s, 1H), 8.91 (s, 1H), 8.90 (s, 1H), 8.71-8.60 (br m, 2H), 7.66 (d, 1H), 7.49 (m, 2H), 7.33 (t, 2H), 7.22 (t, 1H), 5.39 (br m, 1H), 1.52 (d, 3H). | 59.026 | 5.379 | 368.3 (MH+) | 2 | 1 |
| 30 | N-(3-{(R)-1-[6-(1H-Pyrazolo[3,4-d]pyrimidin-4-yl)-quinazolin-2-ylamino]-ethyl}-phenyl)-methanesulfonamide | A | 1H NMR (DMSO-d6) δ 14.24 (br s, 1H), 9.72 (d, 1H), 9.42 (s, 1H), 9.03 (s, 1H), 8.90 (d, 1H), 8.89 (s, 1H), 8.65 (br m, 1H), 8.52 (broad s, 1H), 7.62 (br d, 1H), 7.36-7.19 (m, 3H), 7.05 (dd, 1H), 5.30 (br m, 1H), 2.97 (s, 3H), 1.53 (d, 3H). | 5.295 | 5.433 | 461.3 (MH+) | 8 | 1 |
| 31 | (R)-3-Phenyl-3-[6-(1H-pyrazolo[3,4-d]pyrimidin-4-yl)-quinazolin-2-ylamino]-propan-1-ol | A | 1H NMR (DMSO-d6) δ 14.41-14.05 (br s, 1H), 9.51-9.42 (m, 1H), 9.04 (s, 1H), 8.901 (s, 2H), 8.80-8.68 (m, 2H), 7.66 (br d, 1H), 7.49 (d, 2H), 7.33 (t, 2H), 7.21 (t, 1H), 5.51-5.32 (m, 1H), 3.49 (m, 2H), 2.15-1.90 (m, 2H). | 10.657 | 5.618 | 398.4 (MH+) | 9 | 1 |

-continued

| Example No. | Name | Synthetic scheme | $^1$H NMR | Chiral HPLC RT (min) | LC RT (min) | MS | Chiral HPLC method | LCMS method |
|---|---|---|---|---|---|---|---|---|
| 32 | [(R)-1-(2,4-Difluoro-phenyl)-ethyl]-[6-(1H-pyrazolo[3,4-d]pyrimidin-4-yl)-quinazolin-2-yl]-amine | A | 1H NMR (DMSO-d6) δ 14.60-13.95 (br s, 1H), 9.46 (s, 1H), 9.05 (s, 1H), 8.91 (s, 2H), 8.81-8.60 (br m, 2H), 7.78-7.54 (m, 2H), 7.26 (t, 1H), 7.08 (t, 1H), 5.60 (br s, 1H), 1.54 (d, 3H). | 14.217 | 2.376 | 404.2 (MH+) | 10 | 5 |
| 33 | [(R)-1-(2,6-Difluoro-phenyl)-ethyl]-[6-(1H-pyrazolo[3,4-d]pyrimidin-4-yl)-quinazolin-2-yl]-amine | A | 1H NMR (DMSO-d6) δ 14.21 (br s, 1H), 9.39 (s, 1H), 9.03 (s, 1H), 8.89 (s, 1H), 8.87 (s, 1H), 8.63 (d, 1H), 8.31 (d, 1H), 7.51 (d, 1H), 7.30 (t, 1H), 7.03 (t, 2H), 5.53 (br m, 1H), 1.62 (d, 3H). | 13.680 | 2.382 | 404.3 (MH+) | 10 | 5 |
| 34 | 4-[2-((R)-1-Phenyl-ethylamino)-quinazolin-6-yl]-7H-pyrrolo[2,3-d]pyrimidine-5-carbonitrile | A | 1H NMR (DMSO-d6) δ 13.42 (br s, 1H), 9.24 (s, 1H), 9.00 (s, 1H), 8.69 (s, 1H), 8.39 (d, 1H), 8.29 (d, 1H), 8.19 (d, 1H), 7.65-7.42 (m, 3H), 7.32 (d, 2H), 7.21 (t, 1H), 5.32 (t, 1H), 1.51 (d, 3H). | 17.847 | 4.556 | 392.4 (MH+) | 10 | 6 |
| 35 | 2-{(R)-1-[6-(1H-Pyrazolo[3,4-d]pyrimidin-4-yl)-quinazolin-2-ylamino]-ethyl}-phenol | A | 1H NMR (DMSO-d6) δ 14.19 (br s, 1H), 9.83 (br s, 1H), 9.39 (s, 1H), 9.03 (s, 1H), 8.91 (s, 1H) 8.88 (s, 1H), 8.63 (d, 1H), 8.28-8.12 (br m, 1H), 7.57 (d, 1H), 7.33 (d, 1H), 7.02 (d, 1H), 6.81 (d, 1H), 6.75 (br s, 1H), 5.55 (br s, 1H), 1.45 (d, 3H). | 20.227 | 2.046 | 384.2 (MH+) | 10 | 5 |
| 36 | 3-{(R)-1-[6-(1H-Pyrazolo[3,4-d]pyrimidin-4-yl)-quinazolin-2-ylamino]-ethyl}-phenol | A | 1H NMR (DMSO-d6) δ 14.20 (br s, 1H), 9.40 (s, 1H), 9.30 (s, 1H), 9.03 (s, 1H), 8.91 (s, 1H), 8.87 (s, 1H), 8.63 (d, 1H), 8.30 (d, 1H), 7.58 (d, 1H), 7.10 (t, 1H), 6.89 (m, 2H), 6.59 (d, 1H), 5.27 (quint, 1H), 1.49 (d, 3H). | 17.963 | 1.879 | 383.9 (MH+) | 10 | 5 |
| 37 | 4-{(R)-1-[6-(1H-Pyrazolo[3,4-d]pyrimidin-4-yl)-quinazolin-2-ylamino]-ethyl}-phenol | A | 1H NMR (DMSO-d6) δ 14.21 (br s, 1H), 9.39 (s, 1H), 9.23 (s, 1H), 9.02 (s, 1H), 8.91 (s, 1H), 8.87 (d, 1H), 8.63 (d, 1H), 8.21 (d, 1H), 7.58 (d, 1H), 7.27 (d, 2H), 6.69 (d, 2H), 5.31-5.21 (m, 1H), 1.490 (d, 3H). | 16.037 | 4.253 | 384.3 (MH+) | 11 | 6 |
| 38 | (S)-2-(2-Fluoro-phenyl)-2-[6-(1H-pyrazolo[3,4-d]pyrimidin-4-yl)-quinazolin-2-ylamino]-ethanol | A | | | 1.884 | 401.8 (MH+) | | 5 |
| 39 | (S)-2-(3-Fluoro-phenyl)-2-[6-(1H-pyrazolo[3,4-d]pyrimidin-4-yl)-quinazolin-2-ylamino]-ethanol | A | | | 1.915 | 402.3 (MH+) | | 5 |
| 40 | (S)-2-(4-Fluoro-phenyl)-2-[6-(1H-pyrazolo[3,4-d]pyrimidin-4-yl)-quinazolin-2-ylamino]-ethanol | A | | | 1.875 | 401.9 (MH+) | | 5 |
| 41 | (R)-3-(2-Fluoro-phenyl)-3-[6-(1H-pyrazolo[3,4- | A | 1H NMR (DMSO-d6) δ 14.21 (br s, 1H), 9.39 | 30.320 | 1.940 | 416.2 (MH+) | 12 | 5 |

-continued

| Example No. | Name | Synthetic scheme | $^1$H NMR | Chiral HPLC RT (min) | LC RT (min) | MS | Chiral HPLC method | LCMS method |
|---|---|---|---|---|---|---|---|---|
| | d]pyrimidin-4-yl)-quinazolin-2-ylamino]-propan-1-ol | | (s, 1H), 9.03 (s, 1H), 8.91 (s, 1H), 8.87 (d, 1H), 8.63 (d, 1H), 8.38 (d, 1H), 7.62-7.50 (m, 2H), 7.25 (q, 1H), 7.18 (q, 2H), 5.71-5.55 (m, 1H), 4.62 (t, 1H), 3.52 (m, 2H), 2.13-1.89 (m, 2H). | | | | | |
| 42 | (R)-3-(3-Fluoro-phenyl)-3-[6-(1H-pyrazolo[3,4-d]pyrimidin-4-yl)-quinazolin-2-ylamino]-propan-1-ol | A | 1H NMR (DMSO-d6) δ 14.21 (br s, 1H), 9.40 (s, 1H), 9.03 (s, 1H), 8.90 (s, 1H), 8.88 (d, 1H), 8.63 (d, 1H), 8.38 (d, 1H), 7.61 (d, 1H), 7.40-7.20 (m, 3H), 7.01 (t, 1H), 5.36 (m, 1H), 4.62 (br s, 1H), 3.55-3.35 (m, 2H), 2.15-1.85 (m, 2H). | 28.297 | 1.897 | 416.2 (MH+) | 12 | 5 |
| 43 | (R)-3-(4-Fluoro-phenyl)-3-[6-(1H-pyrazolo[3,4-d]pyrimidin-4-yl)-quinazolin-2-ylamino]-propan-1-ol | A | 1H NMR (DMSO-d6) δ 14.22 (br s, 1H), 9.39 (s, 1H), 9.03 (s, 1H), 8.91 (s, 1H), 8.88 (d, 1H), 8.63 (d, 1H), 8.38 (d, 1H), 7.57 (d, 1H), 7.51-7.49 (m, 2H), 7.16 (t, 2H), 5.45-5.29 (m, 1H), 4.61 (t, 1H), 3.52-3.39 (m, 2H), 2.15-1.85 (m, 2H). | 28.763 | 1.947 | 416.3 (MH+) | 12 | 5 |

N/A = not applicable

Example 44

Biological Activity (a) Determination of p70S6 Inhibitory Activity

The ability of compounds of the invention to inhibit P70S6 kinase may be determined using the protocol below.

Buffer Composition:

20 mM MOPS, 1 mM EDTA, 0.01% Brij-35, 5% Glycerol, 0.1% b-mercaptoethanol, 1 mg/mL BSA Method:

p70S6K (h) kinase assay

In a final reaction volume of 25 μL, p70S6K (h) (5-10 mU) is incubated with 8 mM MOPS pH 7.0, 0.2 mM EDTA, 100 μM KKRNRTLTV, 10 mM Mg acetate and [γ-33P-ATP] (specific activity approx. 500 cpm/pmol, concentration as required). The reaction is initiated by the addition of the MgATP mix. After incubation for 40 minutes at room temperature, the reaction is stopped by the addition of 5 μL of a 3% phosphoric acid solution. 10 μL of the reaction mixture is then spotted onto a P30 filtermat and washed three times for 5 minutes in 75 mM phosphoric acid and once in methanol prior to drying and scintillation counting.

(b) Evaluation of Brain and Plasma Concentrations in an In Vivo Cassette Mouse Model The compounds of this invention were evaluated in an in vivo cassette mouse model to determine brain and plasma concentrations following oral dosing. This is an industry-standard and recognised means to assess brain penetration of small molecules (for recent literature article, refer to: in vitro permeability analysis, pharmacokinetic and brain distribution study in mice of imperatorin, isoimperatorin and cnidilin in Radix Angelicae Dahuricae, Fitoterapia, Volume 85, March 2013, Pages 144-153). It is also recognised that higher brain concentrations (and higher ratios of brain: plasma concentration) lead to greater exposure in the brain—this is clearly advantageous if the brain is the site of action.

Experimental Method:

For a single cassette study, male CD-1 mice were used (n=3 per timepoint, three timepoints: 1.0 hr, 3.0 hr and 8.0 hr).

5 compounds were dosed PO per cassette (dose level 2.5 mg/kg per compound, dose conc. 0.25 mg/ml, dose volume 10.0 ml/kg).

Formulation used to solubilize compounds: 10% DMSO/90% hydroxypropyl-β-cyclodextrin (20% w/v aqueous)

Sampling was terminal and plasma and brain matrices were generated. To prepare plasma samples, protein was precipitated using acetonitrile. To prepare brain samples, homogenisation and protein precipitation was performed with acetonitrile. Samples were analysed using HPLC-TOF MS using electrospray ionisation.

The brain and plasma concentrations and brain-plasma ratios observed for the compounds tested are set out in the table below.

| Compound Example No. | p70S6K1 $IC_{50}$ (μM) | (d) Plasma conc. at 3 hours (μM) | (d) Brain conc. at 3 hours (μM) | (d) Brain:Plasma ratio at 3 hours |
|---|---|---|---|---|
| 1 | 0.013 | 0.58 | 1.60 | 2.7 |
| 2 | 0.030 | | | |
| 3 | 0.021 | 0.46 | 1.68 | 3.7 |
| 4 | 0.022 | 0.68 | 1.51 | 2.2 |
| 5 | 0.024 | | | |
| 6 | 0.147 | | | |

-continued

| Compound Example No. | p70S6K1 $IC_{50}$ (μM) | (d) Plasma conc. at 3 hours (μM) | (d) Brain conc. at 3 hours (μM) | (d) Brain:Plasma ratio at 3 hours |
|---|---|---|---|---|
| 7 | 0.033 | | | |
| 8 | 0.108 | | | |
| 9 | 0.055 | | | |
| 10 | 0.018 | 0.50 | 0.84 | 1.7 |
| 11 | 0.145 | | | |
| 12 | >3 | | | |
| 13 | 0.043 | | | |
| 14 | 0.057 | | | |
| 15 | 0.097 | | | |
| 16 | 0.106 | | | |
| 17 | 0.110 | | | |
| 18 | 0.025 | | | |
| 19 | 0.010 | 0.60 | 2.42 | 4.0 |
| 20 | 0.167 | | | |
| 21 | 0.071 | | | |
| 22 | 0.131 | | | |
| 23 | 0.118 | | | |
| 24 | 0.204 | | | |
| 25 | 0.049 | | | |
| 26 | 0.067 | | | |
| 27 | 0.041 | | | |
| 28 | 0.015 | 0.42 | 1.07 | 2.6 |
| 29 | >3 | | | |
| 30 | 0.023 | | | |
| 31 | 0.010 | | | |
| 33 | 0.028 | | | |
| 34 | 0.346 | | | |
| 35 | 0.020 | | | |

In summary, the compounds of the invention demonstrate potent inhibition of p70S6K1. The compounds tested exhibit favourable brain and plasma concentrations in mice following oral dosing, with brain concentrations in excess of plasma, leading to high brain: plasma ratios. It is generally considered that a brain: plasma ratio of >0.5 is favourable for treatment of diseases of the brain.

(c) Evaluation of Efficacy of Compounds in Counter-Acting Tumour Initiation and Metastasis in an In Vivo Model of Triple Negative Breast Cancer (TNBC)

It is known that S6K1 has a crucial role in the recurrence of TNBC cancers following surgery, mainly through the activity of S6K1 in promoting survival of cancer cells in the host via phosphorylation and activation of the anti-apoptotic protein Bcl2 and of Gli1 (Belletti 2014). In addition, S6K1 promotes metastasis of TNBC cells (Akar 2010, Hung 2014).

In order to test the efficacy of an inhibitor of S6K1 in an in vivo model of tumour initiation and metastasis, the following experiment was established:

A total of 22 female athymic nude mice (Hsd: Athymic Nude-Foxn1$^{nu}$) were purchased from Harlan (UK) and acclimatised for 7 days prior to study commencement. Animals were housed in IVC cages (5 per cage) with individual mice identified by ear punch. All animals were allowed free access to a standard certified commercial diet and sanitised water during the study. The holding room was maintained under standard conditions: 20-24° C., 40-70% humidity and a 12h light/dark cycle.

On day −1, animals were randomly assigned to treatment groups as indicated in the table below, and drug treatment commenced. On day 0, MDA-MB-231 cells ($1\times10^6$ in matrigel) were implanted into the second mammary fat pad.

The dosing route was PO and the formulation was as follows: 10% DMSO/90% hydroxypropyl-β-cyclodextrin (20% w/v aqueous).

Treatment Groups:

| Group | n | Treatment | Dose | Dosing route | Dosing schedule | Dosing period (days) |
|---|---|---|---|---|---|---|
| 1 | 8 | Vehicle only | — | p.o. | QD | 21 |
| 2 | 8 | Example 1 (mono-HCl salt) | 100 mg/kg | p.o. | BID | 21 |

During the experiment, the following outcome measures were assessed:

(1) Time to palpation of tumour (latency) (2) tumour volume (3) tumour and organ weights as a measure of metastasis (4) visual appearance of metastatic nodules in the lungs.

Outcomes:

(1) Time to Palpation of Tumour

The compound of Example 1 delays time until appearance (palpation) of tumour and also decreases the rate of incidence (see FIG. 1) compared to control.

(2) Tumour Volume

Figure 2:
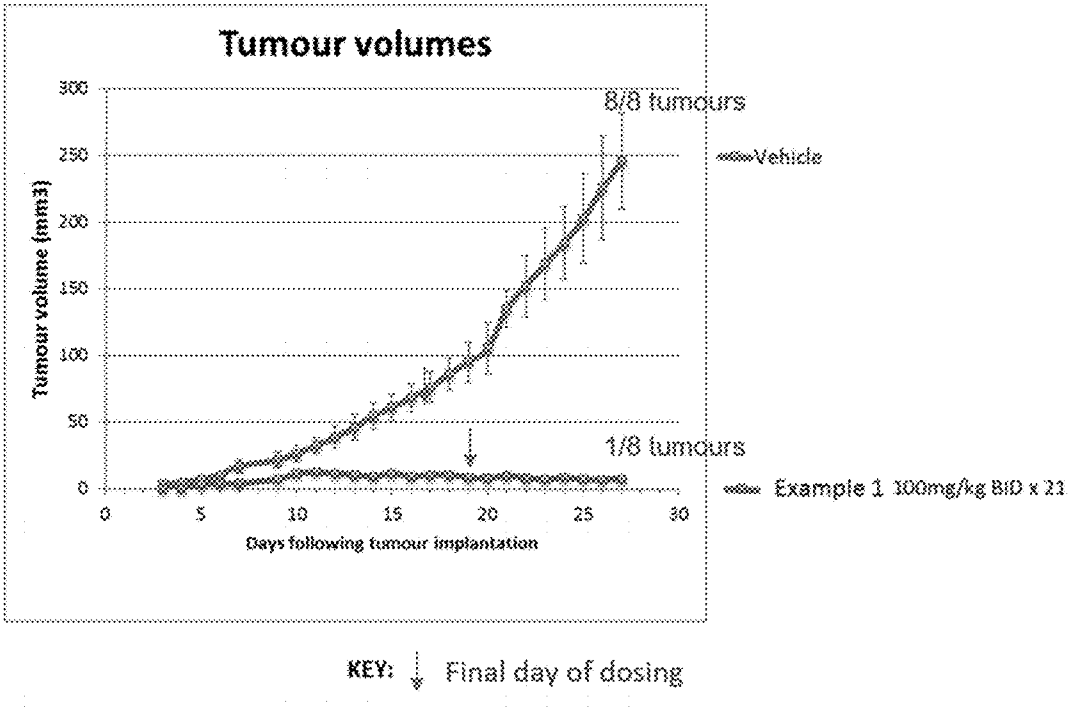
FIG. 2 shows the tumour volume against the number of days following tumour implantation when treated with 100 mg/kg of Example 1 or the vehicle, in the in vivo model of triple negative breast cancer as described in Example 44 herein.

Example 1 induces a significant reduction in volume of tumours (FIG. 2) compared to control.

Figure 3:
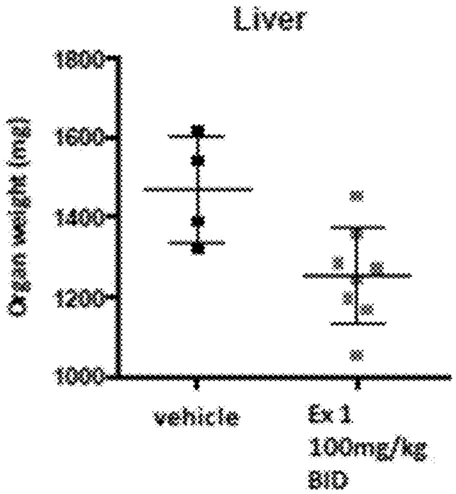
FIG. 3 shows the weights of the livers of the subject mice in Example 44.
Figure 4:
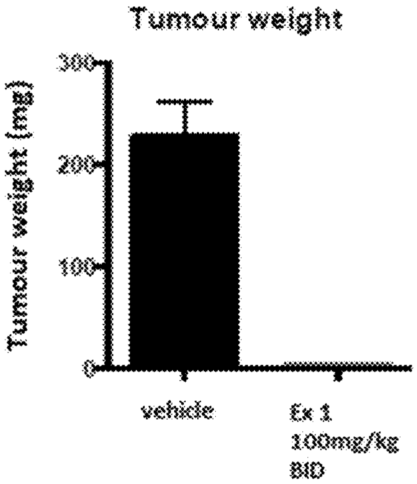
FIG. 4 shows the tumour weights of the subject mice in Example 44.

The liver and tumour weights were taken at day 21. Treatment with the compound of Example 1 led to a reduction in weight of liver compared to the vehicle treated group which may indicate a reduction in metastatic lesions for the treatment group (see FIG. 3). In addition, the tumours from the treated animals weighed significantly less (see FIG. 4).

(3) Visual Appearance of Metastatic Nodules in the Lungs

At necroscopy the lungs of the vehicle and treated animals were examined for presence of metastatic nodules:

| Group no. | Treatment | Dose | No. mice bearing visible lung mets nodules | Mean no. of lung nodules per animal |
|---|---|---|---|---|
| 1 | Vehicle only | — | 3/4 (75%) | 2.3 |
| 2 | Example 1 (mono-HCl salt) | 100 mg/kg BID x 21 | 0/5 (0%) | 0 |

This shows that example 1 is effective in reducing the metastatic burden in the lungs of the mouse arising as spontaneous metastasis from a TNBC primary tumour.

Taken together this indicates that Example 1, an S6K1 inhibitor, is effective in (a) preventing tumour initiation (b) limiting the growth of tumours that do present and (c) preventing metastasis to the lung arising from the primary tumour.

(d) Evaluation of Compounds in the Audiogenic Seizure Assay, an In Vivo Model of Fragile X Syndrome (FXS)

Seizures occur in conjunction with FXS and autism in up to one-quarter of children with these disorders (Berry-Kravis E (2002) Epilepsy in fragile X syndrome. Dev. Med. Child Neurol. 44(11):724-728). Increased susceptibility to sound-induced seizures, called audiogenic seizures (AGS), is a robust and reliable phenotype in FXS mice (Fmr1 KO) that does not occur in VVT mice. The audiogenic seizure assay (AGS) is a well-documented mouse model of FXS (Audiogenic seizures susceptibility in transgenic mice with fragile X syndrome, Epilepsia. 2000 January; 41(1):19-23). In such a model it is possible to dose compounds to observe effects on susceptibility of the mice to audiogenic seizures. The following AGS experiment was set up to test the efficacy of compounds of this application:

The following experiment design was used:

| Group | Mice | n | treatment | Dosing |
|---|---|---|---|---|
| 1 | FXS (Fmr1 KO) | 10 | vehicle | QD x 7 PO |
| 2 | FXS (Fmr1 KO) | 10 | Example 1 (mono-HCl salt), 50 mg/kg | QD x 7 PO |

Strain of FXS mouse used: FVB background

Vehicle used: 10% DMSO/90% hydroxypropyl-β-cyclodextrin (20% w/v aqueous)

Animals were assessed in AGS following 7 consecutive days of dosing.

Method:

The experimental chamber consisted of a plastic cage of dimensions 25×25×47 cm in which a doorbell (Electrical bell Heath Zenith, model 172C-A) had been mounted on the cage roof.

Mice were taken from their housing room one by one and transferred into the experimental chamber and allowed to explore the novel environment (basal noise ~65 dB) for a period of 30 seconds after which point the bell was rung (124 dB) for a period of 60 seconds.

The resulting motor responses were classified using a scale modified from the one originally described by Jobe et al. (1973): no response (NR: pause or continuous exploration), wild running (WR), seizure (S) or respiratory arrest and/or death (RA). The motor response rate is defined as the percentage of animals per group responding to the stimulus.

Results:

| Group | NR | WR | S | RA | Motor Response rate (%) |
|---|---|---|---|---|---|
| 1 | 1 | 9 | 7 | 5 | 9/10 (90%) |
| 2 | 9 | 1 | 0 | 0 | 1/10 (10%) |

The data show that the incidence of audiogenic seizures and severity of response were both reduced by administration of Example 1.

Example 45

Pharmaceutical Formulations (i) Tablet Formulation

A tablet composition containing a compound of the formula (1) as defined in any one of Embodiments 1.0 to 1.116 may be prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a compound of the formula (1) as defined in any one of Embodiments 1.0 to 1.116 with 100 mg lactose and filling the resulting mixture into standard opaque hard gelatin capsules.

(iii) Injectable Formulation I

A parenteral composition for administration by injection can be prepared by dissolving a compound of the formula (1) as defined in any one of Embodiments 1.0 to 1.116 in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a compound of the formula (1) as defined in any one of Embodiments 1.0 to 1.116 (2 mg/ml) and mannitol (50 mg/ml), sterile filtering the solution and filling into sealable 1 ml vials or ampoules.

v) Injectable Formulation III

A formulation for i.v. delivery by injection or infusion can be prepared by dissolving the compound of formula (1) as defined in any one of Embodiments 1.0 to 1.116 (e.g. in a salt form) in water at 20 mg/ml. The vial is then sealed and sterilised by autoclaving.

vi) Injectable Formulation IV

A formulation for i.v. delivery by injection or infusion can be prepared by dissolving the compound of formula (1) as defined in any one of Embodiments 1.0 to 1.116 (e.g. in a salt form) in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a compound of the formula (1) as defined in any one of Embodiments 1.0 to 1.116 with pharmaceutical grade corn oil to give a concentration of 5 mg/ml. The composition is sterilised and filled into a suitable container.

viii) Lyophilised Formulation

Aliquots of formulated compound of formula (1) as defined in any one of Embodiments 1.0 to 1.116 are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A compound of the formula (1):

(1)

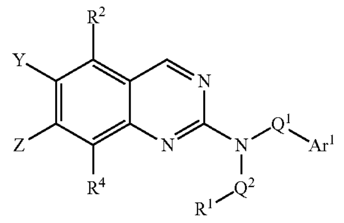

or a salt, tautomer or N-oxide thereof;

wherein:

one of Y and Z is $R^3$ and the other is $Ar^2$;

$Q^1$ is a $C_{1-8}$ alkylene group optionally substituted by one or two substituents selected from hydroxy and $C_{1-4}$ hydrocarbyloxy, provided that when a hydroxy substituent is present, there are at least two carbon atoms between the hydroxy substituent and the nitrogen atom to which $Q^2$ is attached; and wherein a carbon atom of the $C_{1-8}$ alkylene group may optionally be replaced by a cyclopropane-1,1-diyl or cyclobutane-1,1-diyl group provided that the total number of carbon atoms in an alkylene group containing such a replacement does not exceed 8;

$Q^2$ is a bond or a $C_{1-8}$ alkylene group optionally substituted by one or two substituents selected from hydroxy and $C_{1-4}$ hydrocarbyloxy, provided that when a hydroxy substituent is present, there are at least two carbon atoms between the hydroxy substituent and the nitrogen atom to which $Q^2$ is attached;

$R^1$ is selected from hydrogen, $NR^xR^y$ and a group $Cy^1$;

$R^x$ and $R^y$ are the same or different and each is selected from hydrogen, $C_{1-4}$ hydrocarbyl or hydroxy-$C_{1-4}$ hydrocarbyl; or $NR^xR^y$ forms a 4 to 7-membered heterocyclic ring containing a total of 1 or 2 heteroatom ring members of which one is N and the other is selected from N, O and S and oxidised forms thereof, the heterocyclic ring being optionally substituted with one or two substituents selected from $C_{1-4}$ hydrocarbyl, oxo, amino, mono-$C_{1-4}$ hydrocarbylamino, di-$C_{1-4}$hydrocarbylamino, fluorine and hydroxy, provided that there are at least two carbon atoms in line between the amino, mono-$C_{1-4}$ hydrocarbylamino, di-$C_{1-4}$hydrocarbylamino and hydroxy substituents when present and the nitrogen atom of the $NR^xR^y$ group;

$Cy^1$ is a C-linked 3 to 7 membered monocyclic non-aromatic carbocyclic or heterocyclic group containing 0, 1 or 2 heteroatom ring members selected from N, O and S and oxidised forms of S, and being optionally substituted with one or two substituents selected from $C_{1-3}$ hydrocarbyl, fluorine, oxo and hydroxy;

$R^2$ and $R^4$ are the same or different and each is selected from hydrogen, fluorine, chlorine, $C_{1-2}$ alkyl and $C_{1-2}$ alkoxy, wherein each $C_{1-2}$ alkyl and $C_{1-2}$ alkoxy is optionally substituted with two or more fluorine atoms;

$R^3$ is selected from hydrogen, fluorine, chlorine, $C_{1-2}$ alkyl and $C_{1-2}$ alkoxy, wherein each $C_{1-2}$ alkyl and $C_{1-2}$ alkoxy is optionally substituted with two or more fluorine atoms;

$Ar^1$ is a monocyclic 5 or 6-membered aryl or heteroaryl ring containing 0, 1 or 2 heteroatom ring members selected from O, N and S, the aryl or heteroaryl being optionally substituted with 1, 2 or 3 substituents $R^5$ which are the same or different and are selected from halogen, cyano and a group $R^a$-$R^b$;

$R^a$ is a bond, O, CO, $X^3C(X^4)$, $C(X^4)X^3$, $X^3C(X^4)X^3$, S, SO, $SO_2$, $NR^c$, $SO_2NR^c$ or $NR^cSO_2$;

$R^b$ is:

hydrogen;

a carbocyclic or heterocyclic group having from 3 to 7 ring members, of which 0, 1, 2 or 3 are heteroatom ring members selected from O, N and S and oxidised forms of S, the carbocyclic or heterocyclic group being optionally substituted with one or more substituents $R^6$; or an acyclic $C_{1-8}$ hydrocarbon group optionally substituted with one or more substituents selected from hydroxy; oxo; halogen; cyano; carboxy; amino; mono- or di-$C_{1-4}$ alkylamino; and carbocyclic and heterocyclic groups having from 3 to 7 ring members, of which 0, 1, 2 or 3 are heteroatom ring members selected from O, N and S and oxidised forms of S, the carbocyclic or heterocyclic group being optionally substituted with one or more substituents $R^6$; wherein one or two but not all of the carbon atoms of the acyclic $C_{1-8}$ hydrocarbon group may optionally be replaced by O, S, SO, $SO_2$, $NR^c$, $X^3C(X^4)$, $C(X^4)X^3$ or $X^3C(X^4)X^3$;

$R^6$ is selected from the substituents $R^5$ except that $R^6$ does not consist of or contain a carbocyclic or heterocyclic group;

$X^3$ is O, S or $NR^c$; and $X^4$ is =O, =S or =$NR^c$; and $R^c$ is hydrogen or $C_{1-4}$ hydrocarbyl;

$Ar^2$ is a bicyclic 8 to 11-membered heteroaryl group containing 1, 2, 3 or 4 heteroatom ring members selected from O, N and S and being optionally substituted with 1, 2 or 3 substituents $R^7$ selected from oxo, fluorine; chlorine; bromine; $C_{1-4}$ hydrocarbyl optionally substituted with one or more fluorine atoms; $C_{1-4}$ hydrocarbyloxy optionally substituted with one or more fluorine atoms; hydroxy; cyano; $N(R^c)_2$; $R^c$—C(O)—; $R^c$—C(O)N($R^c$)—; $(R^c)_2$NC(O)—; $R^c$—$SO_2NR^c$—; $R^c$—NHC(O)NH—; $(R^c)_2NSO_2$—; and five and six-membered monocyclic groups containing from 0 to 3 heteroatom ring members selected from O, N and S, the five and six-membered monocyclic groups being unsubstituted or substituted with one or more substituents $R^8$ selected from $C_{1-4}$ hydrocarbyl, $C_{1-4}$ hydrocarbyloxy, cyano, hydroxy, oxo, halogen, amino, mono-$C_{1-4}$ hydrocarbylamino and di-$C_{1-4}$hydrocarbylamino and wherein the hydrocarbyl moieties when present are optionally substituted with fluorine, $C_{1-2}$ alkoxy, hydroxy, amino, mono-di-$C_{1-2}$alkylamino or di-$C_{1-4}$alkylamino;

and wherein, in each substituent consisting of or containing a hydrocarbyl group, the hydrocarbyl group is selected from alkyl, alkenyl, alkynyl and cycloalkyl groups and combinations thereof.

2. A compound according to claim 1 having the formula (1):

(1)

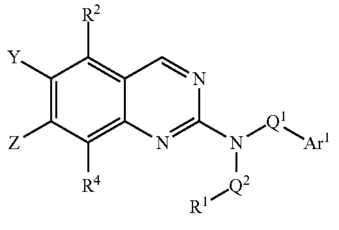

or a salt, tautomer or N-oxide thereof;

wherein:

one of Y and Z is $R^3$ and the other is Are;

$Q^1$ is a $C_{1-8}$ alkylene group optionally substituted by one or two substituents selected from hydroxy and $C_{1-4}$ hydrocarbyloxy, provided that when a hydroxy substituent is present, there are at least two carbon atoms between the hydroxy substituent and the nitrogen atom to which $Q^2$ is attached;

$Q^2$ is a bond or a $C_{1-8}$ alkylene group optionally substituted by one or two substituents selected from hydroxy and $C_{1-4}$ hydrocarbyloxy, provided that when a hydroxy substituent is present, there are at least two carbon atoms between the hydroxy substituent and the nitrogen atom to which $Q^2$ is attached;

$R^1$ is selected from hydrogen, $NR^xR^y$ and a group $Cy^1$;

$R^x$ and $R^y$ are the same or different and each is selected from hydrogen, $C_{1-4}$ hydrocarbyl or hydroxy-$C_{1-4}$ hydrocarbyl; or $NR^xR^y$ forms a 4 to 7-membered heterocyclic ring containing a total of 1 or 2 heteroatom ring members of which one is N and the other is selected from N, O and S and oxidised forms thereof, the heterocyclic ring being optionally substituted with one or two substituents selected from $C_{1-4}$ hydrocarbyl, oxo, amino, mono-$C_{1-4}$ hydrocarbylamino, di-$C_{1-4}$hydrocarbylamino, fluorine and hydroxy, provided that there are at least two carbon atoms in line between the amino, mono-$C_{1-4}$ hydrocarbylamino, di-$C_{1-4}$hydrocarbylamino and hydroxy substituents when present and the nitrogen atom of the $NR^xR^y$ group;

$Cy^1$ is a C-linked 3 to 7 membered monocyclic non-aromatic carbocyclic or heterocyclic group containing 0, 1 or 2 heteroatom ring members selected from N, O and S and oxidised forms of S, wherein the carbocyclic and heterocyclic groups are optionally substituted with one or two substituents selected from $C_{1-3}$ hydrocarbyl, fluorine, oxo and hydroxy;

$R^2$ and $R^4$ are the same or different and each is selected from hydrogen, fluorine, chlorine, $C_{1-2}$ alkyl and $C_{1-2}$ alkoxy, wherein each $C_{1-2}$ alkyl and $C_{1-2}$ alkoxy is optionally substituted with two or more fluorine atoms;

$R^3$ is selected from hydrogen, fluorine, chlorine, $C_{1-2}$ alkyl and $C_{1-2}$ alkoxy, wherein each $C_{1-2}$ alkyl and $C_{1-2}$ alkoxy is optionally substituted with two or more fluorine atoms;

$Ar^1$ is a monocyclic 5 or 6-membered aryl or heteroaryl ring containing 0, 1 or 2 heteroatom ring members selected from O, N and S, the aryl or heteroaryl being optionally substituted with 1, 2 or 3 substituents $R^5$ which are the same or different and are selected from halogen, cyano and a group $R^a$-$R^b$;

$R^a$ is a bond, O, CO, $X^3C(X^4)$, $C(X^4)X^3$, $X^3C(X^4)X^3$, S, SO, $SO_2$, $NR^c$, $SO_2NR^c$ or $NR^cSO_2$;

$R^b$ is:

hydrogen;

a carbocyclic or heterocyclic group having from 3 to 7 ring members, of which 0, 1, 2 or 3 are heteroatom ring members selected from O, N and S and oxidised forms of S, the carbocyclic or heterocyclic group being optionally substituted with one or more substituents $R^6$; or an acyclic $C_{1-8}$ hydrocarbon group optionally substituted with one or more substituents selected from hydroxy; oxo; halogen; cyano; carboxy; amino; mono- or di-$C_{1-4}$ alkylamino; and carbocyclic and heterocyclic groups having from 3 to 7 ring members, of which 0, 1, 2 or 3 are heteroatom ring members selected from O, N and S and oxidised forms of S, the carbocyclic or heterocyclic group being optionally substituted with one or more substituents $R^6$; wherein one or two but not all of the carbon atoms of the acyclic $C_{1-8}$ hydrocarbon group may optionally be replaced by O, S, SO, $SO_2$, $NR^c$, $X^3C(X^4)$, $C(X^4)X^3$ or $X^3C(X^4)X^3$;

$R^6$ is selected from the substituents $R^5$ except that $R^6$ does not consist of or contain a carbocyclic or heterocyclic group;

$X^3$ is O, S or $NR^c$; and $X^4$ is =O, =S or =$NR^c$; and $R^c$ is hydrogen or $C_{1-4}$ hydrocarbyl;

$Ar^2$ is a bicyclic 8 to 11-membered heteroaryl group containing 1, 2, 3 or 4 heteroatom ring members selected from O, N and S and being optionally substituted with 1, 2 or 3 substituents $R^7$ selected from oxo, fluorine; chlorine; bromine; $C_{1-4}$ hydrocarbyl optionally substituted with one or more fluorine atoms; $C_{1-4}$ hydrocarbyloxy optionally substituted with one or more fluorine atoms; hydroxy; cyano; $N(R^c)_2$; $R^c$-C(O)-; $R^c$-C(O)N($R^c$)-; $(R^c)_2$NC(O)-; $R^c$—$SO_2NR^c$-; $R^c$-NHC(O)NH—; $(R^c)_2NSO_2$-; and five and six-membered monocyclic groups containing from 0 to 3 heteroatom ring members selected from O, N and S, the five and six-membered monocyclic groups being unsubstituted or substituted with one or more substituents $R^8$ selected from $C_{1-4}$ hydrocarbyl, $C_{1-4}$ hydrocarbyloxy, cyano, hydroxy, oxo, halogen, amino, mono-$C_{1-4}$ hydrocarbylamino and di-$C_{1-4}$hydrocarbylamino and wherein the hydrocarbyl moieties when present are optionally substituted with fluorine, $C_{1-2}$ alkoxy, hydroxy, amino, mono-di-$C_{1-2}$alkylamino or di-$C_{1-4}$alkylamino;

and wherein, in each substituent consisting of or containing a hydrocarbyl group, the hydrocarbyl group is selected from alkyl, alkenyl, alkynyl and cycloalkyl groups and combinations thereof.

3. A compound according to claim 1 wherein Y is Are and Z is $R^3$.

4. A compound according to claim 1 wherein $Q^1$ is $C_{1-4}$ alkylene optionally substituted by one or two substituents selected from hydroxy and $C_{1-4}$ hydrocarbyloxy, provided that when a hydroxy substituent is present, there are at least two carbon atoms between the hydroxy substituent and the nitrogen atom to which $Q^2$ is attached.

5. A compound according to claim 4 wherein $Q^1$ is selected from $CH_2$, $CH(CH_3)$, $CH(CH_2OH)$ and $CH(CH_2CH_2OH)$.

6. A compound according to claim 1 wherein $Q^2$ is a bond or $C_{1-3}$ alkylene.

7. A compound according to claim 1 wherein $R^1$ is selected from:

hydrogen;

a group $Cy^1$ wherein $Cy^1$ is selected from 4 to 7 membered saturated heterocyclic groups containing a first ring member which is nitrogen and optionally a second ring member selected from N, O and S, wherein the heterocyclic groups are optionally substituted with one or two substituents selected from $C_{1-3}$ alkyl, cyclopropyl, fluorine and hydroxyl; and $NR^xR^y$, wherein $R^x$ and $R^y$ are the same or different and each is selected from hydrogen, $C_{1-4}$ alkyl, cyclopropyl, methylcyclopropyl, cyclopropylmethyl, and hydroxy-$C_{2-4}$ alkyl.

8. A compound according to claim 7 wherein $R^1$ is hydrogen.

9. A compound according to claim 1 wherein $Ar^1$ is a monocyclic aryl or heteroaryl ring selected from phenyl, furyl, thienyl and pyridyl, each optionally substituted with 1, 2 or 3 substituents $R^5$ which are the same or different.

10. A compound according to claim 9 wherein $Ar^1$ is a phenyl ring optionally substituted with 1, 2 or 3 substituents $R^5$ which are the same or different.

11. A compound according to claim 1 wherein $R^2$ is hydrogen.

12. A compound according to claim 1 wherein $R^3$ is hydrogen.

13. A compound according to claim 1 wherein $R^4$ is hydrogen.

14. A compound according to claim 1 wherein the compound is of the formula (3):

(3)

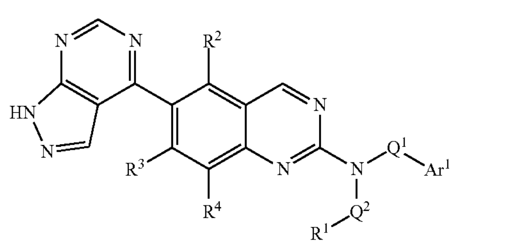

or a salt, tautomer or N-oxide thereof, wherein $R^1$, $R^2$, $R^3$, $R^4$, $Q^1$, $Q^2$ and $Ar^1$ are as defined in claim 1.

15. A compound according to claim 1 wherein the compound is of the formula (4):

(4)

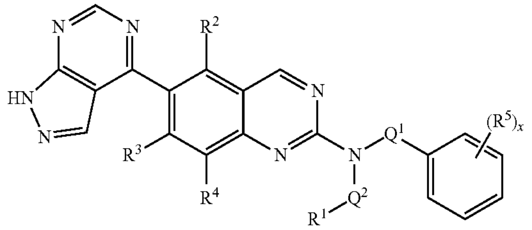

or a salt, tautomer or N-oxide thereof, wherein $R^1$, $R^2$, $R^3$, $R^4$, $R^5$, $Q^1$ and $Q^2$ are as defined in claim 1 and x is 0, 1, 2, or 3.

16. A pharmaceutical composition comprising a compound as defined in claim 1 and a pharmaceutically acceptable excipient.

17. A compound according to claim 1 which is selected from the group consisting of:

((R)-1-Phenyl-ethyl)-[6-(1H-pyrazolo[3,4-d]pyrimidin-4-yl)-quinazolin-2-yl]-amine;

((R)-1-(3-Chloro-phenyl)-ethyl)-[6-(1H-pyrazolo[3,4-d]pyrimidin-4-yl)-quinazolin-2-yl]-amine;

((R)-1-(3-Fluoro-phenyl)-ethyl)-[6-(1H-pyrazolo[3,4-d]pyrimidin-4-yl)-quinazolin-2-yl]-amine;

((R)-1-(4-Fluoro-phenyl)-ethyl)-[6-(1H-pyrazolo[3,4-d]pyrimidin-4-yl)-quinazolin-2-yl]-amine;

((S)-2-Hydroxy-1-phenyl-ethyl)-[6-(1H-pyrazolo[3,4-d]pyrimidin-4-yl)-quinazolin-2-yl]-amine;

Benzyl-[6-(1H-pyrazolo[3,4-d]pyrimidin-4-yl)-quinazolin-2-yl]-methylamine;

(3-Fluorobenzyl)-[6-(1H-pyrazolo[3,4-d]pyrimidin-4-yl)-quinazolin-2-yl]-amine;

((R)-1-Phenyl-ethyl)-[6-(1H-pyrazolo[3,4-b]pyridin-4-yl)-quinazolin-2-yl]-amine;

Benzyl-(S)-1-morpholin-3-ylmethyl-[6-(1H-pyrazolo[3,4-d]pyrimidin-4-yl)-quinazolin-2-yl]-amine;

[(R)-1-(3,4-Difluoro-phenyl)-ethyl]-[6-(1H-pyrazolo[3,4-d]pyrimidin-4-yl)-quinazolin-2-yl]-amine;

Benzyl-[6-(1H-pyrazolo[3,4-d]pyrimidin-4-yl)-quinazolin-2-yl]-amine;

(3,4-Difluoro-benzyl)-[6-(1H-pyrazolo[3,4-d]pyrimidin-4-yl)-quinazolin-2-yl]-amine;

N-(3-{[6-(1H-Pyrazolo[3,4-d]pyrimidin-4-yl)-quinazolin-2-ylamino]-methyl}-phenyl)-methanesulfonamide;

[(R)-1-(3-Methoxy-phenyl)-ethyl]-[6-(1H-pyrazolo[3,4-d]pyrimidin-4-yl)-quinazolin-2-yl]-amine;

[(R)-1-(2-Fluoro-phenyl)-ethyl]-[6-(1H-pyrazolo[3,4-d]pyrimidin-4-yl)-quinazolin-2-yl]-amine;

N-(3-{(R)-1-[6-(1H-Pyrazolo[3,4-d]pyrimidin-4-yl)-quinazolin-2-ylamino]-ethyl}-phenyl)-methanesulfonamide;

(R)-3-Phenyl-3-[6-(1H-pyrazolo[3,4-d]pyrimidin-4-yl)-quinazolin-2-ylamino]-propan-1-ol

[(R)-1-(2,4-Difluoro-phenyl)-ethyl]-[6-(1H-pyrazolo[3,4-d]pyrimidin-4-yl)-quinazolin-2-yl]-amine;

[(R)-1-(2,6-Difluoro-phenyl)-ethyl]-[6-(1H-pyrazolo[3,4-d]pyrimidin-4-yl)-quinazolin-2-yl]-amine;

2-{(R)-1-[6-(1H-Pyrazolo[3,4-d]pyrimidin-4-yl)-quinazolin-2-ylamino]-ethyl}-phenol;

3-{(R)-1-[6-(1H-Pyrazolo[3,4-d]pyrimidin-4-yl)-quinazolin-2-ylamino]-ethyl}-phenol;

4-{(R)-1-[6-(1H-Pyrazolo[3,4-d]pyrimidin-4-yl)-quinazolin-2-ylamino]-ethyl}-phenol;

(S)-2-(2-Fluoro-phenyl)-2-[6-(1H-pyrazolo[3,4-d]pyrimidin-4-yl)-quinazolin-2-ylamino]-ethanol;

(S)-2-(3-Fluoro-phenyl)-2-[6-(1H-pyrazolo[3,4-d]pyrimidin-4-yl)-quinazolin-2-ylamino]-ethanol; and (S)-2-(4-Fluoro-phenyl)-2-[6-(1H-pyrazolo[3,4-d]pyrimidin-4-yl)-quinazolin-2-ylamino]-ethanol;

and pharmaceutically acceptable salts thereof.

18. A compound according to claim 1 which is selected from the group consisting of:

((R)-1-Phenyl-ethyl)-[6-(1H-pyrazolo[3,4-d]pyrimidin-4-yl)-quinazolin-2-yl]-amine;

((R)-1-(3-Chloro-phenyl)-ethyl)-[6-(1H-pyrazolo[3,4-d]pyrimidin-4-yl)-quinazolin-2-yl]-amine;

((R)-1-(3-Fluoro-phenyl)-ethyl)-[6-(1H-pyrazolo[3,4-d]pyrimidin-4-yl)-quinazolin-2-yl]-amine;

((R)-1-(4-Fluoro-phenyl)-ethyl)-[6-(1H-pyrazolo[3,4-d]pyrimidin-4-yl)-quinazolin-2-yl]-amine;

(3-Fluorobenzyl)-[6-(1H-pyrazolo[3,4-d]pyrimidin-4-yl)-quinazolin-2-yl]-amine;

[(R)-1-(3,4-Difluoro-phenyl)-ethyl]-[6-(1H-pyrazolo[3,4-d]pyrimidin-4-yl)-quinazolin-2-yl]-amine;

[(R)-1-(2-Fluoro-phenyl)-ethyl]-[6-(1H-pyrazolo[3,4-d]pyrimidin-4-yl)-quinazolin-2-yl]-amine;

(R)-3-Phenyl-3-[6-(1H-pyrazolo[3,4-d]pyrimidin-4-yl)-quinazolin-2-ylamino]-propan-1-ol;

[(R)-1-(2,4-Difluoro-phenyl)-ethyl]-[6-(1H-pyrazolo[3,4-d]pyrimidin-4-yl)-quinazolin-2-yl]-amine;

[(R)-1-(2,6-Difluoro-phenyl)-ethyl]-[6-(1H-pyrazolo[3,4-d]pyrimidin-4-yl)-quinazolin-2-yl]-amine;

2-{(R)-1-[6-(1H-Pyrazolo[3,4-d]pyrimidin-4-yl)-quinazolin-2-ylamino]-ethyl}-phenol;

3-{(R)-1-[6-(1H-Pyrazolo[3,4-d]pyrimidin-4-yl)-quinazolin-2-ylamino]-ethyl}-phenol; and (S)-2-(2-Fluoro-phenyl)-2-[6-(1H-pyrazolo[3,4-d]pyrimidin-4-yl)-quinazolin-2-ylamino]-ethanol;

and pharmaceutically acceptable salts thereof.

19. A compound according to claim 1 which is selected from the group consisting of:

((R)-1-Phenyl-ethyl)-[6-(1H-pyrazolo[3,4-d]pyrimidin-4-yl)-quinazolin-2-yl]-amine;

((R)-1-(3-Fluoro-phenyl)-ethyl)-[6-(1H-pyrazolo[3,4-d]pyrimidin-4-yl)-quinazolin-2-yl]-amine;

((R)-1-(4-Fluoro-phenyl)-ethyl)-[6-(1H-pyrazolo[3,4-d]pyrimidin-4-yl)-quinazolin-2-yl]-amine;

(3-Fluorobenzyl)-[6-(1H-pyrazolo[3,4-d]pyrimidin-4-yl)-quinazolin-2-yl]-amine;

[(R)-1-(3,4-Difluoro-phenyl)-ethyl]-[6-(1H-pyrazolo[3,4-d]pyrimidin-4-yl)-quinazolin-2-yl]-amine;

[(R)-1-(2-Fluoro-phenyl)-ethyl]-[6-(1H-pyrazolo[3,4-d]pyrimidin-4-yl)-quinazolin-2-yl]-amine; and (S)-2-(2-Fluoro-phenyl)-2-[6-(1H-pyrazolo[3,4-d]pyrimidin-4-yl)-quinazolin-2-ylamino]-ethanol;

and pharmaceutically acceptable salts thereof.

20. ((R)-1-Phenyl-ethyl)-[6-(1H-pyrazolo[3,4-d]pyrimidin-4-yl)-quinazolin-2-yl]-amine or a pharmaceutically acceptable salt thereof.

* * * * *

UNITED STATES PATENT AND TRADEMARK OFFICE

CERTIFICATE OF CORRECTION

PATENT NO. : 10,344,033 B2
APPLICATION NO. : 15/764960
DATED : July 9, 2019
INVENTOR(S) : Boyle et al.

It is certified that error appears in the above-identified patent and that said Letters Patent is hereby corrected as shown below:

In the Claims

Column 120, Line 61: Claim 2, Delete “Are” and insert -- $Ar^2$ --

Column 122, Line 35: Claim 3, Delete “Are” and insert -- $Ar^2$ --

Signed and Sealed this
Third Day of September, 2019

Andrei Iancu
*Director of the United States Patent and Trademark Office*